United States Patent
Golf et al.

(10) Patent No.: US 10,456,375 B2
(45) Date of Patent: Oct. 29, 2019

(54) SPECIFICALLY MESO-SUBSTITUTED PORPHYRINS AND CHLORINS FOR PHOTODYNAMIC THERAPY

(71) Applicants: biolitec Unternehmensbeteiligungs II AG, Vienna (AT); FREIE UNIVERSITÄT BERLIN, Berlin (DE)

(72) Inventors: Hartwig Richard Arthur Golf, Berlin (DE); Arno Wiehe, Berlin (DE); Susanna Graefe, Jena (DE); Volker Albrecht, Nuthetal (DE); Hans-Ulrich Reißig, Berlin (DE)

(73) Assignee: Biolitec Unternehmensbeteiligungs II AG, Vienna (AT)

( * ) Notice: Subject to any disclaimer, the term of this patent is extended or adjusted under 35 U.S.C. 154(b) by 0 days.

(21) Appl. No.: 15/515,950

(22) PCT Filed: Sep. 30, 2015

(86) PCT No.: PCT/IB2015/057501
§ 371 (c)(1),
(2) Date: Mar. 30, 2017

(87) PCT Pub. No.: WO2016/051361
PCT Pub. Date: Apr. 7, 2016

(65) Prior Publication Data
US 2018/0036284 A1    Feb. 8, 2018

Related U.S. Application Data

(60) Provisional application No. 62/057,353, filed on Sep. 30, 2014.

(51) Int. Cl.
| | |
|---|---|
| C07D 403/14 | (2006.01) |
| A61K 31/4025 | (2006.01) |
| A61K 31/409 | (2006.01) |
| C07D 487/22 | (2006.01) |
| C07F 5/02 | (2006.01) |
| A61K 31/03 | (2006.01) |

(52) U.S. Cl.
CPC ............ *A61K 31/409* (2013.01); *A61K 31/03* (2013.01); *C07D 487/22* (2013.01); *C07F 5/02* (2013.01)

(58) Field of Classification Search
CPC .......................... C07D 403/14; A61K 31/4025
USPC .......................................... 548/518; 514/422
See application file for complete search history.

(56) References Cited

PUBLICATIONS

Kralova, J. et al.: Glycol porphyrin derivatives as potent photodynamic inducers of apoptosis in tumor cells. J. Med. Chem., vol. 51, pp. 5964-5973, 2008.*

* cited by examiner

*Primary Examiner* — Charanjit Aulakh
(74) *Attorney, Agent, or Firm* — BJ Associates; Bolesh J. Skutnik

(57) ABSTRACT

Biologically active compounds that can be used as photosensitizers for diagnostic and therapeutic applications, particularly for PDT of cancer, infections and other hyperproliferative diseases, fluorescence diagnosis and PDT treatment of a non-tumorous indication such as arthritis, inflammatory diseases, viral or bacterial infections, dermatological, opthamological or urological disorders are provided as well as providing methods to obtain them in pharmaceutical quality. One embodiment consists of a method to synthesize a porphyrin with a defined arrangement of meso-substituents and then converting this porphyrin system to a chlorin system by dihydroxylation or reduction, and if more than one isomer is formed separate them by chromatography either on normal or reversed phase silica. In another embodiment the substituents on the porphyrin are selected to direct the reduction or dihydroxylation to the chlorin so that a certain isomer is selectively formed. Another embodiment is to provide amphiphilic compounds with a higher membrane affinity and increased PDT-efficacy. In other embodiments the nucleophilic substitution on pentafluorophenyl-substituted tetrapyrroles is used to obtain compounds with a high PDT-efficacy. In another embodiment substituents are identified that via their steric and/or electronic influence direct the dihydroxylation or reduction with diimine so that one isomer is favored. Another embodiment consists of formulating the desired tetrapyrrole photosensitizer into a pharmaceutical formulation to be injected into the body avoiding undesirable effects like solubility problems or delayed pharmacokinetics of the tetrapyrrole systems.

16 Claims, 15 Drawing Sheets

Figure 1B

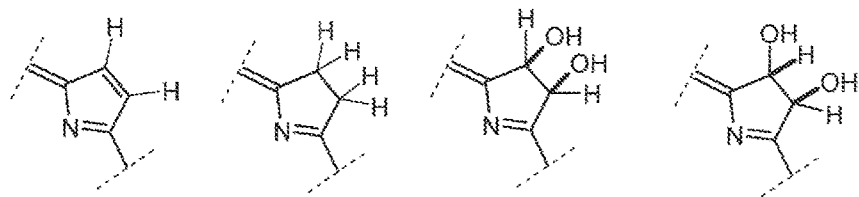

Wherein: B is:

porphyrin system    chlorin system    chlorin system    chlorin system

X is:    NH, O or S $R^1$ is:    a linear or branched alkyl chain with 3-4 carbon atoms and containing at least two hydroxyl moieties.

$R^2$ is:    a substituent either in the *meta-* or *para-* position of the phenyl ring with $R^2$ = -OH, -COOH, -COOY, -NHY, OY, -NH-Z-COOH, or -CO-Z-$NH_2$.

Wherein:    Y is    a polyethyleneglycol-residue with $(CH_2CH_2O)_n CH_3$ with n = 1–30 or a carbohydrate moiety Z is peptides or oligopeptides wherein n = 1–30.

Figure 2A

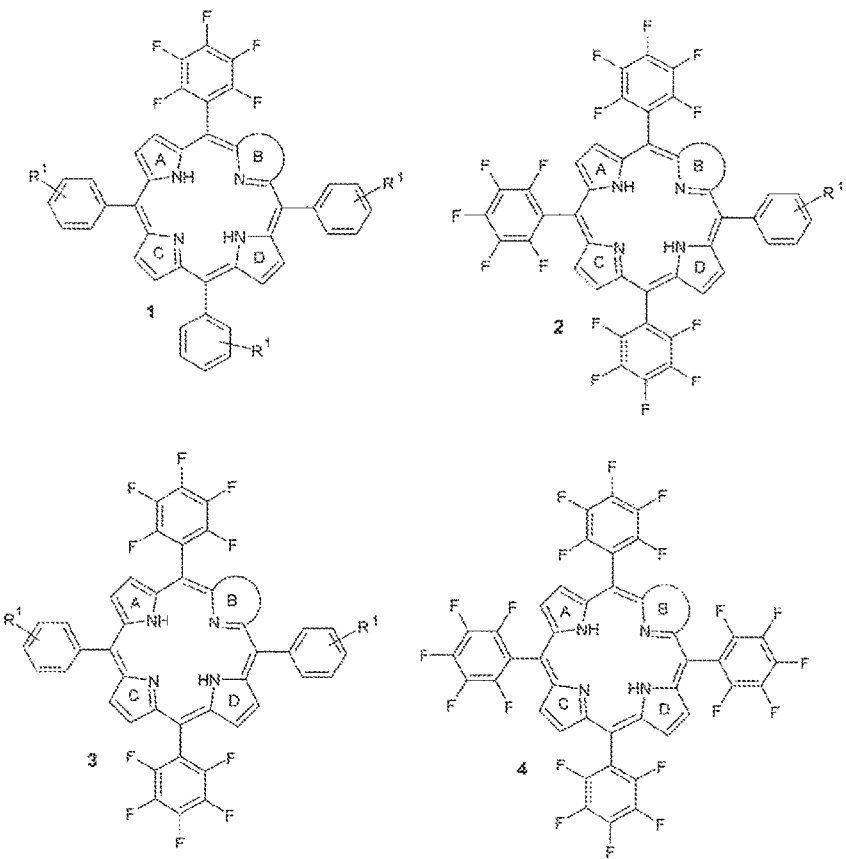

Wherein: B is:

R¹ is: a substituent either in the *meta*- or *para*- position of the phenyl ring with R² = -OH, -COOH, -OR², -COOR², -COOY, -NHY, OY, -NH-Z-COOH, or -CO-Z-NH₂.

Wherein: R² is a suitable protection group

Y is a polyethyleneglycol-residue with $(CH_2CH_2O)_nCH_3$ with n = 1–30 or a carbohydrate moiety Z is a peptide or oligopeptide wherein n = 1–30.

Wherein: B is:

SPECIFICALLY MESO-SUBSTITUTED PORPHYRINS AND CHLORINS FOR PHOTODYNAMIC THERAPY

NATIONAL FILING UNDER 35 USC 371

This application is being filed as a US National Stage under 35 USC 371 of International Application No. PCT/IB2015/057501, filed on Sep. 30, 2015, which claims the benefit of U.S. Provisional Patent Application No. 62/057,353, filed on Sep. 30, 2014, by Hartwig Richard Arthur Golf et al. entitled, "SPECIFICALLY meso-SUBSTITUTED PORPHYRINS AND CHLORINS FOR PHOTODYNAMIC THERAPY", both of which are hereby expressly incorporated by reference in its entirety as part of the present disclosure.

BACKGROUND OF THE INVENTION

1. Field of the Invention

The invention relates to the chemistry of biologically active compounds. More particularly to specifically substituted porphyrin and chlorin derivatives that can be used as photosensitizers for a wide range of light irradiation treatments such as photodynamic therapy of cancer, infections and other diseases.

2. Invention Disclosure Statement

Photodynamic therapy (PDT) is one of the most promising techniques being explored for use in a variety of medical applications [1], [2], and particularly is a well-recognized treatment for the destruction of tumors [3]. Photodynamic therapy uses light and a photosensitizer (a dye) to achieve its desired medical effect. A large number of naturally occurring and synthetic dyes have been evaluated as potential photosensitizers for photodynamic therapy. Perhaps the most widely studied photosensitizers are the tetrapyrrolic macrocyclic compounds. Among them, especially porphyrins and chlorins have been tested for their PDT efficacy. Porphyrins are macrocyclic compounds with bridges of one carbon atom joining pyrroles to form a characteristic tetrapyrrole ring structure. There are many different classes of porphyrin derivatives including those containing dihydro-pyrrole units. Chlorins, as referred to in the present invention, are porphyrin derivatives containing one dihydro-pyrrole unit whereas bacteriochlorins are characterized by two dihydro-pyrrole units (in general in chlorins one double bond of the aromatic system in β-position is absent and in bacteriochlorins two opposite double bonds are absent compared to the porphyrin). As examples of tetrapyrrolic macrocyclic compounds used as photosensitizers, Publication No US 2012/0,263,625A1 from Aicher et al. discloses glyco-substituted dihydroxy-chlorins for antibacterial PDT, U.S. Pat. No. 7,022,843 B1 from MacAlpine et al. provides β,β'-dihydroxy meso-substituted chlorins as photosensitizers, and U.S. Pat. No. 7,166,719 B2 from Pandey et al. discloses tetrapyrrole compounds containing a fluorinated substituent where the compound is a chlorin or a bacteriochlorin for PDT diagnostic and therapeutic application.

There are several properties that an effective photosensitizer should accomplish. Among them, a desirable characteristic in order to efficiently destroy deep target tissues is a strong absorption at long wavelength. Many current photosensitizers are not efficient enough as they have low absorption in the red region of the spectrum. Chlorins have the advantage that they possess an intense absorption in the red and near-infrared region of the electromagnetic spectrum. As light of longer wavelength penetrates deeper into the tissue, it is thus possible to treat e.g. more expanded tumors, if the PDT is employed for tumor therapy. Chlorins possessing potential for PDT can either be derived from natural sources or from total synthesis.

If the chlorins are derived from natural compounds they are usually obtained by derivatizing chlorophylls or bacteriochlorophylls, as for example the photosensitizers derived from chlorophyll of photosynthetic plants and algae disclosed in U.S. Pat. No. 5,330,741. Due to the sensibility of the natural compounds this is often difficult and requires vast resources. So, the synthesis of chlorins by total synthesis is an appealing alternative. Methods to prepare chlorins and bacteriochlorins by total synthesis are known in the art. Generally these compounds are prepared by first synthesizing the porphyrin and then converting the porphyrin system to a chlorin or bacteriochlorin system. This step can e.g. be performed by the reduction with in situ generated di-imine or by cis-dihydroxylation with osmium tetroxide; multistep reactions leading to trans-dihydroxylation are also known (Patent No EP 0337601 B1; Publication No WO 96/13504A1, Publication No WO 00/61584A1, Publication No US 2012/263625 A1; [4]; [5]). Mostly, compounds with four identical substituents in the meso-positions have been investigated and tested for their PDT efficacy. One prominent example is Temoporfin which is the active compound in the medicinal product Foscan® which is successfully used in Europe as a medicinal product for the PDT treatment of head and neck cancer. Also, all examples in the above-mentioned Publication No WO 96/3504A1 are compounds with four identical meso substituents. Fewer publications on unsymmetrically tetrakis-meso-substituted chlorins derived from total synthesis exist; most of them are of the so-called $A_3B$-type, i.e. incorporating 3 identical and one different meso-substituent ([6], [4]). One reason for using symmetrically substituted porphyrins to convert them into chlorins is that in this case no isomers are formed. If no isomers are formed the resulting compounds are easily characterized and prepared, a key factor for commercial production. If unsymmetrically substituted porphyrins are used to convert them into chlorins different regioisomers are formed which require subsequent separation. Sometimes, the chlorins with a meso-$A_3B$-substitution found in the art are often used as an isomeric mixture without separation (e.g. [6]).

The basic tetrapyrrole systems are usually synthesized by condensation of aldehydes and pyrrole or aldehydes and dipyrromethanes under acidic conditions. The reaction conditions as well as the properties of the reaction partners limit the variety of functional groups that can be introduced via this preparation method. Thus, either alternative synthetic methods are required for building up the basic tetrapyrrole system or alternative methods for functionalizing the final tetrapyrrole system. One of the approaches based on the latter is the nucleophilic substitution on pentafluorophenyl-substituted polypyrrolic systems (e.g. [7]). The pentafluorophenyl-residue may also be introduced into other pyrrole-based compounds, e.g. corroles ([8]; [9]). This offers the possibility of nucleophilic functionalization on these compounds.

Thus, there is a need to enhance the effectiveness of prior art biologically active compounds used as photosensitizers in order to successfully perform a wide range of light irradiation treatments such as photodynamic therapy of cancer, infections and other diseases. Moreover, it is necessary to provide novel methods of preparation and improved photosensitizers more potent than those available up to date.

For the administration of photosensitizers suitable pharmaceutical formulations are needed. In this respect, Publication No WO2011071970 by Langer et al. discloses suitable photosensitizer formulations based on poly-lactic-co-glycolic-acid (PLGA) whereas Publication No WO2011071968 by Langer et al. discloses formulations based on human serum albumin (HSA) nanoparticles. Publication No WO2005023220 by Albrecht et al. discloses suitable liposomal formulations for the photosensitizers that are subject of the present invention. Possible oral formulations for such photosensitizers are described in Publication No WO2010129337 by Graefe et al. and in Publication No WO2010129340 by Farmer et al.

OBJECTIVES AND BRIEF SUMMARY OF THE INVENTION

It is an objective of the present invention to provide biologically active compounds that can be used as photosensitizers for a wide range of applications including light irradiation treatments such as photodynamic therapy of cancer, infections and other diseases.

It is a further objective of the present invention to use the chemically stable porphyrin and chlorin derivatives for various medical applications such as photodynamic therapy.

It is another object of the present invention to provide ways for the easy further functionalization of porphyrins and chlorins with thiols, amines and specifically alcohols making use of pentafluorophenyl-substituted porphyrins.

It is another object of the present invention to use other chemically stable, pyrrole-based compounds, namely, boron-dipyrromethenes (bodipys), corroles and hexaphyrins for medical applications such as photodynamic therapy and provide ways for their functionalization with thiols, amines and specifically alcohols making use of pentafluorophenyl-residues in these compounds.

In this respect it is another object of the present invention to provide mild reaction conditions for preparing desired compounds modified at their pentafluorophenyl residues.

It is another objective of the present invention to provide unsymmetrically tetrakis-meso-substituted chlorin structures that can be used in the photodynamic therapy of tumors and other hyperproliferative diseases, dermatological disorders, viral or bacterial infections, opthamological disorders or urological disorders. It is to be understood that a light excitation of the chromophore as it is necessary for photodynamic therapy may be effected either by one or by multiphoton specifically two-photon excitation.

It is yet another object of the present invention to provide unsymmetrically tetrakis-meso-substituted chlorin structures that can be used for the fluorescence diagnosis and PDT treatment of a non-tumorous indication such as arthritis and similar inflammatory diseases.

It is still another object of the present invention to provide a method to prepare and purify such unsymmetrically tetrakis-meso-substituted chlorins.

It is still a further object of the present invention to provide amphiphilic compounds to be used in the PDT-treatment of tumors, dermatological disorders, viral or bacterial infections, opthamological disorders or urological disorders.

It is another object of the present invention to provide a method of preparation that can direct the dihydroxylation or reduction of the starting material so that the formation of one isomer is favored.

Effective photosensitizers are mostly lipophilic compounds because such compounds have a higher tendency to accumulate in cellular membrane structures. It is in these membrane structures where the reactive oxygen species generated by the photodynamic treatment can effectively damage the (tumor) cells. However, due to their lipophilic nature photosensitizers are sparingly or not at all water soluble so suitable pharmaceutical formulations are needed for their clinical application. Such pharmaceutical formulations may involve liposomal, nanoparticular or polymer-based formulations. For increasing patient compliance during treatment improved formulations of photosensitizers e.g. oral formulations are needed.

Therefore, it is still another objective to provide pharmaceutically acceptable formulations for the biologically active compounds of the present invention such as liposomal or nanoparticular formulations to be injected avoiding undesirable effects like precipitation at the injection site or delayed pharmacokinetics of the tetrapyrrole systems.

Briefly stated, the present invention provides biologically active compounds that can be used as photosensitizers for diagnostic and therapeutic applications, particularly for PDT of cancer, infections and other hyperproliferative diseases, fluorescence diagnosis and PDT treatment of a non-tumorous indication such as arthritis, inflammatory diseases, viral or bacterial infections, dermatological, opthamological or urological disorders as well as providing methods to obtain them in pharmaceutical quality. One embodiment consists of a method to synthesize a thiolo-, alkoxy- or amino-substituted porphyrin with a specific arrangement of hydroxyl groups in the periphery. Another embodiment consists of a method to synthesize a porphyrin with a defined arrangement of meso-substituents and then converting this porphyrin system to a chlorin system by dihydroxylation or reduction. In another embodiment the substituents on the porphyrin are selected to direct the reduction or dihydroxylation to the chlorin so that a certain isomer is selectively formed. Another embodiment is to provide amphiphilic compounds with a higher membrane affinity and increased PDT-efficacy. In another embodiment substituents are identified that via their steric and/or electronic influence direct the dihydroxylation or reduction with diimine so that one isomer is favored. Another embodiment consists of formulate the desired isomer into a liposomal formulation to be injected avoiding undesirable effects like solubility problems at injection or delayed pharmacokinetics of the tetrapyrrole systems.

The above and other objects, features and advantages of the present invention will become apparent from the following description read in conjunction with the accompanying drawings.

BRIEF DESCRIPTION OF FIGURES

FIG. 1A and 1B shows examples of specifically tetrakis-meso-substituted porphyrin and chlorin structures containing pentafluorophenyl residues that have further been functionalized with thiols, amines or alcohols.

FIG. 2A and 2B shows examples of suitably substituted porphyrins which can be used to obtain the desired photoactive compounds of the present invention.

DETAILED DESCRIPTION OF PREFERRED EMBODIMENTS

In the present invention symmetrical and unsymmetrical porphyrins and chlorins are disclosed which carry specific substituents ensuring a high PDT activity. For their synthesis these compounds partly rely on the methods already disclosed by us in Publication No US 2012/0,263,625A1 from Aicher et al. (Glyco-substituted dihydroxy-chlorins and b-functionalized chlorins for anti-microbial photodynamic therapy) and Publication No US 2011/0,206,613A1 from Wiehe et al. (Method and application of unsymmetrically meso-substituted porphyrins and chlorins for PDT).

As described further below, the currently preferred embodiments provide biologically active compounds that can be used as photosensitizers for a wide range of light irradiation treatments such as photodynamic therapy of cancer, hyperproliferative diseases, dermatological disorders, viral or bacterial infectious diseases, ophthalmological disorders and/or urological disorders. The alternative photosensitizers provided herein have the advantage that they are easily produced and characterized. Moreover, since preferred embodiments provide methods to tailor amphiphilic compounds for desired PDT applications, target tissue selectivity is increased and thus PDT efficacy. The compounds as described further below enhance the effectiveness of prior art biologically active compounds offering a deeper tissue penetration due to their strong absorption at long wavelength of the red and near-infrared region of the electromagnetic spectrum, and provide enhanced selectivity for target tissues over healthy surrounding tissues due to its tailored amphiphilicity and custom-made pharmacokinetic behavior depending on the particular PDT application. For that end, preferred embodiments make use of the functionalization of pentafluorophenyl-substituted porphyrins with thiols, amines or alcohols and their subsequent conversion to chlorins or dihydroxy-chlorins. By this the preferred embodiments in addition solve the problem that known porphyrins functionalized at their pentafluorophenyl residues are far too lipophilic to be useful for biomedical applications.

Figure 1A:
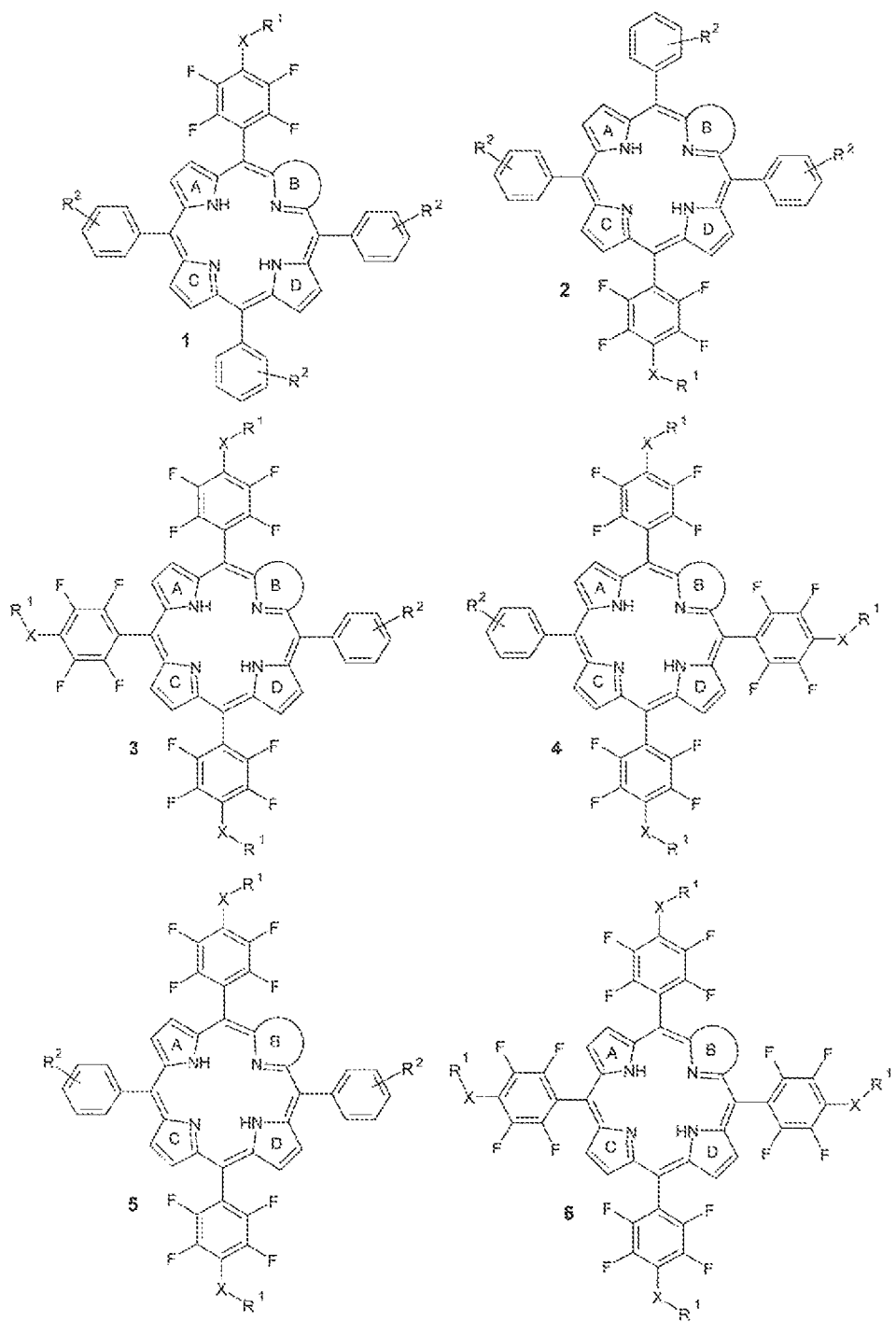

The biologically active compounds of present embodiments that are advantageously useful for different medical indications, particularly PDT, are tetrakis-meso-substituted porphyrin and chlorin structures. Indeed, it has been unexpectedly found that porphyrins and chlorins containing a pentafluorophenyl residue in at least one of their meso positions which has subsequently been modified with certain short-chain thiols, amines or alcohols carrying at least two additional hydroxyl groups, as illustrated in FIGS. 1A and 1B, are especially suited for such a medical application, i.e. because they increase the solubility of these compounds and allow for a tailored amphiphilicity increasing the interaction with cellular membrane structures which is one aspect important for PDT. Additionally, in another embodiment present compounds extend their applications to fluorescence diagnosis and PDT treatment of a non-tumorous indication such as arthritis and similar inflammatory diseases, as it is known that photosensitizers also tend to accumulate in inflammatory tissues.

Figure 2B:
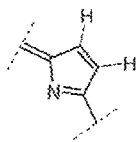

Preferred embodiments provide specifically tetrakis-meso-substituted tetrapyrrole compounds and methods of preparation in order to provide improved photosensitizers more potent than those available up to date. Thus, PDT efficacy is increased by taking advantage of the properties of these specifically unsymmetrically tetrakis-meso-substituted chlorins, such as strong absorption at long wavelength of the red and near-infrared region of the electromagnetic spectrum for deeper tissue penetration, enhanced selectivity for tumors or other target tissues over healthy surrounding tissues due to its tailored amphiphilicity that increases membrane affinity, and custom-made pharmacokinetic behavior depending on the particular PDT application. In the present invention it was inadvertently found that when polypyrrolic systems are reacted with certain short chain alcohols compounds with an unusually high PDT activity are obtained which render these systems specifically suitable for photomedical applications In order to obtain the novel photosensitizers some embodiments uses the chemically stable tetrapyrrole derivatives according to formulae 1, 2, 3, and 4 shown in FIGS. 2A and 2B and provides methods to further functionalize them at their pentafluorophenyl residues by nucleophilic substitution with thiols, amines or alcohols [7]. In some cases the conditions used to effect the nucleophilic substitution serve also to remove protection groups at the non-fluoro-substituted meso-residues. In addition it is shown how these thio-, amino- or alkoxy-modified compounds can further be converted to simple chlorins or dihydroxy-chlorins. Meso-alkyl substituted chlorins, more particularly the unsymmetrically tetrakis-meso-substituted chlorin structures that can be used in the photodynamic therapy (Patent No EP 00337601B1; Publication No WO 96/13504A1, Publication No WO 00/61584A1; [4]; [5]). The attractiveness of substituted chlorins resides in that different substitutions pattern might increase the amphiphilicity of the compounds and thus their membrane affinity and PDT efficacy.

Fluorine-substituted pharmaceuticals may be detected in vivo by magnetic resonance techniques. Fluorine-substituted photosensitizers may be used for such MR-assisted detection and imaging [10]. Therefore, it is another objective of the present invention to provide improved photosensitizers that can be detected in vivo via magnetic resonance techniques.

Apart from certain photophysical properties it is generally accepted that photosensitizers should also possess a suitable degree of polarity or amphiphilicity to be effective in PDT. However, not all photosensitizers with a polar or amphiphilic substitution are in fact suitable as photosensitizers for PDT. In the investigations related to present embodiments it has surprisingly been found, that a specific substitution which can be accomplished by modifying the pentafluorophenyl substituent with certain short chain alcohols, aminoalcohols or hydroxyl-substituted thiols leads to compounds which are especially suitable as photosensitizers. Whereas on the other hand it is shown that compounds lacking this specific substitution are less effective as photosensitizers.

For their synthesis these compounds partly rely on the methods already disclosed by us in Publication No US 2012/0,263,625A1 from Aicher et al. (and Publication No US 2011/0,206,613A1 from Wiehe et al.

In one embodiment, a method to synthesize porphyrins with a defined arrangement of meso-substituents is provided [porphyrins of the $A_2B_2$ type, either with a 'cis' or a 'trans' arrangement of the meso-substituents, or of the $A_3B$ type, all of them containing pentafluorophenyl residues], modifying them at their pentafluorophenyl residues with said short chain alcohols or aminoalcohols and then converting these porphyrin systems to the corresponding chlorin systems by dihydroxylation or reduction (as e.g. described in: Publication No US 2011/0,206,613A1 from Wiehe et al.; [11]). In another embodiment, the dihydroxylation is performed on an $A_3B$ or an $A_2B_2$ porphyrin with cis-arrangement of the substituents, so isomers are formed. The advantage in this case is that the pentafluorophenyl residue exerts a directive influence favoring specific of the possible isomers. In cases where isomers are possible the dihydroxylation is preferred at the pyrrole ring closer to the pentafluorophenyl-residue. This can be seen in example 3.3 where only the favored isomer was found.

Another embodiment consists of the steps of synthesizing a porphyrin with a defined arrangement of substituents, containing modified pentafluorophenyl residues, and then formulating it into a liposomal formulation.

In yet another embodiment, a porphyrin of the 'trans'-$A_2B_2$-type, containing modified pentafluorophenyl residues, is synthesized, converted to the dihydroxychlorin and purified by chromatography. In this case no diastereomers are formed (only an enantiomeric mixture).

In yet another embodiment, a tetrakis-pentafluorophenyl-substituted porphyrin is synthesized and converted to the corresponding chlorin systems by dihydroxylation or reduction.

In a specifically preferred embodiment, a porphyrin of the 'trans'-$A_2B_2$-type is synthesized, having 3-hydroxyphenyl as substituent A and 4-(2,3-dihydroxypropyloxy)-2,3,5,6-tetrafluorophenyl residues as substituent B. This porphyrin was converted to the chlorin and the dihydroxychlorin.

In another specifically preferred embodiment, a porphyrin of the $A_3B$-type is synthesized, having 3-hydroxyphenyl as substituent A and 4-(2,3-dihydroxypropyloxy)-2,3,5,6-tetrafluorophenyl residues as substituent B. This porphyrin was converted to the chlorin and the dihydroxychlorin.

In yet another specifically preferred embodiment, a porphyrin of the $A_4$-type is synthesized, having 4-(2,3-dihydroxypropyloxy)-2,3,5,6-tetrafluorophenyl residues as substituent A. This porphyrin was converted to the chlorin and the dihydroxychlorin.

In yet another preferred embodiment, a boron-dipyrromethene (bodipy) is synthesized having a 4-(2,3-dihydroxypropyloxy)-2,3,5,6-tetrafluorophenyl residue as a substituent.

In yet another preferred embodiment bodipys and corroles carrying dihydroxyaminopropyl substituents are synthesized.

In the case of $A_2B_2$ and $A_3B$-substituted porphyrins and chlorins or $A_2B$-substituted corroles there is a substituent ("B") which has not been modified with certain short-chain thiols, amines or alcohols carrying at least two additional hydroxyl groups as described above. This substituent B may be chosen from a wide variety of possible substituents (as exemplified in FIGS. 1A, 1B, 2A and 2B for porphyrins and chlorins). In specifically preferred embodiments this substituent carries OH- or COOH-groups.

Acceptable starting materials for the synthesis of the unsymmetrical porphyrins and chlorins which are one subject of the present embodiments are pyrrole and aldehydes. More specifically, pyrrole and two aldehydes, pentafluorobenzaldehyde and another aromatic aldehyde are employed for the synthesis of the unsymmetrically substituted porphyrins. Pyrrole and aldehydes are subjected to a condensation reaction. Suitable methods for this condensation have long been known in the art [12]. Alternatively, the unsymmetrically substituted porphyrins can also be synthesized using di- or tripyrromethanes and aldehydes, as is also known in the art [13]. After condensation and purification the desired unsymmetrically substituted porphyrins are modified at their pentafluorophenyl residues via treatment with thiols, aminoalcohols or alcohols, if necessary in the presence of an additional base and/or using protection groups. If two or more nucleophilic groups are present in the thiol, aminoalcohol or alcohol such a use of protection groups may be necessary to avoid the formation of inseparable mixtures. Therefore certain embodiments of the present invention take advantage of the use of protection groups to ensure a product with suitable purity for pharmaceutical use. After purification of the modified porphyrins, these are converted to the chlorins.

Figure 3:
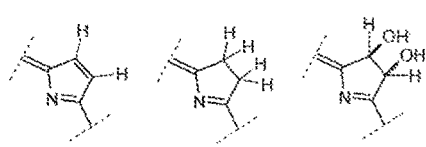
FIG. 3 depicts an embodiment of the present invention showing a specifically substituted porphyrin and two chlorins.
Figure 3:
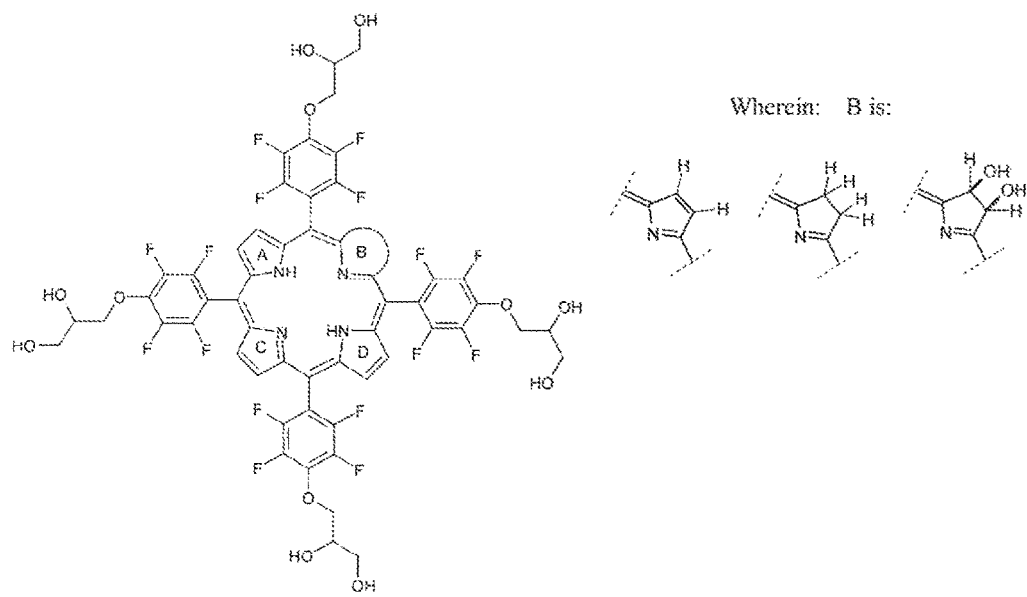

For symmetrically substituted porphyrins (i.e. $A_4$-type porphyrins) only pyrrole and pentafluorobenzaldehyde are employed for the condensation. The modification of the pentafluorophenyl residues and the conversion of the modified porphyrins to the chlorins can then be accomplished as described above. Thus, compounds as depicted in FIG. 3 can be obtained.

The dihydroxylation of porphyrins with osmium tetroxide that is known in the art uses gaseous $H_2S$ to reductively cleave the osmate(VI)ester. The present invention uses a simpler method for the reductive cleavage of the osmate (VI)ester that avoids the use of gaseous $H_2S$. Instead, a small amount of a saturated sodium bisulfite solution in $H_2O$/MeOH is used which is added to the reaction mixture. After stirring the mixture overnight the cleavage of the osmate ester to the diol proceeds quantitatively (examples 3.1 to 3.3).

The synthesis of the basic skeleton of the other pyrrole-based compounds used in the present embodiments (pentafluorophenyl-substituted corroles, hexaphyrins) can be accomplished by methods known in the art ([8], [9]). Examples for their nucleophilic substitution at their pentafluorophenyl residues are given in examples (5.1 and 6.1).

The use of specifically substituted amphiphilic porphyrin and chlorin derivatives produced herein is suitable to be used for photodynamic therapy of cancer and other hyperproliferative diseases and infections.

The use of specifically substituted pyrrole-based compounds (bodipys, corroles, hexaphyrins) produced herein is suitable to be used for photodynamic therapy of cancer and other hyperproliferative diseases and infections.

In another embodiment, pharmaceutically acceptable formulations are provided for the biologically active compounds described herein, such as liposomal or nanoparticular formulations, to be injected avoiding undesirable effects like precipitation at the injection site or delayed pharmacokinetics of the tetrapyrrole systems. Other nanoparticular formulations suitable as carrier systems for the present invention are Human Serum Albumin (HSA) or poly(lactic-co-glycolic acid) (PLGA) particles.

PDT is accomplished by first incorporating the derivatives into a pharmaceutically acceptable application vehicle (e.g. ethanolic solution, liposomal formulation or a formulation based on Human Serum Albumin (HSA) or poly(lactic-co-glycolic acid) (PLGA) particles) for delivery of the derivatives to a specific treatment site. After administering the derivatives in the vehicle to a treatment area, sufficient time is allowed so that the porphyrin and chlorine derivatives preferentially accumulate in the diseased tissue. Lastly, the treatment area is irradiated with light of a proper wavelength and sufficient power to activate the porphyrin derivatives to induce necrosis or apoptosis in the cells of said diseased tissue. Thus, one of the main advantages is that convenient pharmaceutical formulations can be created for the biologically active compounds described herein, such as liposomal formulation to be injected avoiding undesirable effects like precipitation at the injection site or delayed pharmacokinetics of the tetrapyrrole systems. Due to their amphiphilic nature, the chemically stable porphyrin and chlorin derivatives can be prepared in pharmaceutically acceptable and active preparations for different administration methods, e.g. injections or oral formulations as tablets. In a specifically preferred embodiment such amphiphilic compounds are formulated into liposomes. Such liposomal formulations of the photosensitizers can be prepared in analogy to the procedure described in the U.S. Pat. No. 7,354,599 B2 by V. Albrecht, A. Fahr et al.

The liposomal formulations of the photosensitizers can be used to e.g. influence the pharmacokinetics of photosensitizer absorption and distribution and increase the bioavailability.

Determination of dark toxicity (DT) and phototoxicity of derivatives prepared according to the present embodiments (examples 1.1 to 3.3), in cell culture experiments with different cell lines showed the excellent properties of the compounds for use in PDT (e.g. examples 7.1 to 7.5). Further examples of the good phototoxic properties of the compounds are illustrated with examples 7.6 to 7.10. More examples illustrating the good phototoxic properties of compounds prepared according to the present invention are given in the examples 7.18 to 7.24. Their synthesis is described in example 1.5. The additional examples 7.11 to 7.17 of experiments in the HT 29 (human colon adenocarcinoma) cell line and other cell lines are included to illustrate that compounds which do not possess a combination and arrangement of substituents as the one favored in the present invention show a less promising PDT activity.

The following examples are presented to provide those of ordinary skill in the art with a full and illustrative disclosure and description of how to make the specifically substituted chlorin derivatives and show their photodynamic activity and are not intended to limit the scope of what the inventor regards as the invention. Efforts have been made to ensure accuracy with respect to numbers used (e.g. amounts, temperature etc.), but some experimental errors and deviations should be accounted for. Also, best measures have been taken to name the compounds with their systematic IUPAC name, nevertheless the basic reference are the given structural formulas based on the experimental spectroscopic data.

EXAMPLES

All reagents were used as purchased from commercial suppliers. Dichloromethane (DCM) was purified by distillation from $K_2CO_3$ prior to use. Thin layer chromatography (TLC) was performed using Merck silica gel 60 (without fluorescence indicator) pre-coated on aluminium sheets. Flash chromatography was carried out using Merck silica gel 60, 0.040-0.063 mm (230-400 mesh). $^1H$ and $^{13}C$ NMR spectra were recorded in $CDCl_3$, $(CD_3)_2CO$ or $(CD_3)_2SO$ on Bruker AC 250, AC 500 or AMX 500 instruments. Chemical shifts δ are given in ppm relative to TMS as internal standard or relative to the resonance of the residual solvent peak, J values are given in Hz. Mass spectra were recorded on Varian MAT 771, Varian IonSpec QFT-7 or Agilent 6210 ESI-TOF instruments. Electronic absorption spectra were recorded on a Specord S300 (Analytik Jena) spectrophotometer using DCM or acetone as solvent.

Example 1

Preparation of 2,3-Dihydroxy-Propyloxy-Substituted Porphyrins and Dihydroxyprop-Ylamino-Substituted Porphyrins

1.1.1 Preparation of 5,10,15,20-tetrakis(pentafluorophenyl)-porphyrin

In a typical experiment, dry DCM (1500 ml) was placed in a three-necked flask equipped with a magnetic stirrer and argon gas inlet. After pyrrole (0.88 ml, 12.7 mmol) and pentafluorobenzaldehyde (1.58 ml, 12.7 mmol) were added, the flask was shielded from ambient light and $BF_3(OEt_2)$ (0.45 ml, 3.6 mmol) was added and the reaction mixture was stirred at room temperature for 18 h. Then, DDQ (2.90 g, 12.8 mmol) suspended in dry DCM (100 ml) was added, the mixture was refluxed for 2 hours, after cooling down to room temperature filtered over silica and the solvent was evaporated. After column chromatography (DCM/hexane=1:11) and recrystallization (DCM/MeOH) the product was obtained as purple crystals (1.23 g, 1.26 mmol, 40%).

$^1$H-NMR (250 MHz, $CDCl_3$): δ=−2.92 (s, 2H, NH), 8.92 (s, 8H, β-$H_{Pyrrol}$) ppm.

$^{19}$F-NMR (376 MHz, $CDCl_3$): δ=−136.4 (dd, J=23.4, 7.7 Hz, 8F, Ar—$F_{ortho}$)), −151.10 (t, J=20.8 Hz, 4F, Ar—$F_{para}$), −161.20 (td, J=22.9, 7.6 Hz, 8F, Ar—$F_{meta}$).

HRMS (ESI-TOF): m/z calc. for $C_{44}H_{11}F_{20}N_4$ [M+H]$^+$: 975.0659; found: 975.0624.

1.1.2 Preparation of 5,10,15,20-tetrakis[2,3,5,6-tetrafluoro-4-(2,3-dihydroxypropyloxy)-phenyl]-porphyrin In a typical experiment, tetrakis(pentafluorophenyl)porphyrin (215 mg, 0.22 mmol) was dissolved in dry DMSO (4.0 ml) under argon atmosphere, KOH (210 mg, 3.74 mmol) and solketal (1.0 ml, 8.06 mmol) were added and the reaction mixture stirred under room temperature for 2 hours. After aqueous workup, extraction with ethyl acetate and drying with $Na_2SO_4$, the crude product was purified by column chromatography (DCM/ethyl acetate=85:15) and recrystallized (acetone/hexane) to obtain the protected precursor as a purple solid. The solid was afterwards dissolved in a mixture of THF (20 ml) and MeOH (30 ml), TFA (5 ml) and HCl (25%, 4 ml) were added and the mixture stirred for 2 h at room temperature. After aqueous workup, extraction with ethyl acetate and drying with $Na_2SO_4$, the crude product was purified by reversed phase column chromatography (MeOH/ethyl acetate=85:15) and recrystallized (acetone/hexane) to obtain the product as a purple solid (145 mg, 114.8 μmol, 52%).

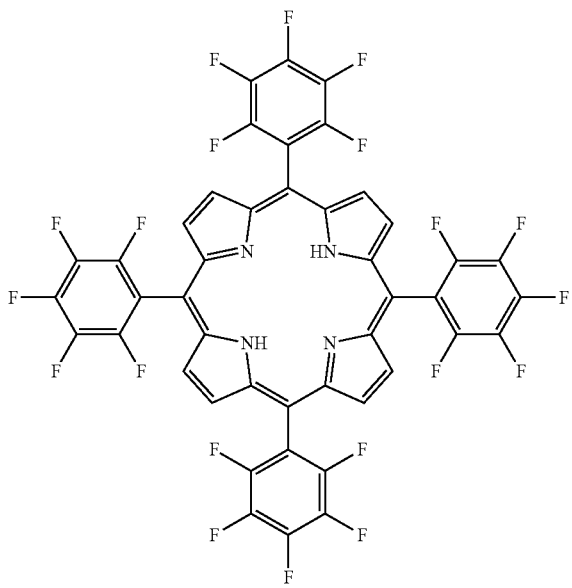 [SMILES: Fc1c(F)c(F)c(-c2c3nc(c(-c4c(F)c(F)c(F)c(F)c4F)c4ccc([nH]4)c(-c4c(F)c(F)c(F)c(F)c4F)c4nc(c(-c5c(F)c(F)c(F)c(F)c5F)c5ccc2[nH]5)C=C4)C=C3)c(F)c1F]

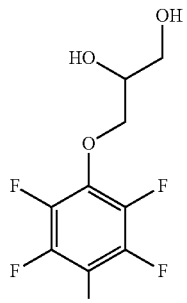

5,10,15,20-tetrakis[2,3,5,6-tetrafluoro-4-(2,3-dihydroxypropyloxy)-phenyl]-porphyrin -continued

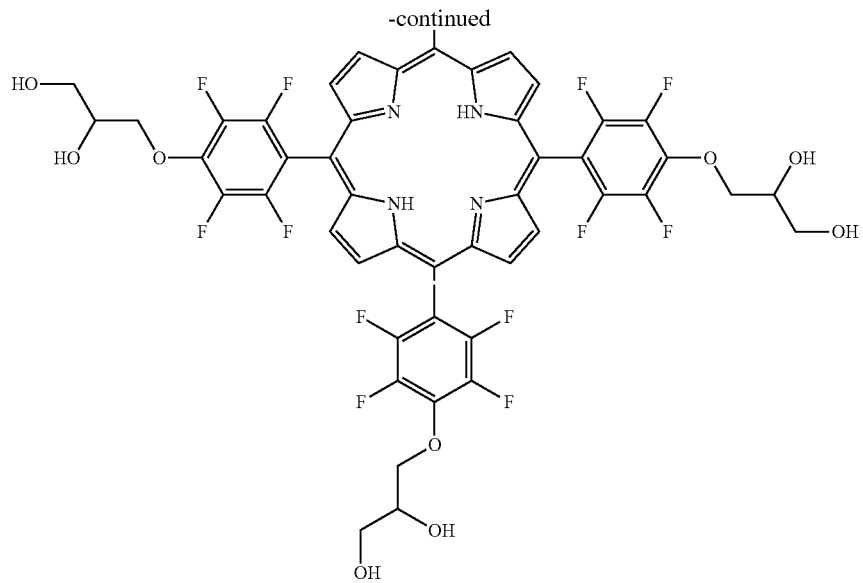

¹H-NMR (500 MHz, acetone-$d_6$): δ=−2.89 (s, 2H, NH), 3.79-3.87 (m, 8H, $OCH_2$), 3.99 (t, J=5.7 Hz, 4H, β-OH), 4.20-4.25 (m, 4H, $OCH_2CH$), 4.39 (d, J=5.3 Hz, 4H, γ-OH), 4.62 (dd, J=10.2, 6.2 Hz, 4H, $Ar_F$—$OCH_2$), 4.74 (dd, J=10.1, 4.3 Hz, 4H, $Ar_F$—$OCH_2$), 9.30 (s, 8H, β-$H_{Pyrrole}$) ppm.

¹³C-NMR (126 MHz, acetone-$d_6$): δ=62.9 ($OCH_2$), 63.0 ($OCH_2$), 71.2 ($OCH_2CH$), 71.3 ($OCH_2CH$), 76.7 ($Ar_F$—$OCH_2$), 104.6 ($Ar_F$—$C_{meso}$), 113.4 ($Ar_F$—$C_{ipso}$), 139.5 (t, $^2J_{C-F}$=12.1 Hz, $Ar_F$—$C_{para}$), 141.4 (dd, $^{1,2}J_{C-F}$=246.6, 15.2 Hz, $Ar_F$—$C_{meta}$), 146.9 (d, $^2J_{C-F}$=243.8 Hz, $Ar_F$—$C_{ortho}$) ppm.

¹⁹F-NMR (376 MHz, acetone-d6): δ=−141.72 (dd, J=23.0 Hz, 2F, Ar—$F_{ortho}$), −158.53 (dd, J=23.1 Hz, Ar—$F_{meta}$) ppm.

HRMS (ESI-TOF): m/z calc. for $C_{56}H_{39}F_{16}N_4O_{12}$ [M+H]⁺: 1263.2309; found: 1263.2233.

UV-VIS (DCM), $\lambda_{max}$ [log ε(L·mol⁻¹·cm⁻¹)]: 413 (3.99), 508 (3.85), 584 (3.41) nm.

1.2.1 Preparation of 5-(pentafluorophenyl)dipyrromethane

In a typical experiment, a round bottom flask was loaded with pyrrole (150 ml, 2.16 mol) and pentafluorobenzaldehyde (7.30 ml, 0.059 mol), TFA (0.45 ml, 5.84 mmol), was added and the mixture stirred for 20 minutes at room temperature. Afterwards, the excess pyrrole was evaporated under reduced pressure at 60° C. and the resulting oil purified by column chromatography (DCM/hexane=1:11) and recrystallyzation (DCM/pentane) to obtain a pale white solid (12.8 g, 0.041 mol, 70%).

5-(Pentafluorophenyl)dipyrromethane

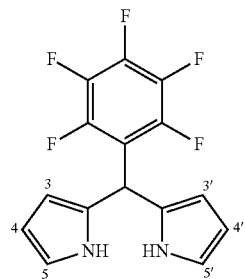 [SMILES: Fc1c(F)c(F)c(C(c2ccc[nH]2)c2ccc[nH]2)c(F)c1F]

¹H-NMR (400 MHz, acetone-$d_6$): δ=2.84 (s, 1H, CH), 5.90 (m, 2H, 3,3'-$H_{Pyrrol}$), 5.99 (m, 2H, 4,4'-$H_{Pyrrol}$), 6.68-6.71 (m, 2H, 5,5'-$H_{Pyrrol}$) ppm.

¹⁹F-NMR (376 MHz, acetone-$d_6$): δ=−143.12 (dd, J=23.0, 7.7 Hz, 2F, Ar—$F_{ortho}$), −159.57 (t, J=20.7 Hz, 1F, Ar—$F_{para}$), −164.75 (td, J=21.0, 7.0 Hz, 2F, Ar—$F_{meta}$) ppm.

1.2.2 Preparation of 5,15-bis(3-acetoxyphenyl)-10,20-bis(pentafluorophenyl)-porphyrin In a typical experiment, dry DCM (500 ml) was placed in a three-necked flask equipped with a magnetic stirrer and argon gas inlet. After 3-acetoxybenzaldehyde (0.38 ml, 2.0 mmol) and pentafluorophenyl-dipyrromethane (625 mg, 2.0 mmol) were added, the flask was shielded from ambient light. Trifluoroacetic acid (0.077 ml, 1.0 mmol) was added and the reaction mixture was stirred at room temperature for 18 h. Then, DDQ (0.70 g, 0.3 mmol) suspended in dry DCM (50 ml) was added, the mixture was stirred for 2 hours. Triethylamine (0.7 ml, 5.0 mmol) was added and after 15 min. the mixture filtered over silica and the solvent evaporated. After column chromatography (DCM/ethyl acetate=99:1) and recrystallization (DCM/hexane) the product was obtained as purple crystals (130 mg, 142 μmol, 28%).

5,15-Bis(3-acetoxyphenyl)-10,20-bis(pentafluorophenyl)-porphyrin

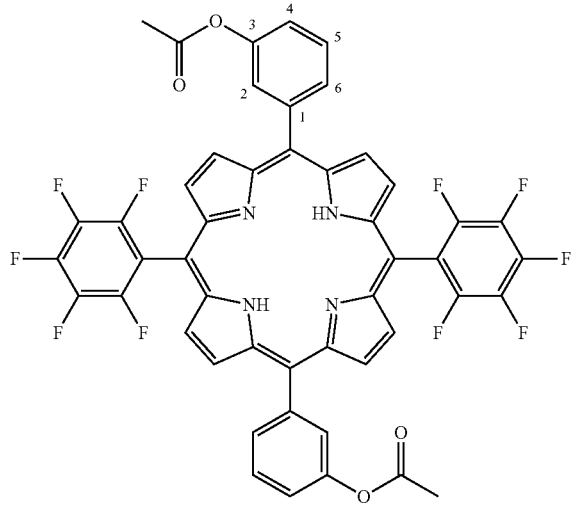 [SMILES: CC(=O)Oc1cccc(-c2c3nc(c(-c4c(F)c(F)c(F)c(F)c4F)c4ccc([nH]4)c(-c4cccc(OC(C)=O)c4)c4nc(c(-c5c(F)c(F)c(F)c(F)c5F)c5ccc2[nH]5)C=C4)C=C3)c1]

¹H-NMR (400 MHz, acetone-$d_6$): δ=−2.87 (s, 2H, NH), 2.41 (s, 6H, $CH_3$), 7.58 (dd, J=8.2 Hz, 1.7 Hz, 2H, Ar—H-6), 7.80 (t, J=7.8 Hz, 2H, Ar—H-5), 7.99 (d, J=4.8 Hz, 2H, Ar—H-2), 8.11 (d, J=7.5 Hz, 2H, Ar—H-4), 8.84 (d, J=4.8 Hz, 4H, 2,8,12,18-β-$H_{Pyrrole}$), 9.04 (d, J=4.8 Hz, 4H, 3,7,13,17-β-$H_{Pyrrole}$) ppm.

¹³C-NMR: (126 MHz, acetone-$d_6$): δ=21.4 ($CH_3$), 102.5 ($Ar_F$—$C_{ipso}$), 120.3 ($Ar_F$—$C_{meso}$), 121.6 (Ar—C-6), 128.0 (Ar—C-5), 128.2 (Ar—C-2), 132.3 (Ar—C-4), 142.6 (Ar—$C_{ipso}$), 145.7 ($Ar_F$—$C_{meta}$), 147.7 ($Ar_F$—$C_{ortho}$), 149.5 (Ar—C-3), 169.8 (C=O) ppm.

¹⁹F-NMR (376 MHz, acetone-$d_6$): δ=−136.59--−136.75 (m, 4F, Ar—$F_{meta}$), −151.91--−152.11 (m, 2F, Ar—$F_{para}$), −161.65--−161.85 (m, 2F, Ar—$F_{ortho}$) ppm.

1.2.3 Preparation of 5,15-bis(3-hydroxyphenyl)-10,20-bis[2,3,5,6-tetrafluoro-4-(2,3-dihydroxypropyloxy)-phenyl]porphyrin In a typical experiment, 5,15-bis(3-acetoxyphenyl)-10,20-bis(pentafluorophenyl)-porphyrin (530 mg, 0.582 mmol) was dissolved in a two-necked round bottom flask with dry DMSO (10 ml) under argon atmosphere, KOH (1.5 g, 26.7 mmol) and solketal (8.0 ml, 61.3 mmol) were added and the reaction mixture stirred under room temperature for 30 minutes. After aqueous workup, extraction with ethyl acetate and drying with $Na_2SO_4$, the crude product was evaporated to dryness. Then, the solid was afterwards dissolved in a mixture of THF (30 ml) and MeOH (30 ml), TFA (10 ml) and HCl (25%, 7.5 ml) were added and the mixture stirred for 2 h at room temperature. After aqueous workup, extraction with ethyl acetate and drying with $Na_2SO_4$, the crude product was purified by reversed phase column chromatography (MeOH/ethyl acetate=3:17) and recrystallized (acetone/hexane) to obtain the product as a purple solid (410 mg, 114.8 μmol, 72%).

5,15-Bis(3-hydroxyphenyl)-10,20-bis[2,3,5,6-tetrafluoro-4-(2,3-dihydroxypropyloxy)-phenyl]porphyrin

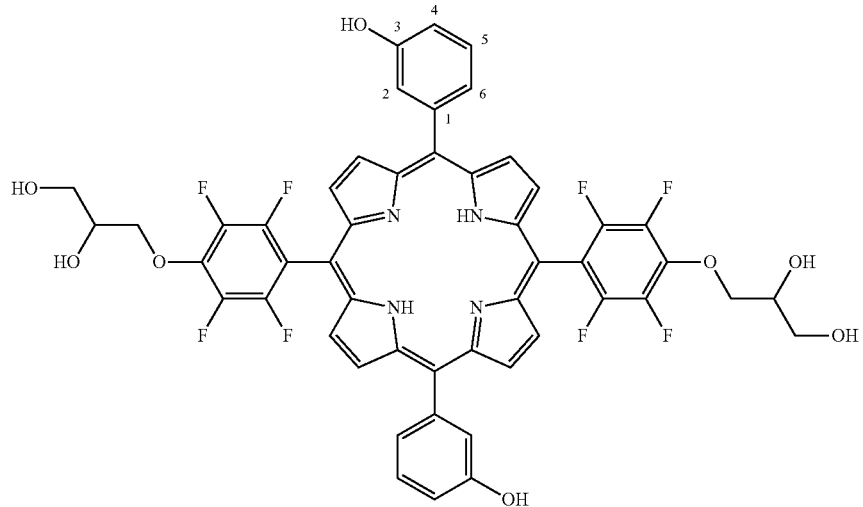 [SMILES: OCC(O)COc1c(F)c(F)c(-c2c3nc(c(-c4cccc(O)c4)c4ccc([nH]4)c(-c4c(F)c(F)c(OCC(O)CO)c(F)c4F)c4nc(c(-c5cccc(O)c5)c5ccc2[nH]5)C=C4)C=C3)c(F)c1F]

¹H-NMR (500 MHz, acetone-$d_6$): δ=−2.83 (s, 2H, NH), 3.7-3.89 (m, 4H, $OCH_2$), 3.99 (t, J=5.7 Hz, 1H, β-OH), 4.19-4.26 (m, 2H, $OCH_2CH$), 4.38 (d, J=5.3 Hz, 1H, γ-OH), 4.62 (dd, J=10.2, 6.2 Hz, 1H, $Ar_F$—$OCH_2$), 4.73 (dd, J=10.2, 4.4 Hz, 1H, $Ar_F$—$OCH_2$), 7.33-7.36 (m, 3H, Ar—H-6), 7.62-7.66 (m, 3H, Ar—H-5), 7.73-7.79 (m, 6H, Ar—H-2+Ar—H-4), 8.92 (s, 3H, Ar—OH), 8.96-9.22 (m, 8H, β-$H_{Pyrrole}$) ppm.

¹³C-NMR (126 MHz, acetone-$d_6$): δ=63.0 ($OCH_2$), 71.3 ($OCH_2CH$), 76.7 (t, $^4J_{C-F}$=3.1 Hz, $Ar_F$—$OCH_2$), 103.3 ($Ar_F$—$C_{meso}$), 114.1 (t, $^3J_{C-F}$=19.9 Hz, $Ar_F$—$C_{ipso}$), 115.3 (Ar—C-6), 121.2 (Ar—$C_{meso}$), 122.1 (Ar—C-2), 126.5 (Ar—C-4), 127.9 (Ar—C-5), 139.3 ($Ar_F$—$C_{para}$), 141.4 (d, $^1J_{C-F}$=245.9 Hz, $Ar_F$—$C_{meta}$), 142.5 (Ar—$C_{ipso}$), 146.9 (d, $^1J_{C-F}$=237.2 Hz, $Ar_F$—$C_{ortho}$), 156.0 (Ar—C-3) ppm.

¹⁹F-NMR (376 MHz, acetone-$d_6$): δ=−141.90--−142.12 (m, 2F, Ar—$F_{ortho}$), −158.81--−159.01 (m, 2F, Ar—$F_{ortho}$) ppm.

HRMS (ESI-TOF): m/z calc. for $C_{50}H_{35}F_8N_4O_8$ [M+H]$^+$: 971.2327; found: 971.2336.

UV-VIS (MeOH), $\lambda_{max}$[log ε(L·mol$^{-1}$·cm$^{-1}$)]: 414 (5.31), 511.5 (4.18), 545 (3.47), 588 (3.57), 643 (3.12) nm.

1.3.1 Preparation of 5,10,15-tris(3-acetoxyphenyl)-20-(pentafluorophenyl)-porphyrin In a typical experiment, dry DCM (1500 ml) was placed in a three-necked flask equipped with a magnetic stirrer and argon gas inlet. After pyrrole (1.04 ml, 15.04 mmol), 3-acetoxybenzaldehyde (1.58 ml, 11.26 mmol) and pentafluorobenzaldehyde (0.47 mg, 3.81 mmol) were added, the flask was shielded from ambient light. Trifluoroacetic acid (1.16 ml, 15.06 mmol) was added and the reaction mixture was stirred at room temperature for 18 h. Then, DDQ (2.70 g, 11.89 mmol) suspended in dry DCM (50 ml) was added, the mixture was stirred for 2 hours. Triethylamine (2.30 ml, 16.49 mmol) was added and after 15 min. the mixture filtered over silica and the solvent evaporated. After column chromatography (DCM/ethyl acetate=99:1) and recrystallization (DCM/hexane) the product was obtained as purple crystals (242 mg, 275 μmol, 8%).

5,10,15-Tris(3-acetoxyphenyl)-20-(pentafluorophenyl)-porphyrin

1.3.2 Preparation of 5,10,15-tris(3-hydroxyphenyl)-20-[2,3,5,6-tetrafluoro-4-(2,3-dihydroxypropyloxy)-phenyl]-porphyrin In a typical experiment, 5,10,15-tris(3-acetoxyphenyl)-20-(pentafluorophenyl)-porphyrin (72.5 mg, 82.5 μmol) was dissolved in dry DMSO (4.0 ml) under argon atmosphere, KOH (0.20 g, 3.56 mmol) and solketal (0.8 ml, 6.45 mmol) were added and the reaction mixture stirred under room temperature for 30 minutes. After aqueous workup, extraction with ethyl acetate and drying with $Na_2SO_4$, the crude product was purified by column chromatography (DCM/ethyl acetate=85:15) and recrystallized (acetone/hexane) to obtain a purple solid. Then, the solid was afterwards dissolved in a mixture of THF (4 ml) and MeOH (5 ml), TFA (2 ml) and HCl (25%, 1.5 ml) were added and the mixture stirred for 2 h at room temperature. After aqueous workup, extraction with ethyl acetate and drying with $Na_2SO_4$, the crude product was purified by reversed phase column chromatography (MeOH/$H_2O$=95:5) and recrystallized (acetone/hexane) to obtain the product as a purple solid (48.2 mg, 58.7 μmol, 70%).

5,10,15-Tris(3-hydroxyphenyl)-20-[2,3,5,6-tetrafluoro-4-(2,3-dihydroxypropyloxy)-phenyl]-porphyrin

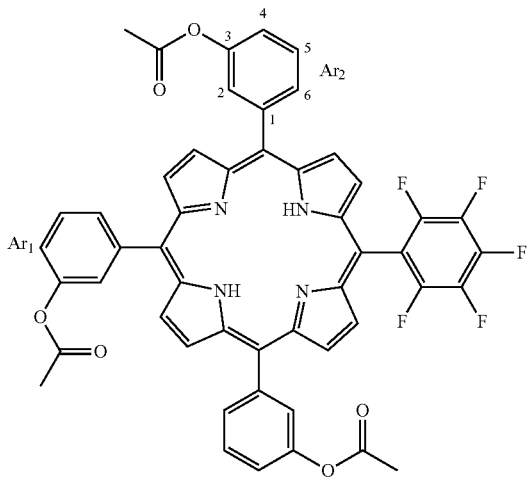

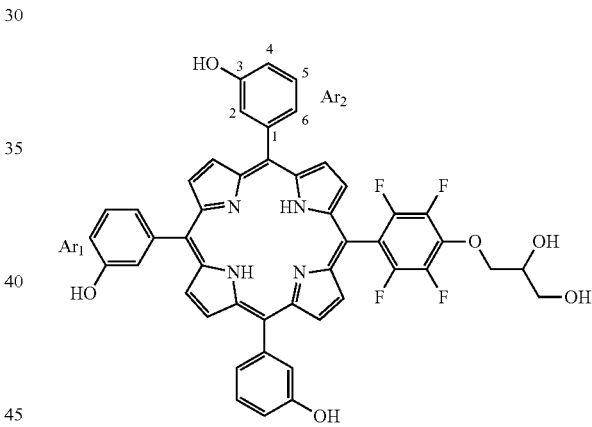

$^1$H-NMR (400 MHz, acetone-d$_6$): δ=-2.82 (s, 2H, NH), 2.34 (s, 3H, Ar$_1$—O(CO)CH$_3$), 2.43 (s, 6H, Ar$_2$—O(CO)CH$_3$), 7.61 (dd, J=8.2, 2.5 Hz, 3H, Ar—H-6), 7.83 (t, J=8.0 Hz, 3H, Ar$_1$H-5), 7.84 (t, J=7.9 Hz, 3H, Ar$_2$—H-5), 8.01-8.17 (m, 6H, Ar—H-2, Ar—H-4), 8.93-9.21 (m, 8H, β-H$_{Pyrrol}$) ppm.

$^{13}$C-NMR: (126 MHz, acetone-d$_6$): δ=21.4 (CH$_3$), 100.8 (Ar$_F$—C$_{ipso}$), 119.8 (Ar$_F$—C$_{meso}$), 120.9 (Ar$_2$—C-6), 121.4 (Ar$_1$—C-6), 127.8 (Ar$_2$—C-5), 127.9 (Ar$_1$C-5), 128.1 (Ar$_2$—C-2), 128.1 (Ar$_1$C-2), 132.3 (Ar—C-4), 143.0 (Ar$_2$—C-1), 143.2 (Ar$_1$C-1), 145.7 (Ar$_F$—C$_{meta}$), 147.7 (Ar$_F$—C$_{ortho}$), 149.4 (Ar$_1$C-3), 149.5 (Ar$_2$—C-3), 169.8 (C=O) ppm.

$^{19}$F-NMR (376 MHz, acetone-d$_6$): δ=-139.95 (dd, J=23.6, 7.9 Hz, 2F, Ar—F$_{ortho}$), -156.01 (t, J=20.5 Hz, 1F, Ar—F$_{para}$), -164.72 (td, J=22.7, 7.6 Hz, 2F, Ar—F$_{meta}$) ppm.

$^1$H-NMR (500 MHz, acetone-d$_6$): δ=-2.76 (s, 2H, NH), 3.80-3.88 (m, 2H, OCH$_2$), 4.01 (t, J=5.7 Hz, 1H, β-OH), 4.20-4.25 (m, 1H, OCH$_2$CH), 4.39 (d, J=5.3 Hz, 1H, γ-OH), 4.62 (dd, J=10.2, 6.2 Hz, 1H, Ar$_F$—OCH$_2$), 4.73 (dd, J=10.2, 4.4 Hz, 1H, Ar$_F$—OCH$_2$), 7.31-7.35 (m, 3H, Ar—H-6), 7.59-7.65 (m, 3H, Ar—H-5), 7.70-7.76 (m, 6H, Ar—H-2+Ar—H-4), 8.90 (s, 3H, Ar—OH), 8.92-9.24 (m, 8H, β-H$_{Pyrrole}$) ppm.

$^{13}$C-NMR (126 MHz, acetone-d$_6$): δ=63.0 (OCH$_2$), 71.3 (OCH$_2$CH), 76.7 (Ar$_F$—OCH$_2$), 101.6 (Ar$_F$—C$_{meso}$), 114.4 (Ar$_F$—C$_{ipso}$), 115.2 (Ar—C-6), 120.7 (Ar—C$_{meso}$), 121.8 (Ar—C$_{meso}$), 122.0 (Ar$_1$—C-2), 122.0 (Ar$_2$—C-2), 126.3 (Ar$_1$—C-4), 126.4 (Ar$_2$—C-4), 127.8 (Ar$_1$C-5), 127.8 (Ar$_2$—C-5), 139.2 (Ar$_F$—C$_{para}$), 141.4 (d, $^1$J$_{C-F}$=242.1 Hz, Ar$_F$—C$_{meta}$), 142.9 (Ar—C$_{ipso}$), 143.1 (Ar—C$_{ipso}$), 146.9 (d, $^1$J$_{C-F}$=237.8 Hz, Ar$_F$—C$_{ortho}$), 155.9 (Ar$_1$C-3), 156.0 (Ar$_2$—C-3) ppm.

$^{19}$F-NMR (376 MHz, acetone-d$_6$): δ=-141.84--142.03 (m, 2F, Ar—F$_{ortho}$), -158.95 (d, J=20.2 Hz, 2F, Ar—F$_{meta}$) ppm.

HRMS (ESI-TOF): m/z calc. for $C_{47}H_{33}F_4N_4O_6$ [M+H]$^+$: 825.2336; found: 865.2402.

UV-VIS (MeOH), $\lambda_{max}$ [log ε(L·mol$^{-1}$·cm$^{-1}$)]: 413 (5.28), 511 (4.21), 545 (3.68), 587 (3.69), 642 (3.29) nm.

1.4. Preparation of 5,10,15,20-tetrakis-[2,3,5,6-tetrafluoro-4-(1,3-dihydroxyprop-2-ylamino)-phenyl]-porphyrin In a typical experiment, tetrakis(pentafluorophenyl)porphyrin (107 mg, 0.109 mmol) was dissolved in a two-necked round bottom flask with dry DMSO (2.0 ml), 2-Amino-1,3-dihydroxy-propane (260 mg, 2.85 mmol) was added and the reaction mixture stirred at 100° C. for 4 hours. After aqueous workup, extraction with ethyl acetate and drying with $Na_2SO_4$, the crude product was purified by reversed phase column chromatography (MeOH/H$_2$O=85:15) and recrystallized (MeOH/H$_2$O) to obtain a purple solid (77.0 mg, 59.8 μmol, 54%).

5,10,15,20-tetrakis-[2,3,5,6-tetrafluoro-4-(1,3-dihydroxyprop-2-ylamino)-phenyl]-porphyrin

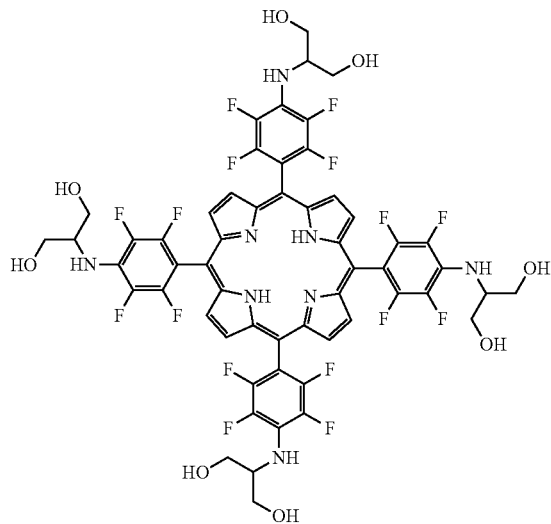 [SMILES: OCC(CO)Nc1c(F)c(F)c(-c2c3nc(c(-c4c(F)c(F)c(NC(CO)CO)c(F)c4F)c4ccc([nH]4)c(-c4c(F)c(F)c(NC(CO)CO)c(F)c4F)c4nc(c(-c5c(F)c(F)c(NC(CO)CO)c(F)c5F)c5ccc2[nH]5)C=C4)C=C3)c(F)c1F]

$^1$H-NMR (500 MHz, acetone-d$_6$): δ=−2.82 (s, 2H, NH), 3.94-4.08 (m, 16H, OCH$_2$), 4.17 (dp, J=9.9, 5.1 Hz, 4H, NHCH), 4.25 (t, J=5.5 Hz, 8H, OH), 5.30 (dt, $^3J_{H-H}$=9.8, $^4J_{H-F}$=3.0 Hz, 4H, NH), 9.25 (s, 8H, β-H$_{Pyrrole}$) ppm.

$^{13}$C-NMR (126 MHz, acetone-d$_6$): δ=58.8 (NH—CH), 62.7 (OCH$_2$), 62.8 (OCH$_2$), 106.0 (Ar$_F$—C$_{meso}$), 107.2 (t, $^2J_{C-F}$=20.1 Hz, Ar$_F$—C$_{ipso}$), 130.5 (t, J=11.5 Hz, Ar$_F$—C$_{para}$), 132.7 (β-C$_{Pyrrole}$), 138.3 (dd, $^{1,2}J_{C-F}$=238.8, 16.0 Hz, Ar$_F$—C$_{meta}$), 147.8 (d, $^1J_{C-F}$=238.8 Hz, Ar$_F$—C$_{ortho}$) ppm.

$^{19}$F-NMR (376 MHz, acetone-d$_6$): δ=−143.38 (d, J=16.1 Hz, 4F, Ar—F$_{ortho}$), −161.29 (d, J=19.3 Hz, 4F, Ar—F$_{meta}$) ppm.

HRMS (ESI-TOF): m/z calc. for $C_{56}H_{43}F_{16}F_{16}N_8O_8$ [M+H]$^+$: 1259.2948; found: 1259.3045.

UV-VIS (DCM), $\lambda_{max}$ [log ε(L·mol$^{-1}$·cm$^{-1}$)]: 417 (5.42), 509 (4.38), 544 (3.82), 586 (3.88), 648 (3.07) nm.

1.5. Preparation of Further Dihydroxypropylamino-Substituted Dipyrromethanes, BODIPYs, Porphyrins and Corroles General Procedure for the Synthesis of Dihydroxypropylamino-Substituted Dipyrromethanes, BODIPYs, Porphyrins and Corroles In a typical experiment, the amine (28 eq.) was dissolved in a three-necked round bottom flask with argon gas inlet and magnetic stirrer in dry DMSO. Then, the starting compound (1 eq.) was added and the reaction was stirred for 4 h at 100° C. After extraction with EA and aqueous workup, the organic phase was dried with sodium sulfate, filtered and the solvent evaporated. The crude product was purified by column chromatography (silica gel, DCM/MeOH, 85:15-8:2) and recrystallized with DCM/n-pentane.

5-[2,3,5,6-Tetrafluoro-4((R)-3-amino-1,2-dihydroxypropyl)-phenyl]-dipyrromethane

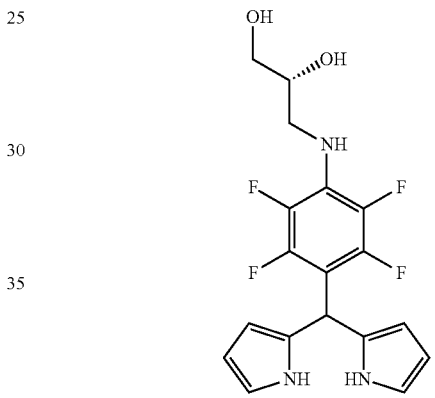

Referring to the general procedure, 5-(pentafluorophenyl)-dipyrromethane (268 mg, 0.86 mmol) was functionalized with (R)-3-amino-1,2-propanediol (1.10 g, 12.1 mmol). The product was obtained as brown oil (234 mg, 0.61 mmol, 71%).

R$_f$-value (DCM/MeOH 85:15): 0.71.

$^1$H NMR (500 MHz, D$_6$-acetone): δ=9.78 (s, 2H, NH), 6.70 (td, J=2.7, 1.6 Hz, 2H, 1,9-H$_{pyrrole}$), 6.03-5.99 (m, 2H, 2,8-H$_{pyrrole}$), 5.91 (s, 2H, 3,7-H$_{pyrrole}$), 5.79 (s, 1H, H$_{meso}$), 4.92 (s, 1H, NH), 4.11 (d, J=5.1 Hz, 2H, OH), 3.84 (ddt, J=19.1, 8.9, 5.1 Hz, 1H, OCH), 3.64-3.60 (m, 1H, NHCH), 3.61-3.58 (m, 1H, OCH$_2$), 3.40-3.34 (m, 1H, NHCH), 3.33 (d, J=4.0 Hz, 1H, OCH$_2$) ppm.

$^{13}$C NMR (126 MHz, D$_6$-acetone): δ=146.47-144.25 (m Ar—F—C$_{ortho}$), 138.76-136.55 (m, Ar—F—C$_{meta}$), 130.03 (s, 4,6-C), 127.63-127.30 (m, Ar—F—C$_{para}$), 117.16 (s, 1,9-C$_{Pyrrole}$), 108.21 (t, J=16.6 Hz, Ar—F—C$_{ipso}$), 107.45 (s, 2,8-C$_{pyrrole}$), 106.48 (s, 3,7-C$_{Pyrrole}$), 70.91 (d, OCH), 64.29 (t, OCH$_2$), 48.89 (t, OCH$_2$), 48.51 (t, J=3.9 Hz, NHCH$_2$), 32.82 (s, C$_{meso}$) ppm.

$^{19}$F NMR (471 MHz, D$_6$-acetone): δ=−146.38 (d, J=19.3 Hz, 2F, Ar—F$_{ortho}$), −161.33 (d, J=17.7 Hz, 2F, Ar—F$_{meta}$) ppm.

HRMS (ESI-TOF): m/z calc. for $C_{18}H_{17}F_4N_3O_2Na^+$ [M+Na]$^+$: 406.1154; found 406.1170.

5-[2,3,5,6-Tetrafluoro-4((S)-3-amino-1,2-dihydroxypropyl)-phenyl]-dipyrromethane

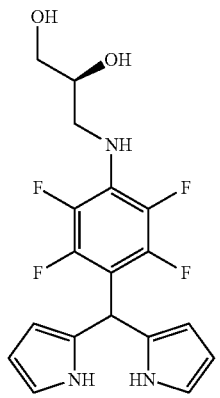 [SMILES: OC[C@@H](O)CNc1c(F)c(F)c(C(c2ccc[nH]2)c2ccc[nH]2)c(F)c1F]

Referring to the general procedure, 5-(pentafluorophenyl)-dipyrromethane (222 mg, 0.71 mmol) was functionalized with (S)-3-amino-1,2-propanediol (1.05 g, 11.6 mmol). The product was obtained as brown oil (249 mg, 0.65 mmol, 91%).

$R_f$-value (DCM/MeOH 85:15): 0.70.

$^1$H NMR (500 MHz, D$_6$-acetone): δ=9.78 (s, 2H, NH), 6.70 (td, J=2.7, 1.5 Hz, 2H, 1,9-H$_{pyrrole}$), 6.02-5.99 (m, 2H, 2,8-H$_{Pyrrole}$), 5.90 (dt, J=3.5, 2.0 Hz, 2H, 3-H$_{Pyrrole}$), 5.79 (s, 1H, H$_{meso}$), 4.92 (d, J=5.9 Hz, 1H, NH), 4.11 (d, J=5.1 Hz, 2H, OH), 3.83 (dq, J=17.9, 4.9 Hz, 1H, OCH), 3.62 (ddd, J=7.4, 4.0, 1.9 Hz, 1H, NHCH$_2$), 3.60 (s, 1H, OCH$_2$), 3.40-3.34 (m, 1H, NHCH$_2$), 3.34-3.31 (m, 1H, OCH$_2$) ppm.

$^{13}$C NMR (126 MHz, D$_6$-acetone) δ=145.36 (d, J=241.5 Hz, Ar—F—C$_{ortho}$), 137.60 (d, J=239.8 Hz, Ar—F—C$_{meta}$), 129.95 (d, J=20.0 Hz s, 4,6-C$_{pyrrole}$), 127.41 (d, J=12.6 Hz, Ar—F—C$_{para}$), 117.06 (d, J=21.5 Hz, 1,9-C$_{Pyrrole}$), 108.27 (d, J=16.7 Hz, Ar—F—C$_{ipso}$), 107.42 (d, J=5.6 Hz, 2,8-C$_{pyrrole}$), 106.47 (s, 3,7-C$_{Pyrrole}$), 70.90 (s, OCH), 64.29 (s, OCH$_2$), 48.50 (d, J=3.9 Hz, NHCH$_2$), 32.82 (s, C$_{meso}$) ppm.

$^{19}$F NMR (471 MHz, D$_6$-acetone): δ=−146.40 (d, J=18.7 Hz, 2F, Ar—F$_{ortho}$)), −161.35 (d, J=17.4 Hz, 2F, Ar—F$_{meta}$) ppm.

HRMS (ESI-TOF): m/z calc. for C$_{18}$H$_{17}$F$_4$N$_3$O$_2$Na$^+$ [M+Na]$^+$: 406.1154; found: 406.1163.

8-[2,3,5,6-Tetrafluoro-4((R)-3-amino-1,2-dihydroxypropyl)-phenyl]-4,4-difluoro-4-bora-3a,4a-diaza-s-indacene

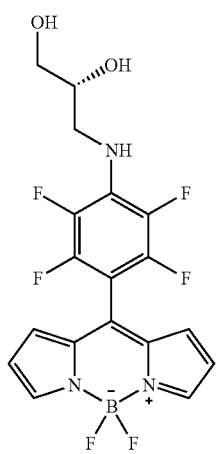 [SMILES: OC[C@H](O)CNc1c(F)c(F)c(C2=C3C=CC=[N+]3[B-](F)(F)n3cccc32)c(F)c1F]

5-[2,3,5,6-Tetrafluoro-4((R)-3-amino-1,2-dihydroxypropyl)-phenyl]-dipyrromethane (171 mg, 0.44 mmol, 1 eq.) was placed in a 100 mL one-neck flask with DCM (20 mL) under argon atmosphere. After DDQ (107 mg, 0.47 mmol, 1 eq.) was added, the mixture was stirred for 5 min. Then, DIPEA (0.54 mL, 410 mg, 3.17 mmol, 7 eq.) was added and stirred for 15 min. After BF$_3$.OEt$_2$ (0.60 mL, 25.3 g, 178 mmol, 11 eq.) was added, the reaction was stopped after 30 minutes by adding water to the reaction mixture. The aqueous phase was extracted with DCM and EA, the organic phase washed with water, dried with sodium sulfate, filtered and the solvent evaporated. After column chromatography (silica gel, DCM/MeOH, 85:15), the product was obtained as orange-red powder (76 mg, 0.17 mmol, 39%).

melting range: 132-135° C.

$R_f$-value (DCM/MeOH 85:15): 0.75.

$^1$H NMR (500 MHz, D$_6$-acetone): δ=8.04 (s, 2H, 1,9-H$_{Pyrrole}$), 7.21 (d, J=4.2 Hz, 2H, 3,7-H$_{Pyrrole}$), 6.67 (d, J=4.2 Hz, 2H, 2,8-H$_{Pyrrole}$), 5.60 (td, J=7.8, 7.3, 3.5 Hz, 1H, NH), 4.22 (s, 2H, OH), 3.92 (dt, J=9.9, 5.0 Hz, 1H, OCH), 3.77-3.70 (m, 1H, NHCH$_2$), 3.63 (d, J=5.4 Hz, 2H, OCH$_2$), 3.52 (dt, J=13.3, 6.6 Hz, 1H, NHCH$_2$) ppm.

$^{13}$C NMR (126 MHz, D$_6$-acetone): δ=145.89 (d, J=19.8 Hz, 1,9-C$_{Pyrrole}$), 135.51 (s, Ar$_F$—C$_{meso}$), 132.51 (s, Ar$_F$—C$_{ortho}$), 131.32 (s, 3,7-C$_{Pyrrole}$), 119.46 (s, 2,8-C$_{Pyrrole}$), 71.03 (d, OCH), 64.31 (t, OCH$_2$), 48.25 (d, NHCH) ppm.

$^{19}$F NMR (376 MHz, D$_6$-acetone): δ −143.19 (d, J=20.9 Hz, 2F, Ar—F$_{ortho}$), −144.57 (q, J=55.6, 27.8 Hz, BF$_2$), −160.71 (d, J=21.5 Hz, 2F, Ar—F$_{meta}$) ppm.

HRMS (ESI-TOF): m/z calc. for C$_{18}$H$_{13}$BF$_6$N$_3$O$_2$ [M−H]$^-$: 428.1004; found: 428.1018.

UV/Vis (MeOH): λ$_{max}$/nm [lg ε/L·mol$^{-1}$·cm$^{-1}$]=377 (4.05), 510 (4.78).

Fluorescence emission (MeOH): λ$_{em}$/nm: 533 at λ$_{ex}$/nm: 370; 510.

8-[2,3,5,6-Tetrafluoro-4((S)-3-amino-1,2-dihydroxypropyl)-phenyl]-4,4-difluoro-4-bora-3a,4a-diaza-s-indacene

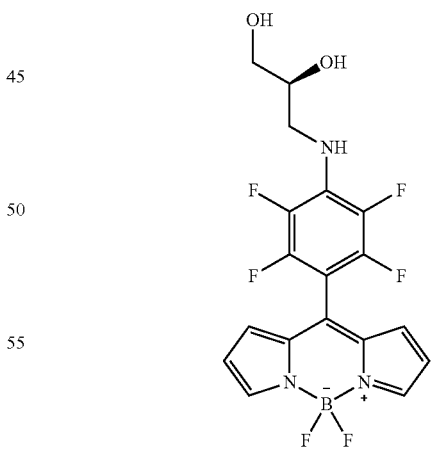

5-[2,3,5,6-Tetrafluoro-4((S)-3-amino-1,2-dihydroxypropyl)-phenyl]-dipyrromethane (215 mg, 0.56 mmol, 1 eq.) was placed in a 100 mL one-neck flask with DCM (30 mL) under argon atmosphere. After DDQ (135 mg, 0.59 mmol, 1 eq.) was added, the mixture was stirred for 5 min. Then, DIPEA (0.67 mL, 509 mg, 3.93 mmol, 7 eq.) was added and stirred for 15 minutes. After BF$_3$.OEt$_2$ (0.76 mL, 25.3 g, 178 mmol, 11 eq.) was added, the reaction was stopped after 30 minutes by adding water to the reaction mixture. The aqueous phase was extracted with DCM and EA, the organic phase washed with water, dried with sodium sulfate and the solvent evaporated. After column chromatography (silica gel, DCM/MeOH, 85:15), the product was obtained as orange-red powder (70 mg, 0.16 mmol, 29%).

melting range: 108-110° C.

$R_f$-value (DCM/MeOH, 85:15): 0.73.

$^1$H NMR (500 MHz, D$_6$-acetone): δ=8.04 (s, 2H, 1,9-H$_{Pyrrole}$), 7.21 (d, J=4.3 Hz, 2H, 3,7-H$_{Pyrrole}$), 6.67 (d, J=4.3 Hz, 2H, 2,8-H$_{Pyrrole}$), 5.61 (q, J=4.5, 3.3 Hz, 1H, NH), 4.25 (d, J=4.7 Hz, 2H, OH), 4.01-3.88 (m, 1H, OCH), 3.74 (dt, J=11.7, 5.5 Hz, 1H, NHCH$_2$), 3.63 (d, J=5.2 Hz, 2H, OCH$_2$), 3.52 (dt, J=13.3, 6.6 Hz, 1H, NHCH$_2$) ppm.

$^{13}$C NMR (126 MHz, D$_6$-acetone): δ=145.82 (d, J=8.4 Hz, 1,9-C$_{Pyrrole}$), 144.03 (d, Ar$_F$—C$_{ortho}$), 137.30 (d, J=242.2 Hz, Ar$_F$—C$_{meta}$), 135.51 (s, Ar$_F$—C$_{meso}$), 132.51 (s, Ar$_F$—C$_{para}$), 131.32 (d, 3,7-C$_{Pyrrole}$), 119.47 (d, 2,8-C$_{Pyrrole}$), 97.84 (t, J=18.5 Hz, Ar$_F$—C$_{ipso}$), 71.06 (d, OCH), 64.33 (t, OCH$_2$), 48.22 (d, NHCH$_2$) ppm.

$^{19}$F NMR (376 MHz, D$_6$-acetone): δ=−143.15 (d, J=21.5 Hz, 2F, Ar—F$_{ortho}$), −144.35--144.67 (m, 2F, BF$_2$), −160.68 (d, J=21.6 Hz, 2F, Ar—F$_{meta}$) ppm.

HRMS (ESI-TOF): m/z calc. for C$_{18}$H$_{12}$BF$_6$N$_3$O$_2$ [M−2H]$^{2-}$: 213.0487; found: 213.0809.

UV/Vis (MeOH): $λ_{max}$/nm [lg ε/L·mol$^{-1}$·c$^{-1}$]=375 (4.10), 511 (4.76).

Fluorescence emission (MeOH): $λ_{em}$/nm: 533 at $λ_{ex}$/nm: 370; 510.

5,10,15,20-Tetrakis-[2,3,5,6-tetrafluoro-4-(R)-2,3-dihydroxypropylamino)-phenyl]-porphyrin

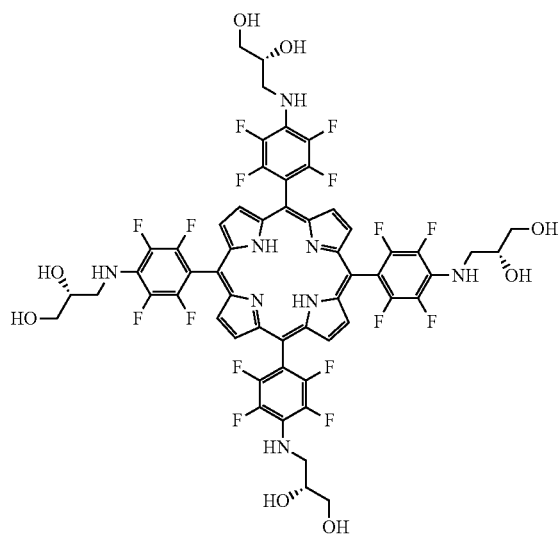 [SMILES: OC[C@H](O)CNc1c(F)c(F)c(-c2c3nc(c(-c4c(F)c(F)c(NC[C@@H](O)CO)c(F)c4F)c4ccc([nH]4)c(-c4c(F)c(F)c(NC[C@@H](O)CO)c(F)c4F)c4nc(c(-c5c(F)c(F)c(NC[C@@H](O)CO)c(F)c5F)c5ccc2[nH]5)C=C4)C=C3)c(F)c1F]

Referring to the general procedure, 5,10,15,20-tetrakis(2,3,4,5,6-pentafluorophenyl)porphyrin (262 mg, 0.26 mmol) was functionalized with (R)-3-amino-1,2-propanediol (529 mg, 5.81 mmol). The product was obtained as purple crystals (155 mg, 0.12 mmol, 45%).

melting range: 298-231° C.

$R_f$-value (DCM/MeOH, 85:15): 0.17.

$^1$H NMR (500 MHz, D$_6$-acetone): δ=9.27 (s, 8H, β-H), 5.59 (s, 4H, NH), 4.40 (s, 4H, OH), 4.13 (t, J=5.8 Hz, 4H, OCH), 4.04 (s, 4H, OH), 3.95 (dd, J=12.9, 6.8 Hz, 4H, NHCH), 3.78 (d, J=5.3 Hz, 8H, OCH$_2$), 3.71 (dt, J=12.7, 6.3 Hz, 4H, NHCH), −2.80 (s, 2H, NH$_{Pyrrole}$) ppm.

$^{13}$C NMR (126 MHz, D$_6$-acetone): δ=147.04 (dd, J$_{C—F}$=247.6, 9.2 Hz, Ar$_F$—C$_{ortho}$), 137.45 (dd, J$_{C—F}$=239.8, 17.2 Hz, Ar$_F$—C$_{meta}$), 130.37 (t, J=11.4 Hz, Ar$_F$—C$_{para}$), 106.25 (t, J=20.2 Hz, Ar$_F$—C$_{ipso}$), 105.28 (s, Ar$_F$—C$_{meso}$), 71.27 (d, OCH), 64.54 (t, OCH$_2$), 48.66 (t, J=13.9 Hz, NHCH$_2$) ppm.

$^{19}$F NMR (471 MHz, D$_6$-acetone): δ=−143.50 (d, J=18.7 Hz, 4F, Ar—F$_{ortho}$), −161.91 (d, J=19.8 Hz, 4F, Ar—F$_{meta}$) ppm.

HRMS (ESI-TOF): m/z calc. for C$_{56}$H$_{43}$F$_{16}$O$_8$N$_8$$^+$ [M+H]$^+$: 1259.2949; found: 1259.2946.

UV/Vis (MeOH): $λ_{max}$/nm [lg ε/L·mol$^{-1}$·cm$^{-1}$]=417 (5.27), 510 (4.23), 543 (3.75), 586 (3.78), 648 (3.16).

5,10,15,20-Tetrakis-[2,3,5,6-tetrafluoro-4-((S)-2,3-dihydroxypropylamino)-phenyl]-porphyrin

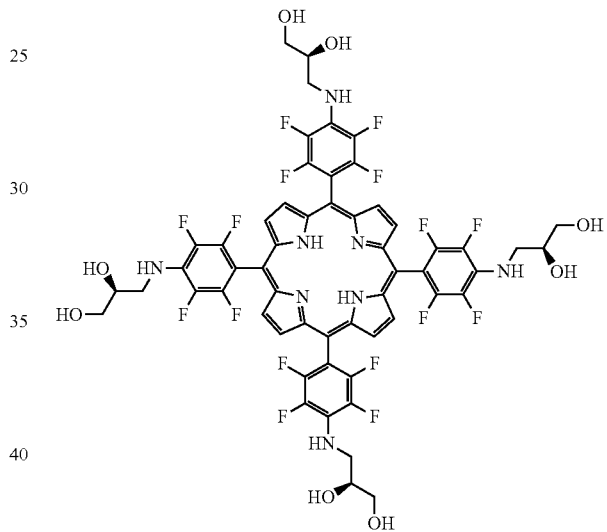

Referring to the general procedure, 5,10,15,20-tetrakis(2,3,4,5,6-pentafluorophenyl)porphyrin (123 mg, 0.12 mmol) was functionalized with (S)-3-amino-1,2-propanediol (260 mg, 2.86 mmol). The product was obtained as purple crystals (49 mg, 0.03 mmol, 30%).

melting range: >300° C.

$R_f$-value (DCM/MeOH, 85:15): 0.11.

$^1$H NMR (500 MHz, D$_6$-acetone): δ=9.27 (s, 8H, β-H), 5.60 (tt, J=6.0, 2.7 Hz, 4H, NH), 4.43 (s, 4H, OH), 4.13 (dt, J=7.7, 4.9 Hz, 4H, OCH), 4.07 (s, 4H, OH), 3.95 (ddd, J=12.0, 6.8, 4.4 Hz, 4H, NHCH), 3.83-3.75 (m, 8H, OCH$_2$), 3.71 (dt, J=13.2, 6.5 Hz, 4H, NHCH), −2.80 (s, 2H, NH$_{Pyrrole}$) ppm.

$^{13}$C NMR (126 MHz, D$_6$-acetone): δ=148.15-145.96 (dt, J$_{C—F}$=275.94, Ar$_F$—C$_{ortho}$), 138.50-136.35 (dt, J$_{C—F}$=270.90, Ar$_F$—C$_{meta}$), 130.38 (t, J=11.0 Hz, Ar$_F$—C$_{para}$), 106.25 (t, J=20.1 Hz, Ar$_F$—C$_{ipso}$), 105.27 (s, Ar$_F$—C$_{meso}$), 71.27 (d, OCH), 64.54 (t, OCH$_2$), 48.91 (t, NHCH$_2$) ppm.

$^{19}$F NMR (471 MHz, D$_6$-acetone): δ=−143.50 (d, J=19.0 Hz, 4F, Ar—F$_{ortho}$), −161.91 (d, J=18.2 Hz, 4F, Ar—F$_{meta}$) ppm.

HRMS (ESI-TOF): m/z calc. for $C_{56}H_{43}F_{16}O_8N_8^+$ [M+H]$^+$: 1259.2949; found: 1259.2845.

UV/Vis (MeOH): $\lambda_{max}$/nm [lg ε/L·mol$^{-1}$·cm$^{-1}$]=417 (5.27), 510 (4.23), 543 (3.75), 586 (3.78), 648 (3.16).

5,15-Bis-(3-hydroxyphenyl)-10,20-bis-[2,3,5,6-tetra-fluoro-4(2-amino-1,3-dihydroxypropyl)-phenyl]-porphyrin

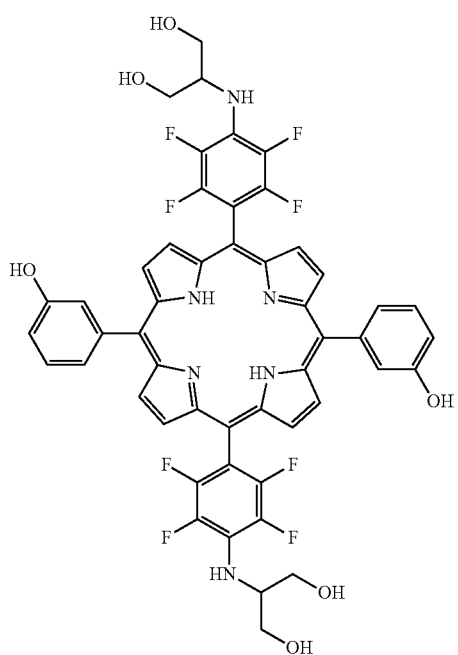 [SMILES: OCC(CO)Nc1c(F)c(F)c(-c2c3nc(c(-c4cccc(O)c4)c4ccc([nH]4)c(-c4c(F)c(F)c(NC(CO)CO)c(F)c4F)c4nc(c(-c5cccc(O)c5)c5ccc2[nH]5)C=C4)C=C3)c(F)c1F]

Referring to the general procedure, 5,15-bis(3-hydroxyphenyl)-10,20-bis-(pentafluorophenyl)porphyrin (101 mg, 0.12 mmol) was functionalized with 2-amino-1,3-propanediol (277 mg, 3.00 mmol). The product was obtained as purple crystals (34 mg, 0.03 mmol, 29%).

melting range: >300° C.

R$_f$-value (DCM/MeOH, 85:15): 0.50.

$^1$H NMR (500 MHz, D$_6$-acetone): δ=9.12 (dd, J=52.6, 4.9 Hz, 8H, β-H), 7.81 (t, J=2.0 Hz, 2H, Ar—H-2), 7.78 (d, J=7.4 Hz, 2H, Ar—H-6), 7.70-7.63 (m, 2H, Ar—H-5), 7.37 (ddd, J=8.3, 2.5, 1.0 Hz, 2H, Ar—H-4), 5.30 (dt, J=9.8, 2.9 Hz, 2H, NH), 4.20 (ddd, J=10.0, 5.0 Hz, 4H, NHCH), 4.09 (dd, J=10.8, 4.3 Hz, 6H, OCH$_3$), 4.02 (dd, J=10.8, 5.6 Hz, 6H, OCH$_2$), -2.74 (s, 2H, NH$_{Pyrrole}$) ppm.

$^{13}$C NMR (126 MHz, D$_6$-acetone): δ=155.98 (s, Ar—C$_{meso}$), 146.95 (d, J=238.4 Hz, Ar$_F$—C$_{ortho}$), 142.66 (s, Ar—C$_{ipso}$), 137.45 (dd, J=238.7, 17.0 Hz, Ar$_F$—C$_{meta}$), 129.47 (d, J=12.7 Hz, Ar$_F$—C$_{para}$), 127.83 (d, Ar—C-5), 126.40 (d, Ar—C-6), 122.03 (d, Ar—C-2), 120.90 (d, Ar—C-3), 115.21 (d, Ar—C-4), 107.35 (s, Ar$_F$—C$_{ipso}$), 104.19 (s, Ar$_F$—C$_{meso}$), 62.01 (d, J=4.9 Hz, OCH$_3$), 57.95 (d, NHCH) ppm.

$^{19}$F NMR (471 MHz, D$_6$-acetone): δ=-143.37 (d, J=21.1 Hz, 4F, Ar—F$_{ortho}$), -161.42 (d, J=20.0 Hz, 4F, Ar—F$_{meta}$) ppm.

HRMS (ESI-TOF): m/z calc. for $C_{50}H_{37}F_8N_6O_6$ [M+H]$^+$: 969.2648; found: 969.2674.

UV/Vis (MeOH): $\lambda_{max}$/nm [lg ε/L mol$^{-1}$·cm$^{-1}$]=414 (5.47), 509 (4.41), 545 (4.08), 586 (3.99), 643 (3.73).

5,15-Bis-(3-hydroxyphenyl)-10,20-bis-[2,3,5,6-tetra-fluoro-4((R)-3-amino-1,2-dihydroxypropyl)-phenyl]-porphyrin

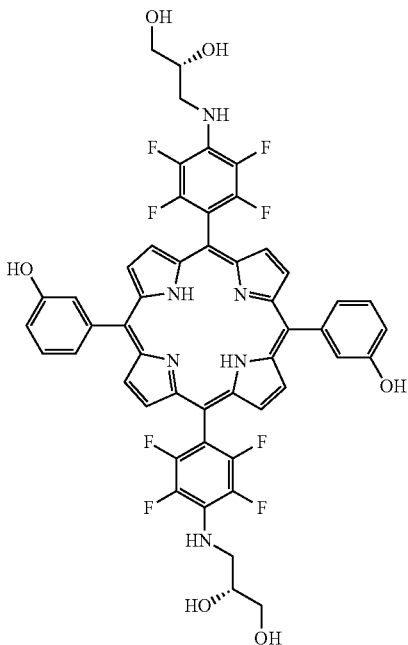 [SMILES: OC[C@H](O)CNc1c(F)c(F)c(-c2c3nc(c(-c4cccc(O)c4)c4ccc([nH]4)c(-c4c(F)c(F)c(NC[C@@H](O)CO)c(F)c4F)c4nc(c(-c5cccc(O)c5)c5ccc2[nH]5)C=C4)C=C3)c(F)c1F]

Referring to the general procedure, 5,15-bis(3-hydroxyphenyl)-10,20-bis-(pentafluorophenyl)porphyrin (95.0 mg, 0.11 mmol) was functionalized with (R)-3-amino-1,2-propanediol (298 mg, 3.28 mmol). The product was obtained as purple crystals (65 mg, 0.06 mmol, 58%).

melting range: 238-240° C.

R$_f$-value (DCM/MeOH, 85:15): 0.69.

$^1$H NMR (500 MHz, D$_6$-acetone): δ=9.40-8.83 (m, 8H, β-H), 7.81 (t, J=2.1 Hz, 2H, Ar—H-2), 7.78 (d, J=7.3 Hz, 2H, Ar—H-6), 7.71-7.64 (m, 2H, Ar—H-5), 7.37 (ddd, J=8.3, 2.5, 1.0 Hz, 2H, Ar—H-4), 5.55 (s, 2H, NH), 4.38 (s, 2H, OH), 4.15 (dq, J=7.3, 5.0 Hz, 2H, OCH), 3.96 (d, J=14.0 Hz, 2H, NHCH), 3.79 (dd, J=5.4, 1.5 Hz, 8H, OCH$_2$), 3.72 (dd, J=13.1, 7.4 Hz, 4H, NHCH), -2.74 (s, 2H, NH$_{pyrrole}$) ppm.

$^{13}$C NMR (126 MHz, D$_6$-acetone): δ=155.97 (s, Ar—C$_{meso}$), 146.96 (d, J=238.4 Hz, Ar$_F$—C$_{ortho}$), 142.67 (s, Ar—C$_{ipso}$), 137.37 (dd, J=239.7, 14.4 Hz, Ar$_F$—C$_{meta}$), 130.69-129.79 (m, Ar$_F$—C$_{para}$), 127.83 (d, Ar—C-5), 126.42 (d, Ar—C-6), 122.03 (d, Ar—C-2), 120.88 (d, Ar—C-3), 115.20 (d, Ar—C-4), 106.87 (t, J=20.1 Hz, Ar$_F$—C$_{ipso}$), 104.23 (s, Ar$_F$—C$_{meso}$), 71.17 (d, OCH), 64.44 (t, OCH$_2$), 48.67 (t, NHCH$_2$) ppm.

$^{19}$F NMR (471 MHz, D$_6$-acetone): δ=-143.52 (d, J=21.0 Hz, 4F, Ar—F$_{ortho}$), -162.01 (d, J=18.9 Hz 4F, Ar—F$_{meta}$) ppm.

HRMS (ESI-TOF): m/z calc. for $C_{50}H_{37}F_8N_6O_6$ [M+H]$^+$: 969.2648; found: 969.2664.

UV/Vis (MeOH): $\lambda_{max}$/nm [lg ε/L·mol$^{-1}$·cm$^{-1}$]=415 (5.44), 510 (4.30), 546 (3.99), 587 (3.85), 644 (3.60).

5,15-Bis-(3-hydroxyphenyl)-10,20-bis-[2,3,5,6-tetrafluoro-4(S)-3-amino-1,2-dihydroxypropyl)-phenyl] porphyrin

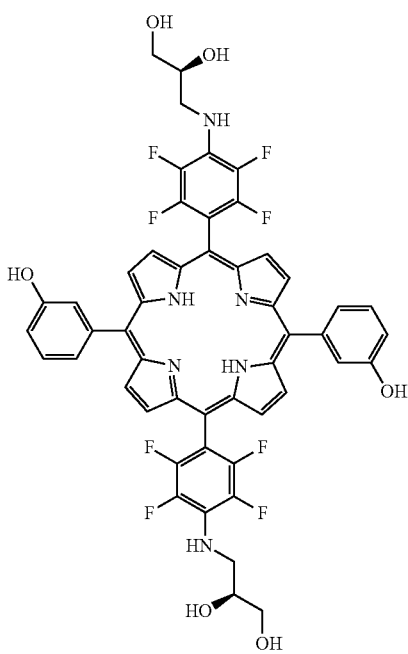 [SMILES: OC[C@@H](O)CNc1c(F)c(F)c(-c2c3nc(c(-c4cccc(O)c4)c4ccc([nH]4)c(-c4c(F)c(F)c(NC[C@H](O)CO)c(F)c4F)c4nc(c(-c5cccc(O)c5)c5ccc2[nH]5)C=C4)C=C3)c(F)c1F]

Referring to the general procedure, 5,15-bis(3-hydroxyphenyl)-10,20-bis-(pentafluorophenyl)porphyrin (86.5 mg, 0.10 mmol) was functionalized with (S)-3-amino-1,2-propanediol (321 mg, 3.50 mmol). The product was obtained as purple crystals (51 mg, 0.05 mmol, 50%).

melting range: 250-254° C.

$R_f$-value (DCM/MeOH, 85:15): 0.44.

$^1$H NMR (500 MHz, $D_6$-acetone): δ=9.31-8.88 (m, 8H, β-H), 7.85-7.81 (m, 2H, Ar—H-2), 7.78 (d, J=7.4 Hz, 2H, Ar—H-6), 7.70-7.64 (m, 2H, Ar—H-5), 7.37 (ddd, J=8.3, 2.5, 1.0 Hz, 2H, Ar—H-4), 5.57 (s, 2H, NH), 4.41 (d, J=7.0 Hz, 2H, OH), 4.16 (dq, J=9.8, 5.3 Hz, 2H, OCH), 4.11-4.01 (m, 2H, OH), 3.96 (dd, J=12.6, 5.1 Hz, 2H, NHCH), 3.88-3.77 (m, 4H, $OCH_2$), 3.73 (dd, J=12.8, 7.1 Hz, 2H, NHCH), −2.73 (s, 2H, $NH_{pyrrole}$) ppm.

$^{13}$C NMR (126 MHz, $D_6$-acetone) δ=155.98 (s, Ar—$C_{meso}$), 146.97 (d, J=237.8 Hz, $Ar_F$—$C_{ortho}$), 142.67 (s, Ar—$C_{ipso}$), 137.38 (dd, J=238.3, 13.9 Hz, $Ar_F$—$C_{meta}$), 130.13 (d, J=12.5 Hz, $Ar_F$—$C_{para}$), 127.83 (d, Ar—C-5), 126.41 (d, Ar—C-6), 122.04 (d, Ar—C-2), 120.88 (d, Ar—C-3), 115.22 (d, Ar—C-4), 106.87 (t, J=20.0 Hz $Ar_F$—$C_{ipso}$), 104.24 (s, $Ar_F$—$C_{meso}$), 71.20 (d, OCH), 64.46 (t, $OCH_2$), 48.67 (t, $NHCH_2$) ppm.

$^{19}$F NMR (471 MHz, $D_6$-acetone): δ=−143.50 (d, J=20.6 Hz, 4F, Ar—$F_{ortho}$), −162.00 (d, J=18.0 Hz, 4F, Ar—$F_{meta}$) ppm.

HRMS (ESI-TOF): m/z calc. for $C_{50}H_{37}F_8N_6O_6$ [M+H]$^+$: 969.2648; found: 969.2600.

UV/Vis (MeOH): $\lambda_{max}$/nm [lg ε/L·mol$^{-1}$·cm$^{-1}$]=415 (5.48), 509 (3.46), 545 (4.05), 587 (3.90), 644 (3.68).

5,10-Bis[2,3,5,6-tetrafluoro-4-(2-amino-1,3-dihydroxypropyl)-phenyl]corrole and 5,15-bis[2,3,5,6-tetrafluoro-4-(2-amino-1,3-dihydroxypropyl)-phenyl]corrole Referring to the general procedure, 5,10,15-tris(pentafluorophenyl)corrole (112 mg, 0.14 mmol) was functionalized with 2-amino-1,3-propanediol (265 mg, 2.91 mmol). The di-substituted product was obtained as isomeric mixture (59 mg, 0.06 mmol, 44%) and was isolated. The mono- and tri-substituted corrole were also detected, but were not isolated and characterized. The following characterization relates to the di-substituted product.

$^1$H NMR (500 MHz, $D_6$-acetone): δ=9.21-8.58 (m, 8H, β-H), 5.20 (dd, J=32.9, 9.7 Hz, 4H, NH), 4.22 (s, 8H, OH), 4.13 (dt, J=11.6, 5.7 Hz, 4H, NHCH), 4.06-3.91 (m, 16H, $OCH_2$) ppm. The pyrrolic protons were not detected.

$^{19}$F NMR (471 MHz, $D_6$-acetone): δ=−140.00 (d, J=20.1 Hz, 4F, 5-Ar—$F_{ortho}$, 15-Ar—$F_{ortho}$), −140.40 (d, J=18.7 Hz, 2F, 10-Ar—$F_{ortho}$), −143.32 (d, J=18.1 Hz, 2F, 10-Ar—$F_{ortho}$)), −143.83 (d, J=6.9 Hz, 4F, 5-Ar—$F_{ortho}$, 15-Ar—$F_{ortho}$)), −156.65 (1F, 5-Ar—$F_{para}$, 15-Ar—$F_{para}$), −157.09 (t, J=20.4 Hz, 1F, 10-Ar—$F_{para}$), −161.12 (d, J=19.3 Hz, 4F, 5-Ar—$F_{meta}$, 15-Ar—$F_{meta}$), −161.39 (d, J=17.6 Hz, 2F, 10-Ar—$F_{meta}$), −164.66-−164.92 (m, 2F, 10-Ar—$F_{meta}$), −165.17 (t, J=19.0 Hz, 4F, 5-Ar—$F_{meta}$, 15-Ar—$F_{meta}$) ppm.

HRMS (ESI-TOF): m/z calc. for $C_{43}H_{28}F_{13}N_6O_4$ [M+H]$^+$: 939.1965; found: 939.2026.

5,10,15-Tris[2,3,5,6-tetrafluoro-4(R)-3-amino-1,2-dihydroxypropyl)-phenyl]corrole

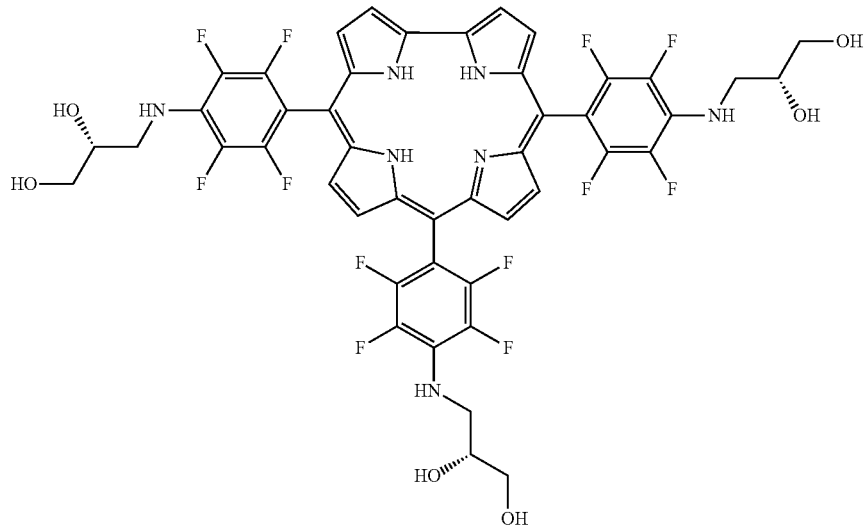 [SMILES: OC[C@H](O)CNc1c(F)c(F)c(-c2c3nc(c(-c4c(F)c(F)c(NC[C@@H](O)CO)c(F)c4F)c4ccc([nH]4)c4ccc([nH]4)c(-c4c(F)c(F)c(NC[C@@H](O)CO)c(F)c4F)c4ccc2[nH]4)C=C3)c(F)c1F]

Referring to the general procedure, 5,10,15-tris(pentafluorophenyl)corrole (133 mg, 0.16 mmol) (R)-3-amino-1,2-propanediol (310 mg, 3.40 mmol). The product was obtained as dark-purple powder (53 mg, 0.05 mmol, 31%).

melting range: 169-171° C.

$R_f$-value (DCM/MeOH, 85:15): 0.11.

NMR (500 MHz, $D_6$-acetone): δ=9.24-8.42 (m, 8H, β-H), 5.48 (d, J=43.0 Hz, 3H, NH), 4.49 (s, 3H, OH), 4.11 (h, J=7.9, 6.5 Hz, 3H, OCH), 4.02-3.83 (m, 3H, $NHCH_2$), 3.77 (d, J=5.3 Hz, 6H, $OCH_2$), 3.69 (q, J=7.9, 7.1 Hz, 3H, $NHCH_2$) ppm.

$^{13}C$ NMR (126 MHz, $D_6$-acetone): δ=71.28 (d, OCH), 64.50 (t, $OCH_2$), 48.70 (d, NHCH) ppm.

More C*atoms were not detected.

$^{19}F$ NMR (471 MHz, $D_6$-acetone): δ=-138.15 (d, J=21.3 Hz, 2F, 10-Ar—$F_{ortho}$)), -138.63 (4F, 5-Ar—$F_{ortho}$, 15-Ar—$F_{ortho}$), -156.47 (d, J=20.9 Hz, 4F, 5-Ar—$F_{meta}$, 15-Ar—$F_{meta}$), -156.76 (d, J=22.3 Hz, 2F, 10- Ar—$F_{meta}$) ppm.

HRMS (ESI-TOF): m/z calc. for $C_{46}H_{36}F_{12}N_7O_8K$ $[M+H]^+$: 1010.2536; found: 1010.2595.

UV/Vis (MeOH): $\lambda_{max}$/nm [lg ε/L·$mol^{-1}$·$cm^{-1}$]=413 (5.06), 568 (4.36), 605 (4.15).

5,10,15-Tris[2,3,5,6-tetrafluoro-4(S)-3-amino-1,2-dihydroxypropyl)-phenyl]corrole

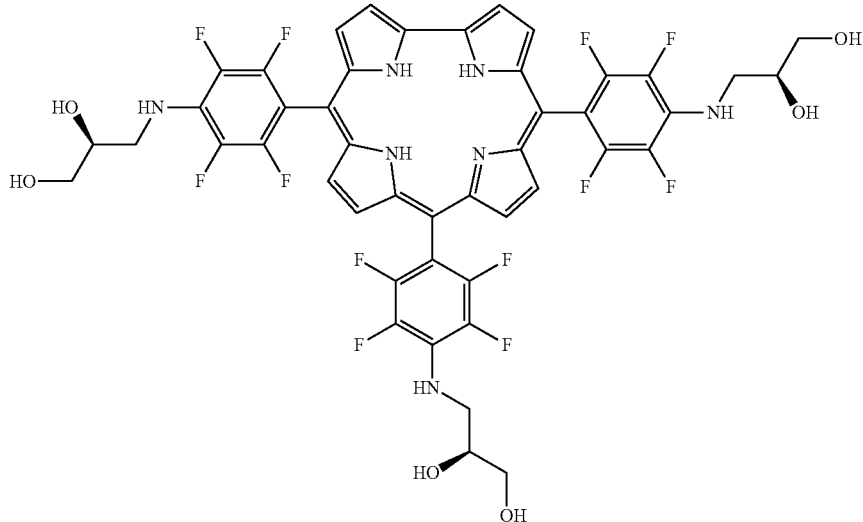 [SMILES: OC[C@@H](O)CNc1c(F)c(F)c(-c2c3nc(c(-c4c(F)c(F)c(NC[C@H](O)CO)c(F)c4F)c4ccc([nH]4)c4ccc([nH]4)c(-c4c(F)c(F)c(NC[C@H](O)CO)c(F)c4F)c4ccc2[nH]4)C=C3)c(F)c1F]

Referring to the general procedure, 5,10,15-tris(pentafluorophenyl)corrole (117 mg, 0.14 mmol) was functionalized with (S)-3-amino-1,2-propanediol (330 mg, 3.60 mmol). The product was obtained as purple crystals (85 mg, 0.084 mmol, 57%).

melting range: 223-225° C.

$R_f$-value (DCM/MeOH, 85:15): 0.275.

$^1H$ NMR (500 MHz, $D_6$-acetone): δ=9.28-8.54 (m, 8H, β-H), 5.48 (d, J=41.3 Hz, 3H, NH), 4.38 (s, 3H, OH), 4.14 (dq, J=10.0, 5.2 Hz, 3H, OCH), 3.94 (d, J=11.8 Hz, 3H, $NHCH_2$), 3.85-3.75 (m, 6H, $OCH_2$), 3.71 (dd, J=13.5, 7.2 Hz, 3H, $NHCH_2$) ppm.

$^{13}C$ NMR (126 MHz, $D_6$-acetone): δ=146.77 (dd, J=238.7, 65.4 Hz, $Ar_F$—$C_{ortho}$), 138.74-136.31 (m, $Ar_F$—$C_{meta}$), 129.73 (d, J=12.0 Hz, $Ar_F$—$C_{para}$), 115.91 (d, β-C), 107.72-106.77 (m, $Ar_F$—$C_{ipso}$), 105.10 (s, $Ar_F$—$C_{meso}$), 71.16 (d, OCH), 64.43 (t, $OCH_2$), 48.67 (d, NHCH) ppm.

$^{19}F$ NMR (471 MHz, $D_6$-acetone): δ=-143.32 (d, J=19.9 Hz, 2F, 10-Ar—$F_{ortho}$)), -143.80 (m, 4F, 5-Ar—$F_{ortho}$, 15-Ar—$F_{ortho}$), -161.63 (d, J=19.6 Hz, 4F, 5-Ar—$F_{meta}$, 15-Ar—$F_{meta}$), -161.91 (d, J=19.9 Hz, 2F, 10-Ar—$F_{meta}$) ppm.

HRMS (ESI-TOF): m/z calc. for $C_{46}H_{36}F_{12}N_7O_8K$ $[M+H]^+$: 1010.2536; found: 1010.2518.

UV/Vis (MeOH): $\lambda_{max}$/nm [lg ε/L·$mol^{-1}$·$cm^{-1}$]=411 (5.20), 570 (4.50), 605 (4.30).

Example 2

Preparation of 2,3-Dihydroxy-Propyloxy-Substituted Chlorins 2.1 Preparation of 5,10,15,20-tetrakis[2,3,5,6-tetrafluoro-4-(2,3-dihydroxypropyloxy)-phenyl]-chlorin In a typical experiment, all steps were performed under argon atmosphere. In a 250 ml three-necked flask p-toluenesulfonyl hydrazide (70.0 mg, 0.37 mmol), 5,10,15,20-tetrakis[2,3,5,6-tetrafluoro-4-(2,3-dihydroxypropyloxy)-phenyl]-porphyrin (234 mg, 0.185 mmol) and $K_2CO_3$ (230 mg, 1.66 mmol) were dissolved in 25.0 ml pyridine and stirred for 20 min at RT. Afterwards the reaction mixture was heated to 105° C. Additional p-toluenesulfonyl hydrazide (70.0 mg, 0.37 mmol) in 1.0 ml pyridine was added after 2 and 4 h. After 6.5 h heating 168 ml ethyl acetate and 84 ml $H_2O$ were added and the reaction mixture was refluxed for 1 h at 100° C. The organic layer was washed with 168 ml 2 M HCl, 168 ml $H_2O$ and 168 ml saturated $NaHCO_3$ solution, afterwards dried with $Na_2SO_4$ and evaporated to dryness. Then, the solid was dissolved in ethyl acetate (100 ml) and tetrachloro-o-benzoquinone (in a total of 147 mg, 0.59 mmol) was added in small portions (20 mg) every 15 min at RT to the stirring solution until the band at 735 nm in the UV/Vis spectrum just disappeared. The organic layer was washed twice with 168 ml 5% $NaHSO_3$ solution, once with 224 ml 0.01 M NaOH and once with 180 ml saturated $NaHCO_3$ solution and afterwards dried with $Na_2SO_4$. The product was evaporated to dryness and purified by column chromatography (DCM/ethyl acetate=98:2) and recrystallization (acetone/hexane) to obtain the product as a purple solid (198 mg, 0.156 mmol, 84%).

5,10,15,20-Tetrakis[2,3,5,6-tetrafluoro-4-(2,3-dihydroxypropyloxy)-phenyl]-chlorin

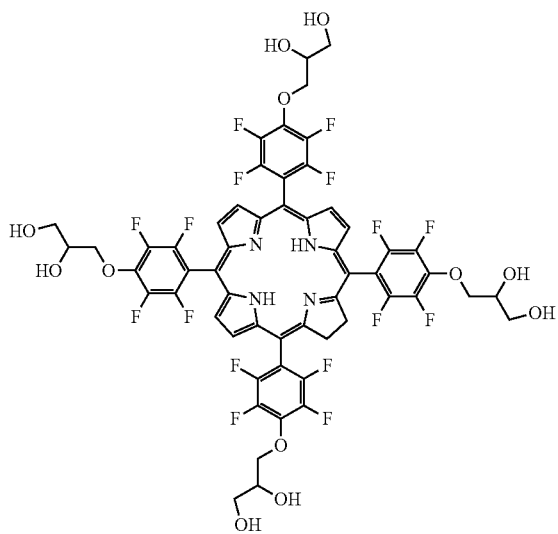 [SMILES: OCC(O)COc1c(F)c(F)c(-c2c3nc(c(-c4c(F)c(F)c(OCC(O)CO)c(F)c4F)c4ccc([nH]4)c(-c4c(F)c(F)c(OCC(O)CO)c(F)c4F)c4nc(c(-c5c(F)c(F)c(OCC(O)CO)c(F)c5F)c5ccc2[nH]5)CC4)C=C3)c(F)c1F]

$^1$H-NMR (500 MHz, acetone-d$_6$): δ=−1.39 (s, 2H, NH), 3.79-3.94 (m, 8H, CH$_2$OH), 4.00-4.17 (m, 4H, CH—OH), 4.18-4.32 (m, 4H, OCH$_2$CH), 4.44 (br s, 4H, CH$_2$OH), 4.50 (s, 4H, 2,3-β-H$_{Pyrrole}$), 4.56-4.66 (m, 4H, Ar$_F$—OCH$_2$), 4.67-4.82 (m, 4H, Ar$_F$—OCH$_2$), 8.73 (s, 2H, 12,13-β-H$_{Pyrrole}$), 8.76 (d, J=5.1 Hz, 2H, 7,18-β-H$_{Pyrrole}$), 9.10 (d, J=5.0 Hz, 2H, 8,17-β-H$_{Pyrrole}$) ppm.

$^{13}$C-NMR (126 MHz, acetone-d$_6$): δ=35.0 (2,3-β-C$_{Pyrrole}$), 62.9 (CH$_2$OH), 71.2 (OCH$_2$CH), 76.7 (Ar$_F$—OCH$_2$), 97.4 (5,20-Ar$_F$—C$_{meso}$), 106.8 (10,15-Ar$_F$—C$_{meso}$), 113.3 (t, $^2$J$_{C—F}$=20.0 Hz, 10,15-Ar$_F$—C$_{ipso}$), 113.81 (t, $^2$J$_{C—F}$=20.0 Hz, 5,20-Ar$_F$—C$_{ipso}$), 124.0 (7,18-β-C$_{Pyrrole}$), 128.7 (8,17-β-C$_{Pyrrole}$), 132.3 (12,13-β-H$_{Pyrrole}$), 135.4 (9,16-α-C$_{Pyrrole}$), 139.1 (Ar$_F$—C$_{para}$), 140.6 (6,19-α-C$_{Pyrrole}$), 141.22 (d, J=243.3 Hz, Ar$_F$—C$_{meta}$), 141.82 (dd, J=247.0, 15.1 Hz, Ar$_F$—C$_{meta}$), 146.1 (d, J=242.1 Hz, Ar$_F$—C$_{ortho}$), 146.5 (d, J=243.7 Hz, Ar$_F$—C$_{ortho}$), 152.8 (11,14-α-C$_{Pyrrole}$), 170.2 (1,4-α-C$_{Pyrrole}$) ppm.

$^{19}$F-NMR (376 MHz, acetone-d$_6$): δ=−142.21 (dd, J=23.8, 8.2 Hz, 4F, Ar—F$_{ortho}$), −142.61 (dd, J=21.7, 6.7 Hz, 4F, Ar—F$_{ortho}$), −157.86 (dd, J=22.6, 8.8 Hz, 4F, Ar—F$_{meta}$), −158.66 (dd, J=25.2, 9.2 Hz, 4F, Ar—F$_{meta}$) ppm.

HRMS (ESI-TOF): m/z calc. for C$_{56}$H$_{41}$F$_{16}$N$_4$O$_{12}$ [M+H]$^+$: 1265.2465; found: 1265.2490.

UV-VIS (Acetone), λ$_{max}$ [log ε(L·mol$^{-1}$·cm$^{-1}$)]: 408.5 (5.12), 504 (4.13), 600 (3.61), 653 (4.56) nm.

2.2 Preparation of 5,15-bis(3-hydroxyphenyl)-10,20-bis[2,3,5,6-tetrafluoro-4-(2,3-dihydroxypropyloxy)-phenyl]-chlorin In a typical experiment, all steps were performed under argon atmosphere. In a 250 ml three-necked flask p-toluenesulfonyl hydrazide (150.0 mg, 0.80 mmol), 5,15-bis(3-hydroxyphenyl)-10,20-bis[2,3,5,6-tetrafluoro-4-(2,3-dihydroxypropyloxy)-phenyl]porphyrin (234 mg, 0.185 mmol) and K$_2$CO$_3$ (400 mg, 2.89 mmol) were dissolved in 25.0 ml pyridine and stirred for 20 min at RT. Afterwards the reaction mixture was heated to 105° C. Additional p-toluenesulfonyl hydrazide (150.0 mg, 0.80 mmol) in 1.0 ml pyridine was added after 2 and 4 h. After 6.5 h heating 168 ml ethyl acetate and 84 ml H$_2$O were added and the reaction mixture was refluxed for 1 h at 100° C. The organic layer was washed with 168 ml 2 M HCl, 168 ml H$_2$O and 168 ml saturated NaHCO$_3$ solution, afterwards dried with Na$_2$SO$_4$ and evaporated to dryness. Then, the solid was dissolved in ethyl acetate (100 ml) and tetrachloro-o-benzoquinone (in a total of 167 mg, 0.68 mmol) was added in small portions (20 mg) every 15 min at RT to the stirring solution until the band at 735 nm in the UV/Vis spectrum just disappeared. The organic layer was washed twice with 168 ml 5% NaHSO$_3$ solution, once with 224 ml 0.01 M NaOH and once with 180 ml saturated NaHCO$_3$ solution and afterwards dried with Na$_2$SO$_4$. The product was evaporated to dryness and purified by reversed phase column chromatography (MeOH/H$_2$O=9:1) to obtain the product as a purple solid (240 mg, 0.246 mmol, 74%).

5,15-Bis(3-hydroxyphenyl)-10,20-bis[2,3,5,6-tetrafluoro-4-(2,3-dihydroxypropyloxy)-phenyl]-chlorin

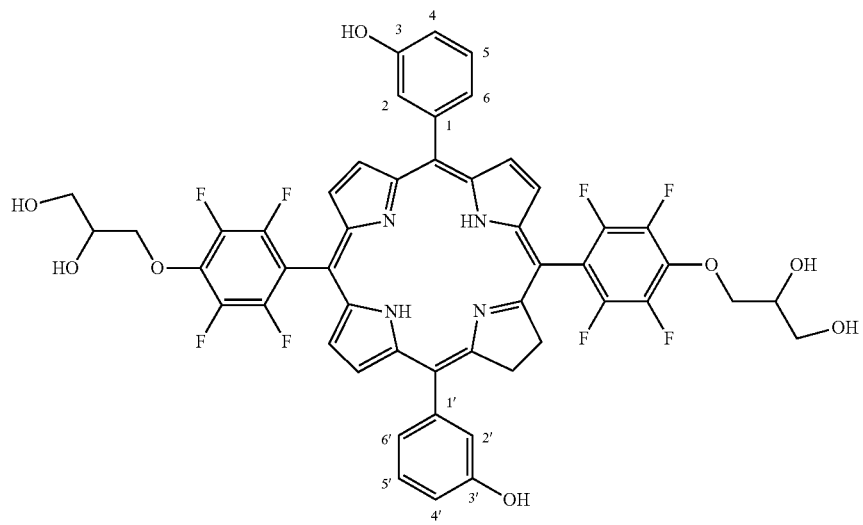 [SMILES: OCC(O)COc1c(F)c(F)c(-c2c3nc(c(-c4cccc(O)c4)c4ccc([nH]4)c(-c4c(F)c(F)c(OCC(O)CO)c(F)c4F)c4nc(c(-c5cccc(O)c5)c5ccc2[nH]5)CC4)C=C3)c(F)c1F]

$^1$H-NMR (500 MHz, acetone-d$_6$): δ=−1.51 (s, 1H, NH), −1.35 (s, 1H, NH), 3.75-3.86 (m, 4H, CH$_2$OH), 3.93-4.11 (m, 2H, CH—OH), 4.14-4.23 (m, 2H, OCH$_2$CH), 4.27-4.33 (m, 2H, 3-β-H$_{Pyrrole}$), 4.34-4.44 (m, 4H, 2-β-H$_{Pyrrole}$+CH$_2$OH), 4.52-4.61 (m, 2H, Ar$_F$—OCH$_2$), 4.63-4.71 (m, 2H, Ar$_F$—OCH$_2$), 7.19- 7.22 (m, 1H, Ar—H-6'), 7.25-7.29 (m, 1H, Ar—H-6), 7.41-7.44 (m, 1H, Ar—H-4'), 7.45-7.47 (m, 1H, Ar—H-2'), 7.55-7.60 (m, 2H, Ar—H-5+Ar—H-5'), 7.60-7.62 (m, 1H, Ar—H-4), 7.63-7.65 (m, 1H, Ar—H-2), 8.42 (d, J=5.0 Hz, 1H, β-H$_{Pyrrole}$), 8.53-8.58 (m, 3H, β-H$_{Pyrrole}$), 8.78 (d, J=4.9 Hz, β-H$_{Pyrrole}$), 8.85 (br s, 1H, Ar—OH), 8.89 (br s, 1H, Ar—OH), 8.91 (d, J=5.1 Hz, 1H, β-H$_{Pyrrole}$) ppm.

$^{13}$C-NMR (126 MHz, acetone-d$_6$): δ=34.7 (3-β-C$_{Pyrrole}$), 35.7 (2-β-C$_{Pyrrole}$), 62.9 (CH$_2$OH), 63.0 (CH$_2$OH), 71.2 (OCH$_2$CH), 71.3 (OCH$_2$CH), 76.7 (Ar$_F$—OCH$_2$), 76.7 (Ar$_F$—OCH$_2$), 96.5 (5-Ar$_F$—C$_{meso}$), 104.9 (15-Ar$_F$—C$_{meso}$), 113.4 (20-Ar—C$_{meso}$), 114.2 (t, $^2J_{C—F}$=20.0 Hz, 15-Ar$_F$—C$_{ipso}$), 114.6 (t, $^2J_{C—F}$=20.4 Hz, 5-Arp-C$_{ipso}$), 115.0 (Ar—C-6'), 115.1 (Ar—C-6), 119.4 (Ar—C-2'), 121.2 (Ar—C-2), 122.0 (β-C$_{Pyrrole}$), 123.7 (Ar—C-4'), 124.2 (10-Ar—C$_{meso}$), 125.3 (β-C$_{Pyrrole}$), 125.6 (Ar—C-4), 127.5 (β-C$_{Pyrrole}$), 127.9 (Ar—C-5'), 129.0 (β-C$_{Pyrrole}$), 129.3 (Ar—C-5), 130.6 (β-C$_{Pyrrole}$), 133.5 (β-C$_{Pyrrole}$), 135.1 (α-C$_{Pyrrole}$), 135.3 (α- C$_{Pyrrole}$), 138.6-139.1 (m, 5-Ar$_F$—C$_{para}$+15-Ar$_F$—C$_{para}$), 139.4 (α-C$_{Pyrrole}$), 141.26 (dd, $^{1,2}J_{C—F}$=246.7, 15.7 Hz, Ar$_F$—C$_{meta}$), 141.3 (α-C$_{Pyrrole}$), 141.8 (dd, $^{1,2}J_{C—F}$=246.6, 15.1 Hz, Ar$_F$—C$_{meta}$), 142.6 (Ar—C-1'), 143.4 (Ar—C-1), 146.17 (d, $^1J_{C—F}$=238.6 Hz, Ar$_F$—C$_{ortho}$), 146.68 (d, $^1J_{C—F}$=242.3 Hz, Ar$_F$—C$_{ortho}$), 152.3 (α- C$_{Pyrrole}$), 152.7 (α-C$_{Pyrrole}$), 156.1 (Ar—C-3'), 157.3 (Ar—C-3), 167.8 (4-α-C$_{Pyrrole}$), 170.3 (1-α-C$_{Pyrrole}$) ppm.

$^{19}$F-NMR (376 MHz, acetone-d$_6$): δ=−142.28 (d, J=22.0 Hz, 2F, Ar—F$_{ortho}$), −142.71--142.94 (m, 2F, Ar—F$_{ortho}$), −158.14 (dd, J=23.7, 8.4 Hz, 2F, Ar—F$_{meta}$), −158.95 (d, J=22.1 Hz, 2F, Ar—F$_{meta}$) ppm.

HRMS (ESI-TOF): m/z calc. for C$_{50}$H$_{37}$F$_8$N$_4$O$_8$ [M+H]$^+$: 973.2484; found: 973.2490.

UV-VIS (Acetone), λ$_{max}$ [log ε(L·mol$^{-1}$·cm$^{-1}$)]: 411.5 (5.25), 510.5 (4.30), 537.5 (3.97), 599 (3.85), 653 (4.56) nm.

2.3 Preparation of 5,10,15-tris(3-hydroxyphenyl)-20-[2,3,5,6-tetrafluoro-4-(2,3-dihydroxypropyloxy)-phenyl]-chlorin In a typical experiment, all steps were performed under argon atmosphere. In a 250 ml three-necked flask p-toluenesulfonyl hydrazide (359.0 mg, 0.482 mmol), 5,10,15-tris(3-hydroxyphenyl)-20-[2,3,5,6-tetrafluoro-4-(2,3-dihydroxypropyloxy)-phenyl]-porphyrin (400 mg, 2.89 mmol) and K$_2$CO$_3$ (400 mg, 2.89 mmol) were dissolved in 25.0 ml pyridine and stirred for 20 min at RT. Afterwards the reaction mixture was heated to 105° C. Additional p-toluenesulfonyl hydrazide (359 mg, 1.93 mmol) in 1.0 ml pyridine was added after 2 and 4 h. After 6.5 h heating 168 ml ethyl acetate and 84 ml H$_2$O were added and the reaction mixture was refluxed for 1 h at 100° C. The organic layer was washed with 168 ml 2 M HCl, 168 ml H$_2$O and 168 ml saturated NaHCO$_3$ solution, afterwards dried with Na$_2$SO$_4$ and evaporated to dryness. Then, the solid was dissolved in ethyl acetate (100 ml) and tetrachloro-o-benzoquinone (in a total of 288 mg, 1.17 mmol) was added in small portions (20 mg) every 15 min at RT to the stirring solution until the band at 735 nm in the UV/Vis spectrum just disappeared. The organic layer was washed twice with 168 ml 5% NaHSO$_3$ solution, once with 224 ml 0.01 M NaOH and once with 180 ml saturated NaHCO$_3$ solution and afterwards dried with Na$_2$SO$_4$. The product was evaporated to dryness and purified by reversed phase column chromatography (acetone/hexane=3:2) to obtain the product as a purple solid (243 mg, 0.293 mmol, 60%).

5,10,15-Tris(3-hydroxyphenyl)-20-[2,3,5,6-tetrafluoro-4-(2,3-dihydroxypropyloxy)-phenyl]-chlorin

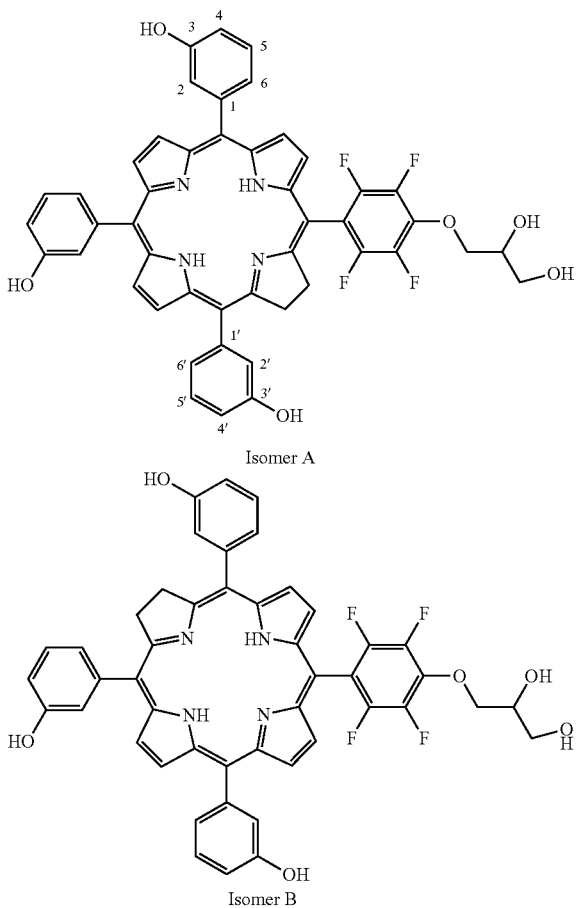

Isomer A

Isomer B $^1$H-NMR (500 MHz, acetone-d$_6$): δ=−1.69 (s, 1H, NH), −1.65 (s, 1H, NH), −1.33 (s, 1H, NH), −1.20 (s, 1H, NH), 3.75-3.85 (m, 2H, CH$_2$OH), 4.13-4.21 (m, 1H, OCH$_2$CH), 4.23-4.32 (m, 4H, 2,3-β-H$_{Pyrrole}$+12,13-β-H$_{Pyrrole}$), 4.51-4.60 (m, 1H, Ar$_F$—OCH$_2$), 4.62-4.71 (m, 1H, Ar$_F$—OCH$_2$), 7.17-7.19 (m, 1H, Ar—H-6'), 7.19-7.21 (m, 1H, Ar—H-6'), 7.23-7.25 (m, 1H, Ar—H-6), 7.25-7.29 (m, 1H, Ar—H-6), 7.36-7.45 (m, 4H, Ar—H-2'+Ar—H-4'), 7.52-7.64 (m, 8H, Ar—H), 8.30 (d, J=4.9 Hz, 1H, β-H$_{Pyrrole}$), 8.35 (d, J=4.9 Hz, 1H, β-H$_{Pyrrole}$), 8.40 (d, J=5.0 Hz, 1H, β-H$_{Pyrrole}$), 8.42-8.45 (m, 2H, β-H$_{Pyrrole}$), 8.48 (d, J=4.9 Hz, 1H, β-H$_{Pyrrole}$), 8.54 (d, J=4.5 Hz, 1H, β-H$_{Pyrrole}$), 8.57 (d, J=4.5 Hz, 1H, β-H$_{Pyrrole}$), 8.69 (d, J=4.9 Hz, 1H, β- H$_{Pyrrole}$), 8.73 (d, J=4.8 Hz, 1H, β-H$_{Pyrrole}$), 8.83 (br s, 3H, Ar—OH), 8.88 (d, J=4.9 Hz, 1H, β-H$_{Pyrrole}$) ppm.

$^{13}$C-NMR (126 MHz, acetone-d$_6$): δ=34.7 (β-C$_{Pyrrole}$), 35.3 (β-C$_{Pyrrole}$), 35.4 (β-C$_{Pyrrole}$), 35.6 (β-C$_{Pyrrole}$), 62.9 (CH$_2$OH), 71.2 (OCH$_2$CH), 76.7 (Ar$_F$—OCH$_2$), 112.5 (Ar—C$_{meso}$), 113. (Ar—C$_{meso}$), 113.5 (Ar—C$_{meso}$), 114.6 (Ar$_F$—C$_{ipso}$), 114.7-115.1 (m, Ar—C-6'+Ar—C-6), 119.4

(Ar—C-2'), 121.2 (Ar—C-2), 121.7 (β-$C_{Pyrrole}$), 122.8 (Ar—C), 123.4 (Ar—$C_{meso}$), 123.5-123.9 (m, β-$C_{Pyrrole}$+Ar—C-4'), 124.8 (β-$C_{Pyrrole}$), 125.5 (Ar—C-4), 125.6 (Ar—C), 126.6 (β-$C_{Pyrrole}$), 127.8 (Ar—C-5'), 128.0 (β-$C_{Pyrrole}$), 128.7 (β-$C_{Pyrrole}$), 128.8 (β-$C_{Pyrrole}$), 129.2 (Ar—C-5), 130.3 (β-$C_{Pyrrole}$), 132.0 (β-$C_{Pyrrole}$), 132.2 (β-$C_{Pyrrole}$), 133.1 (β-$C_{Pyrrole}$), 134.8 (α-$C_{Pyrrole}$), 134.8 (α-$C_{Pyrrole}$), 135.1 (α-$C_{Pyrrole}$), 135.2 (α-$C_{Pyrrole}$), 139.6 (α-$C_{Pyrrole}$), 141.3 (α-$C_{Pyrrole}$), 140.3 (α-$C_{Pyrrole}$), 140.4 (α-$C_{Pyrrole}$), 141.3 (α-$C_{Pyrrole}$), 142.9 (Ar—C-1'), 143.0 (Ar—C-1'), 143.0 (Ar—C-1), 143.8 (Ar—C-1), 143.8 (Ar—C), 144.1 (α-$C_{Pyrrole}$), 151.8 (α-$C_{Pyrrole}$), 152.4 (α-$C_{Pyrrole}$), 152.5 (α-$C_{Pyrrole}$), 152.8 (α-$C_{Pyrrole}$), 156.0 (Ar—C-3'), 157.2 (Ar—C-3), 167.6 (α-$C_{Pyrrole}$), 167.8 (α-$C_{Pyrrole}$), 168.8 (α-$C_{Pyrrole}$), 168.9 (α-$C_{Pyrrole}$) ppm.

$^{19}$F-NMR (376 MHz, acetone-$d_6$): δ=−142.14−−142.34 (m, 2F, Ar—$F_{ortho}$), −142.71−−142.94 (m, 2F, Ar—$F_{ortho}$), −158.15−−158.36 (m, 2F, Ar—$F_{meta}$), −159.07 (d, J=20.6 Hz, 2F, Ar—$F_{meta}$) ppm.

HRMS (ESI-TOF): m/z calc. for $C_{47}H_{35}F_4N_4O_6$ [M+H]$^+$: 827.2493; found: 827.2484.

UV-VIS (Acetone), $\lambda_{max}$ [log ε(L·mol$^{-1}$·cm$^{-1}$)]: 416.5 (5.11), 515 (4.27), 542 (4.02), 599 (3.84), 652.5 (4.52) nm.

Example 3

Preparation of 2,3-Dihydroxy-Propyloxy-Substituted Cis-Dihydroxy-Chlorins 3.1 Preparation of 2,3-dihydroxy-5,10,15,20-tetrakis [2,3,5,6-tetrafluoro-4-(2,3-dihydroxypropyloxy)-phenyl]-chlorin In a typical experiment, all steps were performed under argon atmosphere. In a 250 ml three-necked flask 5,10,15,20-tetrakis [2,3,5,6-tetrafluoro-4-(2,3-dihydroxypropyloxy)-phenyl]-porphyrin (413 mg, 0.237 mmol) was dissolved in 15.0 ml pyridine, $OsO_4$ (100 mg, 0.393 mmol) added and the mixture stirred for 18 hours at RT. Then, $Na_2SO_3$ (1.0 g in a saturated solution of $H_2O$/MeOH=1:1) was added and the mixture stirred again over night at room temperature. The mixture was then poured over celite, washed off with MeOH, evaporated to dryness, dissolved in ethyl acetate and washed three times with water. The organic phase was dried over sodium sulfate, then the drying agent was removed and the organic phase evaporated to dryness. The product was purified by column chromatography (ethyl acetate/MeOH=17:3) and recrystallization (acetone/hexane) to obtain the product as a purple solid (142 mg, 0.112 mmol, 34%).

2,3-Dihydroxy-5,10,15,20-tetrakis[2,3,5,6-tetrafluoro-4-(2,3-dihydroxypropyloxy)-phenyl]-chlorin

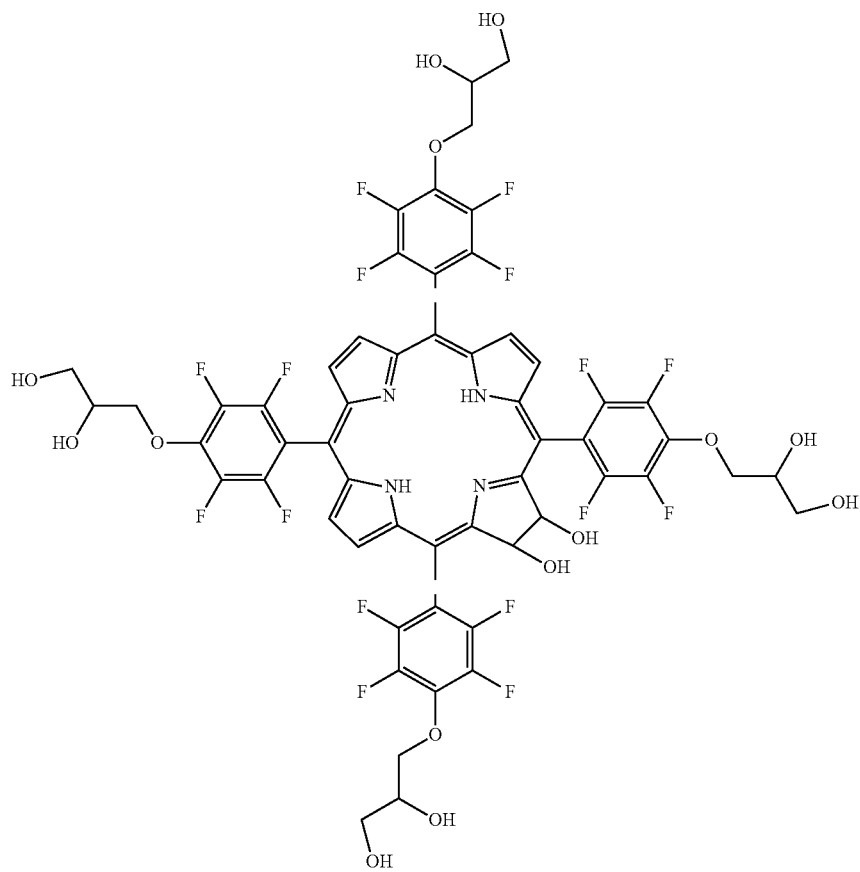 [SMILES: OCC(O)COc1c(F)c(F)c(-c2c3nc(c(-c4c(F)c(F)c(OCC(O)CO)c(F)c4F)c4ccc([nH]4)c(-c4c(F)c(F)c(OCC(O)CO)c(F)c4F)c4nc(c(-c5c(F)c(F)c(OCC(O)CO)c(F)c5F)c5ccc2[nH]5)C(O)C4O)C=C3)c(F)c1F]

$^1$H-NMR (500 MHz, acetone-$d_6$): δ=−1.96 (s, 2H, NH), 3.77-3.85 (m, 8H, CH$_2$OH), 3.97-4.02 (m, 4H, CH$_2$—OH), 4.14-4.24 (m, 4H, OCH$_2$CH), 4.37 (t, J=5.6 Hz, 4H, CHOH), 4.54 (dd, J=10.2, 6.2 Hz, 2H, Ar$_F$—OCH$_2$), 4.59 (dd, J=10.2, 6.2 Hz, 2H, Ar$_F$—OCH$_2$), 4.65 (dd, J=10.1, 4.4 Hz, 2H, Ar$_F$—OCH$_2$), 4.70 (dd, J=10.1, 4.4 Hz, 2H, Ar$_F$—OCH$_2$), 5.41 (dd, J=5.2, 1.9 Hz, 2H, 2,3-β-H$_{Pyrrole}$), 6.35-6.39 (m, 2H, 2,3-β—OH), 8.80 (s, 2H, 12,13-β-H$_{Pyrrole}$), 8.88 (d, J=5.0 Hz, 2H, 7,18-β-H$_{Pyrrole}$), 9.10 (d, J=5.0 Hz, 2H, 8.17-β-H$_{Pyrrole}$) ppm.

$^{13}$C-NMR (126 MHz, acetone-$d_6$): δ=63.0 (CH$_2$OH), 71.2 (OCH$_2$CH), 71.3 (OCH$_2$CH), 73.4 (2,3-β-H$_{Pyrrole}$), 76.7 (Ar$_F$—OCH$_2$), 99.4 (5,20-Ar$_F$—C$_{meso}$), 106.7 (10,15,-Ar$_F$—C$_{meso}$), 113.3 (t, $^2$J$_{C−F}$=19.8 Hz, 10,15-Ar$_F$—C$_{ipso}$), 113.6 (t, $^2$J$_{C−F}$=20.3 Hz, 5,20-Ar$_F$—C$_{ipso}$), 124.9 (7,18-β-C$_{Pyrrole}$), 128.6 (8,17-β-C$_{Pyrrole}$), 133.0 (12,13-β-H$_{Pyrrole}$), 135.8 (9,16-α-C$_{Pyrrole}$), 138.8 (Ar$_F$—C$_{para}$), 139.3 (Ar$_F$—C$_{para}$), 140.6 (6,19-α-C$_{Pyrrole}$), 141.4 (d, J=246.4 Hz, Ar$_F$—C$_{meta}$), 146.1 (d, J=244.3, Ar$_F$—C$_{ortho}$), 146.7 (d, J=241.7 Hz, Ar$_F$—C$_{ortho}$), 147.4 (d, J=242.6 Hz, Ar$_F$—C$_{ortho}$), 153.3 (11,14-α-C$_{Pyrrole}$), 165.6 (1,4-α-C$_{Pyrrole}$) ppm.

$^{19}$F-NMR (376 MHz, acetone-$d_6$): δ=−138.54--138.72 (m, 2F, Ar—F$_{ortho}$), −142.15 (dd, J=23.7, 8.3 Hz, 2F, Ar—F$_{ortho}$), −142.25 (dd, J=23.7, 8.2 Hz, 2F, Ar—F$_{ortho}$), −143.75 (dd, J=23.3, 8.1 Hz, 2F, Ar—F$_{ortho}$), −158.61--158.87 (m, 4F, Ar—F$_{meta}$), −159.30--159.63 (m, 4F, Ar—F$_{meta}$) ppm.

HRMS (ESI-TOF): m/z calc. for C$_{56}$H$_{41}$F$_{16}$N$_4$O$_{14}$ [M+H]$^+$: 1297.2364; found: 1297.2345.

UV-VIS (MeOH), λ$_{max}$ [log ε(L·mol$^{-1}$·cm$^{-1}$)]: 400 (5.15), 503 (4.22), 527.5 (3.87), 594 (3.78), 646 (4.51).

3.2 Preparation of 2,3-dihydroxy-5,15-bis(3-hydroxyphenyl)-10,20-bis[2,3,5,6-tetrafluoro-4-(2,3-dihydroxypropyloxy)-phenyl]-chlorin In a typical experiment, all steps were performed under argon atmosphere. In a 250 ml three-necked flask 5,15-bis(3-hydroxyphenyl)-10,20-bis[2,3,5,6-tetrafluoro-4-(2,3-dihydroxypropyloxy)-phenyl]porphyrin (185 mg, 0.190 mmol) was dissolved in 15.0 ml pyridine, OsO$_4$ (50 mg, 0.196 mmol) added and the mixture stirred for 18 hours at RT. Then, Na$_2$SO$_3$ (1.0 g in a saturated solution of H$_2$O/MeOH=1:11) was added and the mixture stirred again over night at room temperature. The mixture was then poured over celite, washed off with MeOH, evaporated to dryness, dissolved in ethyl acetate and washed three times with water. The organic phase was dried over sodium sulfate, then the drying agent was removed and the organic phase evaporated to dryness. The product was purified by reversed phase column chromatography (MeOH/H$_2$O=9:1) and recrystallization (acetone/hexane and washed with DCM) to obtain the product as a purple solid (72 mg, 71.6 μmol, 38%).

2,3-Dihydroxy-5,15-bis(3-hydroxyphenyl)-10,20-bis[2,3,5,6-tetrafluoro-4-(2,3-dihydroxypropyloxy)-phenyl]-chlorin

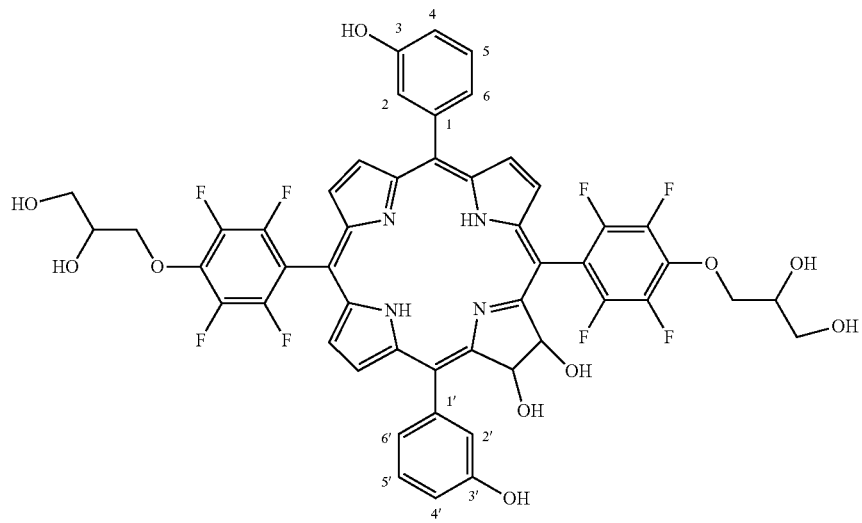 [SMILES: OCC(O)COc1c(F)c(F)c(-c2c3nc(c(-c4cccc(O)c4)c4ccc([nH]4)c(-c4c(F)c(F)c(OCC(O)CO)c(F)c4F)c4nc(c(-c5cccc(O)c5)c5ccc2[nH]5)C(O)C4O)C=C3)c(F)c1F]

$^1$H-NMR (500 MHz, acetone-$d_6$): δ=−1.90 (s, 1H, NH), −1.79 (s, 1H, NH), 3.75-3.85 (m, 4H, CH$_2$OH), 3.96 (d, J=6.3 Hz, 2H, CH—OH), 4.13-4.25 (m, 2H, OCH$_2$CH), 4.28-4.40 (m, 2H, CH$_2$OH), 4.52 (dd, J=10.1, 6.2 Hz, 2H, Ar$_F$—OCH$_2$), 4.58 (dd, J=10.1, 4.5 Hz, 2H, Ar$_F$—OCH$_2$), 4.63 (dd, J=10.1, 4.5 Hz, 2H, Ar$_F$—OCH$_2$), 4.69 (dd, J=10.2, 4.4 Hz, 2H, Ar$_F$—OCH$_2$), 4.93-4.98 (m, 2,3-β-OH), 5.02-5.12 (m, 2,3-β- OH), 6.23-6.33 (m, 1H, 2,3-β-H$_{Pyrrole}$), 6.37-6.43 (m, 2,3-β-H$_{Pyrrole}$), 7.17-7.22 (m, 1H, Ar—H-6'), 7.27-7.31 (m, 1H, Ar—H-6), 7.49-7.68 (m, 6H, Ar—H), 8.61 (d, J=5.0 Hz, 1H, β-H$_{Pyrrole}$), 8.66 (d, J=4.6 Hz, 1H, β-H$_{Pyrrole}$), 8.69 (br s, 1H, Ar—OH), 8.72 (d, J=5.0 Hz, β-H$_{Pyrrole}$), 8.82 (br s, 1H, Ar—OH), 8.87 (d, J=4.6 Hz, 1H, β-H$_{Pyrrole}$), 8.98 (d, J=5.0 Hz, 1H, β-H$_{Pyrrole}$) ppm.

$^{13}$C-NMR (126 MHz, acetone-$d_6$): δ=63.0 (CH$_2$OH), 71.2 (OCH$_2$CH), 71.3 (OCH$_2$CH), 72.4 (2,3-β-C$_{Pyrrole}$), 75.3 (2,3-β-C$_{Pyrrole}$), 76.7 (Ar$_F$—OCH$_2$), 76.7 (Ar$_F$—OCH$_2$), 98.1 (5-Ar$_F$—C$_{meso}$), 105.2 (15-Ar$_F$—C$_{meso}$), 113.4 (20-Ar—C$_{meso}$), 114.0 (m, 15-Ar$_F$—C$_{ipso}$), 114.4 (m, 5-Ar$_F$—C$_{ipso}$), 114.8 (Ar—C-6'), 114.9 (Ar—C-6'), 115.0 (Ar—C-6), 115.2 (Ar—C-6), 120.0 (Ar—C), 121.4 (Ar—C), 121.7

(Ar—C), 123.1 (β-$C_{Pyrrole}$), 123.7 (10-Ar—$C_{meso}$), 124.3 (Ar—C), 125.8 (Ar—C), 126.0 (β-$C_{Pyrrole}$), 127.1 (β-$C_{Pyrrole}$), 127.9 (Ar—C), 127.9 (Ar—C), 128.1 (Ar—C), 128.3 (Ar—C), 129.1 (β-$C_{Pyrrole}$), 130.5 (α-$C_{Pyrrole}$), 131.3 (β-$C_{Pyrrole}$), 132.9 (α-$C_{Pyrrole}$), 133.9 (β-$C_{Pyrrole}$), 135.4 (α-$C_{Pyrrole}$), 135.7 (α-$C_{Pyrrole}$), 138.3 ($Ar_F$—$C_{para}$), 139.8 (α-$C_{Pyrrole}$), 141.1-141.4 (m, $Ar_F$—$C_{meta}$), 141.4 (α-$C_{Pyrrole}$), 142.2 (Ar—C-1'), 142.2 (Ar—C-1), 142.5 (α-$C_{Pyrrole}$), 145.7 ($Ar_F$—$C_{ortho}$), 147.6 ($Ar_F$—$C_{ortho}$), 152.6 (α-$C_{Pyrrole}$), 153.4 (α-$C_{Pyrrole}$), 156.0 (Ar—C-3'), 156.3 (Ar—C-3), 164.33-164.61 (m, 1,4- α-$C_{pyrrole}$) ppm.

$^{19}$F-NMR (376 MHz, acetone-$d_6$): δ=−138.57 (dd, J=22.7, 10.1 Hz, 1F, Ar—$F_{ortho}$), −142.18 (d, J=23.3 Hz, 1F, Ar—$F_{ortho}$), −142.35 (d, J=23.1 Hz, 1F, Ar—$F_{ortho}$), −144.63-−144.84 (m, 1F, Ar—$F_{ortho}$), −158.80- −159.05 (m, 2F, Ar—$F_{meta}$), −159.78-−160.04 (m, 2F, Ar—$F_{meta}$) ppm.

HRMS (ESI-TOF): m/z calc. for $C_{50}H_{37}F_8N_4O_{10}$ [M+H]$^+$: 1005.2382, found: 1005.2372.

UV-VIS (MeOH), $λ_{max}$ [log ε(L·mol$^{-1}$·cm$^{-1}$)]: 409 (5.35), 509 (4.33), 537 (4.20), 594 (3.90), 648 (4.61).

3.3 Preparation of 2,3-dihydroxy-5,10,15-tris(3-hydroxyphenyl)-20-[2,3,5,6-tetrafluoro-4-(2,3-dihydroxypropyloxy)-phenyl]-chlorin In a typical experiment, all steps were performed under argon atmosphere. In a 250 ml three-necked flask 5,10,15-tris(3-hydroxyphenyl)-20-[2,3,5,6-tetrafluoro-4-(2,3-dihydroxypropyloxy)-phenyl]-porphyrin (490 mg, 0.594 mmol) was dissolved in 15.0 ml pyridine, OsO$_4$ (250 mg, 0.393 mmol) added and the mixture stirred for 18 hours at RT. Then, Na$_2$SO$_3$ (1.0 g in a saturated solution of H$_2$O/MeOH=1:1) was added and the mixture stirred again over night at room temperature. The mixture was then poured over celite, washed off with MeOH, evaporated to dryness, dissolved in ethyl acetate and washed three times with water. The organic phase was dried over sodium sulfate, then the drying agent was removed and the organic phase evaporated to dryness. The product was purified by column chromatography (ethyl acetate/MeOH=17:3) and recrystallization (acetone/hexane) to obtain the product as a purple solid (278 mg, 0.323 mmol, 54%).

2,3-Dihydroxy-5,10,15-tris(3-hydroxyphenyl)-20-[2,3,5,6-tetrafluoro-4-(2,3-dihydroxypropyloxy)-phenyl]-chlorin

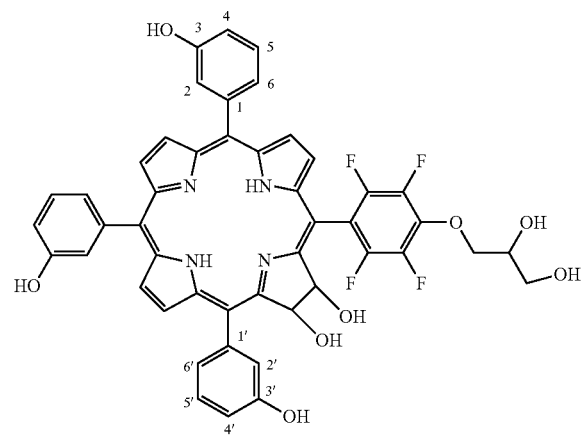 [SMILES: OCC(O)COc1c(F)c(F)c(-c2c3nc(c(-c4cccc(O)c4)c4ccc([nH]4)c(-c4cccc(O)c4)c4nc(c(-c5cccc(O)c5)c5ccc2[nH]5)C=C4)C(O)C3O)c(F)c1F]

$^1$H-NMR (500 MHz, acetone-$d_6$): δ=−1.67 (s, 1H, NH), −1.60 (s, 1H, NH), 3.76-3.85 (m, 2H, CH$_2$OH), 4.04 (br s, 1H, CH$_2$OH), 4.12-4.22 (m, 1H, OCH$_2$CH), 4.35-4.45 (br s, 1H, CH—OH), 4.52 (dd, J=10.1, 6.1 Hz, 1H, $Ar_F$—OCH$_2$), 4.63 (dd, J=10.1, 4.5 Hz, 1H, $Ar_F$—OCH$_2$), 4.94 (d, J=6.1 Hz, 2,3-β-OH), 5.04 (d, J=6.0 Hz, 1H, 2,3-β-OH), 6.18-6.28 (m, 1H, 2,3-β-$H_{Pyrrole}$), 6.34-6.40 (m, 1H, 2,3-β-$H_{Pyrrole}$), 7.15-7.20 (m, 1H, Ar—H-6'), 7.24-7.29 (m, 2H, Ar—H-6), 7.46-7.71 (m, 9H, Ar—H), 8.42 (d, J=4.9 Hz, 1H, β-$H_{Pyrrole}$), 8.52 (s, 2H, β-$H_{Pyrrole}$), 8.66 (d, J=5.0 Hz, 1H, 7-β-$H_{Pyrrole}$), 8.73 (br s, 1H, Ar—OH), 8.76 (d, J=4.9 Hz, 1H, β-$H_{Pyrrole}$), 8.78 (br s, 1H, Ar—OH), 8.82 (d, J=4.9 Hz, 1H, 8-β-$H_{Pyrrole}$) 8.86-8.96 (m, 1H, Ar—OH) ppm.

$^{13}$C-NMR (126 MHz, acetone-$d_6$): δ=63.0 (CH$_2$OH), 71.2 (OCH$_2$CH), 72.3 (2,3-β-$C_{Pyrrole}$), 75.5 (2,3-β-$C_{Pyrrole}$), 76.6 ($Ar_F$—OCH$_2$), 96.7 (5-$Ar_F$—$C_{meso}$), 114.3 (20-Ar—$C_{meso}$), 114.5 ($Ar_F$—$C_{ipso}$), 114.6 (Ar—C-6'), 115.1 (Ar—C-6), 120.0 (Ar—C), 121.3 (Ar—C), 121.4 (Ar—C), 121.7 (Ar—C), 122.7 (7-β-$C_{Pyrrole}$), 123.3 (Ar—$C_{meso}$), 123.8 (Ar—$C_{meso}$), 124.2 (Ar—C), 124.7 (β-$C_{Pyrrole}$), 125.6 (Ar—C), 125.7 (Ar—C), 126.0 (Ar—C), 127.8 (Ar—C), 127.9 (Ar—C), 128.1 (Ar—C), 128.2 (Ar—C), 128.4 (β-$C_{Pyrrole}$), 128.9 (β-$C_{Pyrrole}$), 132.5 (β-$C_{Pyrrole}$), 132.7 (β-$C_{Pyrrole}$), 135.3 (α-$C_{Pyrrole}$), 135.4 (α-$C_{Pyrrole}$), 138.2 ($Ar_F$—$C_{para}$), 140.0 (α-$C_{Pyrrole}$), 141.2 (α-$C_{pyrrole}$), 141.4 (d, $^1J_{C—F}$=245.5 Hz, $Ar_F$—$C_{meta}$), 142.5 (Ar—C-1'), 142.6 (Ar—C-1'), 142.8 (Ar—C-1), 142.9 (Ar—C-1), 146.31 (d, J=241.9 Hz, $Ar_F$—$C_{ortho}$), 147.20 (d, J=241.2 Hz, $Ar_F$—$C_{ortho}$), 153.0 (α-$C_{Pyrrole}$), 153.1 (α-$C_{Pyrrole}$), 156.1 (Ar—C-3'), 156.3 (Ar—C-3), 156.5 (Ar—C-3), 163.3 (α-$C_{Pyrrole}$), 164.4 (1,4- α-$C_{Pyrrole}$) ppm.

$^{19}$F-NMR (376 MHz, acetone-$d_6$): δ=−138.45-−138.63 (m, 2F, Ar—$F_{ortho}$)), −144.57-−144.85 (m, 2F, Ar—$F_{ortho}$), −159.83-−160.13 (m, 2F, Ar—$F_{meta}$) ppm.

HRMS (ESI-TOF): m/z calc. for $C_{47}H_{35}F_4N_4O_8$ [M+H]$^+$: 859.2351, found: 859.2837.

UV-VIS (MeOH), $λ_{max}$ [log ε(L·mol$^{-1}$·cm$^{-1}$)]: 405 (5.19), 511.5 (4.37), 538.5 (4.07), 592 (3.72), 644.5 (4.40).

Example 4

Preparation of 3-Hydroxyphenyl- and Alkyl-, Hydroxyalkyl, or Fluoroalkyl-Substituted Porphyrins

4.1. Preparation of 5,10,15,20-tetrakis-[4-(4-hydroxybutyloxy)-2,3,5,6-tetrafluorophenyl]-porphyrin In a typical experiment, 5,10,15,20-tetrakis(pentafluorophenyl)-porphyrin (110 mg, 113 μmol) was dissolved in dry THF under argon atmosphere, KOH (1.43 g, 23.8 mmol) and butane-1,4-diol (2.0 ml, 22.64 mmol) were added and the reaction mixture stirred under room temperature for 18 hours. After aqueous workup, extraction with DCM and drying with Na$_2$SO$_4$, the crude product was purified by column chromatography (DCM/MeOH=9:1) and recrystallized (DCM/hexane) to obtain a purple solid (110 mg, 78%).

5,10,15,20-Tetrakis-[4-(4-hydroxybutyloxy)-2,3,5,6-tetrafluorophenyl]-porphyrin

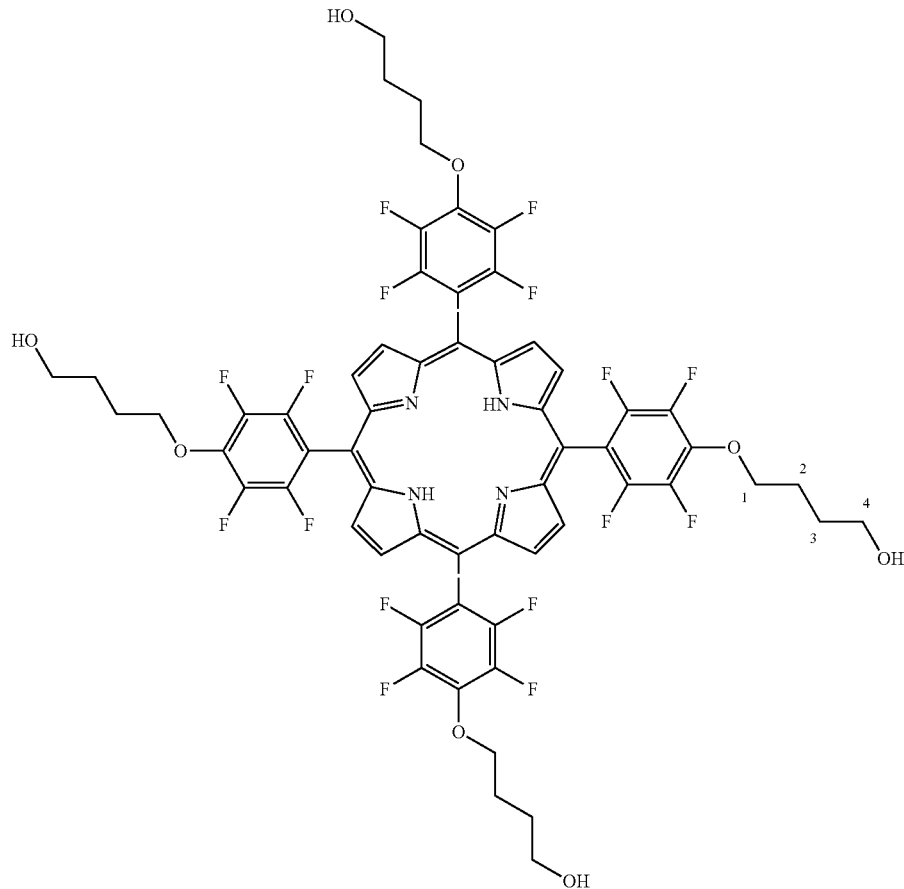 [SMILES: OCCCCOc1c(F)c(F)c(-c2c3nc(c(-c4c(F)c(F)c(OCCCCO)c(F)c4F)c4ccc([nH]4)c(-c4c(F)c(F)c(OCCCCO)c(F)c4F)c4nc(c(-c5c(F)c(F)c(OCCCCO)c(F)c5F)c5ccc2[nH]5)C=C4)C=C3)c(F)c1F]

$^1$H-NMR (500 MHz, acetone-d$_6$): δ=−2.89 (s, 2H, NH), 1.84-1.90 (m, 8H, H-3), 2.07-2.13 (m, 8H, H-2), 3.72-3.77 (m, 8H, H-4), 4.66 (t, J=6.5 Hz, 8H, H-1), 9.30 (s, 8H, β-H$_{Pyrrol}$) ppm.

$^{13}$C-NMR (126 MHz, acetone-d$_6$): δ=26.8 (C-2), 29.0 (C-3), 61.2 (C-4), 75.7 (C-1), 104.6 (Ar$_F$—C$_{meso}$), 113.4 (t, $^2J_{C-F}$=19.7 Hz, Ar$_F$—C$_{ipso}$), 139.2 (Ar$_F$—C$_{para}$), 141.56 (dd, $^{1,2}J_{C-F}$=246.6, 15.1 Hz, Ar$_F$—C$_{meta}$) 146.98 (d, $^1J_{C-F}$=244.2 Hz, Ar$_F$—C$_{ortho}$) ppm.

$^{19}$F-NMR (376 MHz, acetone-d$_6$): δ=−141.97 (dd, J=21.5, 7.4 Hz, 8F, Ar—F$_{ortho}$), −159.52 (dd, J=21.9, 7.5 Hz, 8F, Ar—F$_{meta}$) ppm.

HRMS (ESI-TOF): m/z calc. for C$_{60}$H$_{47}$F$_{16}$N$_4$O$_8$ [M+H]$^+$: 1255.3133; found: 1255.3123.

UV/Vis (DCM), λ$_{max}$/nm (lg ε/L·mol$^{-1}$·cm$^{-1}$): 413.5 (5.47), 507.5 (5.35), 585 (3.90), 655 (3.27)

4.2. Preparation of 5,10,15-tris-(3-hydroxyphenyl)-20-pentafluorophenyl-porphyrin In a typical experiment, 5,10,15-tris-(3-acetoxyphenyl)-20-pentafluorophenyl-porphyrin (164 mg, 187 μmol) was dissolved in acetone (4 ml), a mixture of THF (1 ml), H$_2$O (1 ml) and KOH (420 mg, 7.49 mmol) was added and the reaction mixture stirred under room temperature for 2 hours. After aqueous workup, extraction with ethyl acetate and drying with Na$_2$SO$_4$, the crude product was purified by column chromatography (DCM/acetone=9:1) and recrystallized [DCM/(MeOH/H$_2$O=9:1)] to obtain a purple solid (127 mg, 169 μmol, 90%).

5,10,15-Tris-(3-hydroxyphenyl)-20-pentafluorophenyl-porphyrin

5,10,15-Tris-(3-hydroxyphenyl)-20-[4-(butyloxy)-tetra-fluorophenyl]-porphyrin

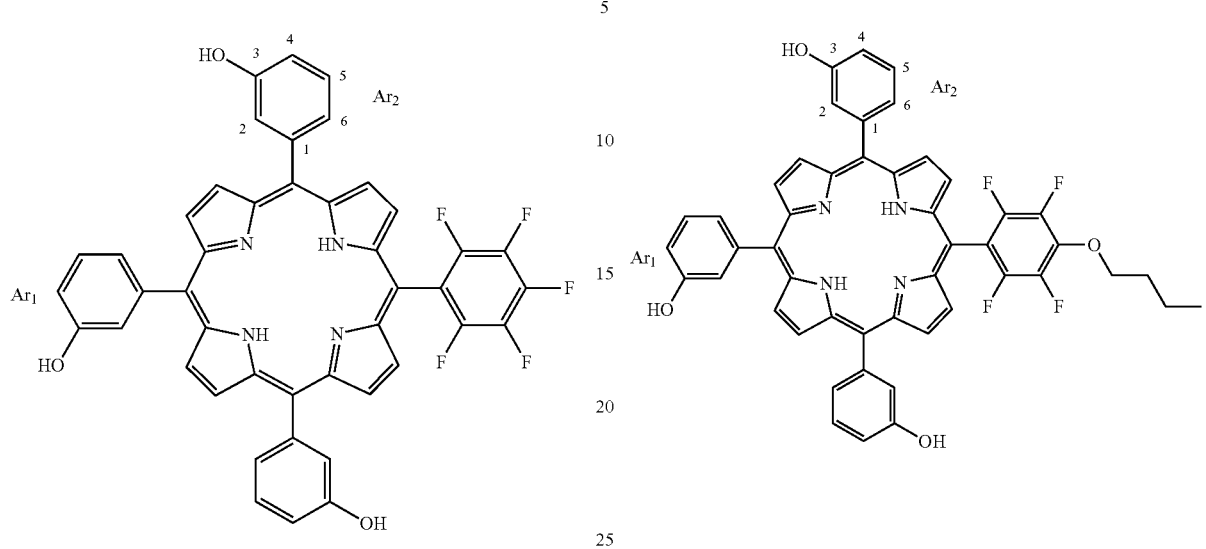

$^1$H-NMR (700 MHz, acetone-$d_6$): δ=−2.75 (s, 2H, NH), 7.33-7.35 (m, 3H, Ar—H-6), 7.61-7.65 (m, 3H, Ar—H-5), 7.71-7.74 (m, 3H, Ar—H-4), 7.75-7.77 (m, 3H, Ar—H-2), 8.98 (br s, 7H, β-$H_{Pyrrol}$+Ar—OH), 9.04 (d, J=3.6 Hz, 2H, 3,17-β-$H_{Pyrrol}$), 9.14 (br s, 2H, 2,18-β-$H_{Pyrrol}$) ppm.

$^{13}$C-NMR (176 MHz, acetone-$d_6$): 101.1 ($Ar_F$—$C_{meso}$), 116.0 (Ar—C-6), 117.2 ($Ar_F$—$C_{ipso}$), 121.7 (10-Ar—$C_{meso}$), 122.8 ($Ar_1$—C-2), 122.8 ($Ar_2$—C-2), 122.8 (15-Ar—$C_{meso}$), 127.1 ($Ar_1$—C-4), 127.2 ($Ar_2$—C-4), 128.6 ($Ar_1$C-5), 128.7 ($Ar_2$—C-5), 132.3 (7,8,12,13-β-$C_{Pyrrol}$), 138.1 ($Ar_F$—$C_{meta}$), 139.5 ($Ar_F$—$C_{meta}$), 142.4 ($Ar_F$—$C_{para}$), 143.6 ($Ar_2$—C-1), 143.8 ($Ar_1$—C-1), 147.0 ($Ar_F$—$C_{ortho}$), 148.3 ($Ar_F$—$C_{ortho}$), 156.8 ($Ar_1$—C-3), 156.8 ($Ar_2$—C-3) ppm.

$^{19}$F-NMR (376 MHz, acetone-$d_6$): δ=−140.32--140.50 (m, 2F, Ar—$F_{ortho}$), −156.58 (t, J=20.4 Hz, 1F, Ar—$F_{para}$), −164.34 (t, J=20.5, 2F, Ar—$F_{meta}$) ppm.

4.3. Preparation of 5,10,15-tris-(3-hydroxyphenyl)-20-[4-(butyloxy)-tetra-fluorophenyl]-porphyrin In a typical experiment, 5,10,15-tris(3-acetoxyphenyl)-20-(pentafluorophenyl)-porphyrin (60.3 mg, 68.6 μmol) was dissolved in dry DMSO under argon atmosphere, KOH (150 mg, 2.67 mmol) and 1-butanol (0.5 ml, 5.46 mmol) were added and the reaction mixture stirred under room temperature for 20 minutes. After aqueous workup, extraction with ethyl acetate and drying with $Na_2SO_4$, the crude product was purified by column chromatography (DCM/ethyl acetate=9:1) and recrystallized (DCM/hexane) to obtain a purple solid (47.7 mg, 59.1 μmol, 86%).

$^1$H-NMR (500 MHz, acetone-$d_6$): δ=−2.77 (s, 2H, NH), 1.08 (t, J=7.4 Hz, 3H, $CH_3$), 1.63-1.72 (m, 2H, $CH_2CH_3$), 1.94-2.01 (m, 2H, $OCH_2CH_2$), 4.61 (t, J=6.4 Hz, 2H, $OCH_2$), 7.31-7.35 (m, 3H, Ar—H-6), 7.62 ($m_c$, 1H, $Ar_1$—H-5), 7.63 ($m_c$, 2H, $Ar_2$—H-5), 7.69-7.78 (m, 6H, Ar—H-2+Ar—H-4), 8.92 (s, 8H, β-$H_{Pyrrole}$) ppm.

$^{13}$C-NMR (126 MHz, acetone-$d_6$): δ=13.2 ($CH_3$), 18.8 ($CH_2$), 32.0 ($CH_2$), 75.7 (t, $^4J_{C—F}$=2.9 Hz, $OCH_2$), 101.6 (s, $Ar_F$—$C_{meso}$), 114.5 (t, $^2J_{C—F}$=20.0 Hz, $Ar_F$—$C_{ipso}$), 115.2 (Ar—C-6), 120.7 (Ar—$C_{meso}$), 121.8 (Ar—$C_{meso}$), 122.0 ($Ar_1$—C-2), 122.0 ($Ar_2$—C-2), 126.3 ($Ar_1$—C-4), 126.4 ($Ar_2$—C-4), 127.8 ($Ar_1$—C-5), 127.8 ($Ar_2$—C-5), 138.8 ($Ar_F$—$C_{para}$), 141.5 (dd, $^{1,2}J_{C—F}$=246.5, 14.9 Hz, $Ar_F$—$C_{meta}$), 142.9 (Ar—$C_{ipso}$), 143.0 (Ar—$C_{ipso}$), 147.0 (d, $^1J_{C—F}$=247.1 Hz, $Ar_F$—$C_{ortho}$), 156.0 ($Ar_1$—C-3), 156.0 ($Ar_2$—C-3) ppm.

$^{19}$F-NMR (376 MHz, acetone-$d_6$): δ=−141.78 ($m_c$, 2F, Ar—$F_{ortho}$), −159.31 ($m_c$, 2F Ar—$F_{meta}$) ppm.

HRMS (ESI-TOF): m/z calc. for $C_{48}H_{35}F_4N_4O_4$ $[M+H]^+$: 807.2594; found: 807.2654.

UV-VIS (DCM), $λ_{max}$ [log ε(L·mol$^{-1}$·cm$^{-1}$)]: 417 (5.23), 513 (4.17), 546 (3.45), 588 (3.51), 643 (2.46) nm.

4.4. Preparation of 5,10,15-tris-(3-hydroxyphenyl)-20-[4-(2-hydroxy-ethyloxy)-tetra-fluorophenyl]-porphyrin In a typical experiment, 5,10,15-tris(3-acetoxyphenyl)-20-(pentafluorophenyl)-porphyrin (83.4 mg, 94.9 μmol) was dissolved in dry DMSO under argon atmosphere, KOH (300 mg, 5.34 mmol) and ethanediol (1.0 ml, 17.8 mmol) were added and the reaction mixture stirred under room temperature for 25 minutes. After aqueous workup, extraction with ethyl acetate and drying with $Na_2SO_4$, the crude product was purified by column chromatography (DCM/MeOH=9:1) and recrystallized (acetone/hexane) to obtain a purple solid (59.8 mg, 75.2 μmol, 80%).

5,10,15-Tris-(3-hydroxyphenyl)-20-[4-(2-hydroxyethyloxy)-tetra-fluorophenyl]-porphyrin

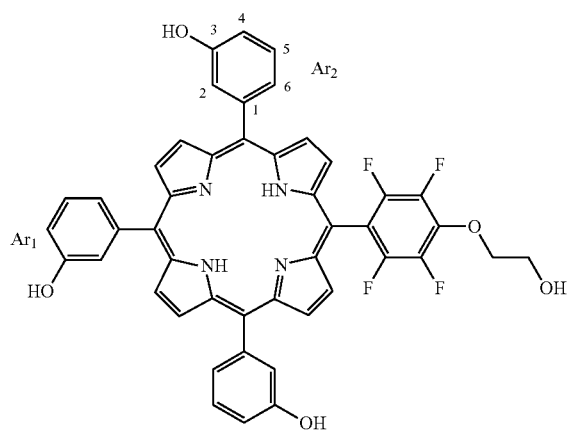

$^1$H-NMR: (500 MHz, acetone-$d_6$): δ=−2.76 (s, 2H, NH), 4.10 ($m_c$, 2H, $CH_2OH$), 4.26 (t, J=5.7 Hz, 1H, $CH_2OH$), 4.69 (t, J=4.8 Hz, 2H, $OCH_2$), 7.31-7.36 (m, 3H, Ar—H-6), 7.62 (t, J=7.8 Hz, 3H, Ar—H-5), 7.70-7.77 (m, 6H, Ar—H-2+Ar—H-4), 8.88 (s, 3H, Ar—OH), 8.86-9.30 (m, 8H, β-$H_{Pyrrole}$) ppm.

$^{13}$C-NMR: (126 MHz, acetone-$d_6$): δ=61.1 ($CH_2OH$), 61.3 ($CH_2OH$), 77.1 (t, $^4J_{C-F}$=2.8 Hz, $OCH_2$), 101.6 ($Ar_F$—$C_{meso}$), 114.6 (t, $^2J_{C-F}$=20.0 Hz, $Ar_F$—$C_{ipso}$), 115.1 ($Ar_1$C-6), 115.2 ($Ar_1$C-6), 120.7 (Ar—$C_{meso}$), 121.8 (Ar—$C_{meso}$), 121.9 ($Ar_1$C-2), 122.0 ($Ar_2$—C-2), 126.4 ($Ar_1$C-4), 126.4 ($Ar_2$—C-4), 127.8 ($Ar_2$—C-5), 127.9 ($Ar_1$C-5), 131.9 (β-$C_{Pyrrole}$), 133.1 (β-$C_{Pyrrole}$), 139.0 (t, $^2J_{C-F}$=12.7 Hz, $Ar_F$—$C_{para}$), 141.42 (dd, $^{1,2}J_{C-F}$=245.8, 15.4 Hz, $Ar_F$—$C_{meta}$), 142.9 (Ar—$C_{ipso}$), 143.1 (Ar—$C_{ipso}$), 146.87 (d, $^1J_{C-F}$=242.8 Hz, $Ar_F$—$C_{ortho}$), 155.8 (Ar—C-3), 155.9 (Ar—C-3), 156.0 (Ar—C-3) ppm.

$^{19}$F-NMR (376 MHz, acetone-$d_6$): δ=−141.82−−142.02 (m, 2F, Ar—$F_{ortho}$), −159.00 (d, J=22.1 Hz, 2F, Ar—$F_{meta}$) ppm.

HRMS (ESI-TOF): m/z calc. for $C_{46}H_{31}F_4N_4O_5$ [M+H]$^+$: 795.2231; found: 795.2288.

UV-VIS (DCM), $λ_{max}$ [log ε(L·mol$^{-1}$·cm$^{-1}$)]: 417 (5.25), 513 (4.27), 546 (3.80), 588 (3.82), 643 (3.52).

4.5. Preparation of 5,10,15-tris-(3-hydroxyphenyl)-20-[4-(3-hydroxy-propyloxy)-tetra-fluorophenyl]-porphyrin In a typical experiment, 5,10,15-tris(3-acetoxyphenyl)-20-(pentafluorophenyl)-porphyrin (72.4 mg, 81.9 μmol) was dissolved in dry DMSO under argon atmosphere, KOH (200 mg, 3.56 mmol) and 1,3-propanediol (600 ml, 8.27 mmol) were added and the reaction mixture stirred under room temperature for 25 minutes. After aqueous workup, extraction with ethyl acetate and drying with $Na_2SO_4$, the crude product was purified by column chromatography (DCM/MeOH=9:1) and recrystallized (acetone/hexane) to obtain a purple solid (57.9 mg, 71.5 μmol, 87%).

5,10,15-Tris-(3-hydroxyphenyl)-20-[4-(3-hydroxypropyloxy)-tetra-fluorophenyl]-porphyrin

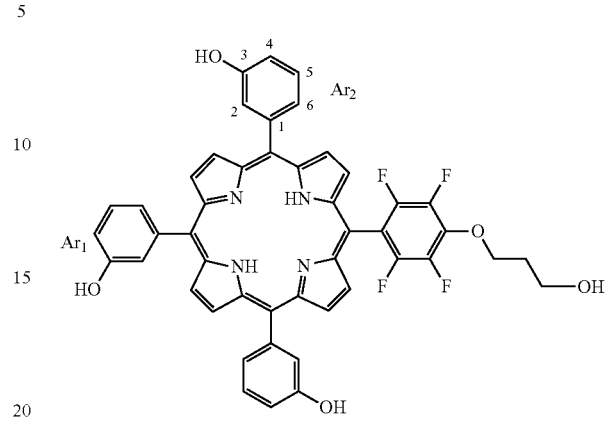

$^1$H-NMR: (500 MHz, acetone-$d_6$): δ=−2.77 (s, 2H, NH), 2.20 (p, J=6.3 Hz, 2H, $CH_2$), 3.92 (q, J=5.9 Hz, 2H, $CH_2OH$), 4.74 (t, J=6.3 Hz, 2H, $OCH_2$), 7.30-7.35 (m, 3H, Ar—H-6), 7.62 ($m_c$, 1H, $Ar_1$—H-5) 7.63 ($m_c$, 2H, $Ar_2$—H-5), 7.69-7.76 (m, 6H, Ar—H-2+Ar—H-4), 8.91 (s, 3H, Ar—OH), 8.92-9.15 (m, 8H, β-$H_{Pyrrole}$) ppm.

$^{13}$C-NMR: (126 MHz, acetone-$d_6$): δ=33.3 ($CH_2$), 57.7 ($CH_2OH$), 57.9 (t, $^4J_{C-F}$=3.2 Hz, $OCH_2$), 101.6 ($Ar_F$—$C_{meso}$), 114.4 (t, $^2J_{C-F}$=2.0 Hz, $Ar_F$—$C_{ipso}$), 115.1 ($Ar_1$—C-6), 115.2 ($Ar_2$—C—6), 120.7 (Ar—$C_{meso}$), 121.7 (Ar—$C_{meso}$), 121.9 ($Ar_1$—C-2), 122.0 ($Ar_2$—C-2), 126.4 ($Ar_1$—C-4), 126.4 ($Ar_2$—C-4), 127.8 ($Ar_2$—C-5), 127.8 ($Ar_1$—C5), 138.8 ($Ar_F$—$C_{para}$), 141.4 (dd, $^{1,2}J_{C-F}$=245.8, 15.4 Hz, $Ar_F$—$C_{meta}$), 142.9 (Ar—$C_{ipso}$), 143.1 (Ar—$C_{ipso}$), 1469 (d, $^1J_{C-F}$=242.8 Hz, $Ar_F$—$C_{ortho}$), 155.9 ($Ar_1$—C-3), 156.0 ($Ar_2$—C-3) ppm.

$^{19}$F-NMR (376 MHz, acetone-$d_6$) δ=−141.80 ($m_c$, 2F, Ar—$F_{ortho}$), −159.29 (d, J=21.9 Hz, 2F, Ar—$F_{meta}$) ppm.

HRMS (ESI-TOF): m/z calc. for $C_{47}H_{33}F_4N_4O_5$ [M+H]$^+$: 809.2387; found: 809.2454.

UV-VIS (MeOH), $λ_{max}$ [log ε(L·mol$^{-1}$·cm$^{-1}$)]: 414 (5.40), 511 (4.34), 544.5 (3.84), 587 (3.83), 643 (3.47).

4.6. Preparation of 5,10,15-tris(3-hydroxy-phenyl)-20-[2,3,5,6-tetra-fluoro-4-(1H,1H,5H-octafluoropentyloxy)-phenyl]-porphyrin In a typical experiment, 5,10,15-tris(3-acetoxyphenyl)-20-(pentafluorophenyl)-porphyrin (60.0 mg, 68.2 μmol) was dissolved in a dry DMSO/THF (4:1) mixture under argon atmosphere, KOH (103.4 mg, 1.84 mmol) and 1H,1H,5H-octafluoropentanol (342 ml, 2.46 mmol) were added and the reaction mixture stirred under room temperature for 30 minutes. After aqueous workup, extraction with ethyl acetate and drying with $Na_2SO_4$, the crude product was purified by column chromatography (DCM/MeOH=95:5) and recrystallized (DCM/hexane) to obtain a purple solid (58.4 mg, 60.5 μmol, 88%).

5,10,15-Tris(3-hydroxy-phenyl)-20-[2,3,5,6-tetra-fluoro-4-(1H,1H,5H-octafluoro-pentyloxy)-phenyl]-porphyrin

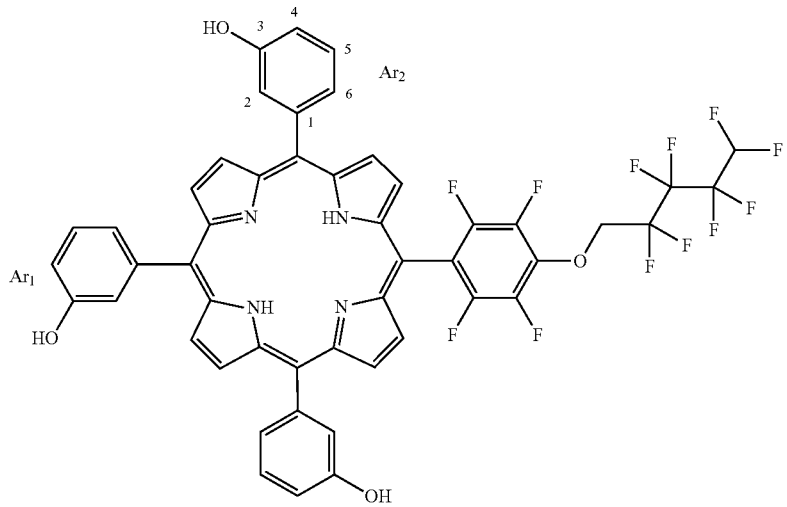

$^1$H-NMR (500 MHz, acetone-$d_6$): δ=−2.78 (s, 2H, NH), 5.32 (t, J=13.8 Hz, 2H, OCH$_2$), 6.93 (tt, J=50.9, 5.5 Hz, 3H, CF$_2$H), 7.30-7.34 (m, 3H, Ar—H-6), 7.62 (m$_c$, 1H, Ar$_1$—H-5), 7.62 (m$_c$, 2H, Ar$_2$—H-5), 7.68-7.78 (m, 6H, Ar—H-2+Ar—H-4), 8.80-9.28 (m, 8H, β-H$_{Pyrrol}$) ppm.

$^{13}$C-NMR (126 MHz, acetone-$d_6$): δ=70.3 (OCH$_2$), 100.9 (Ar$_F$—C$_{meso}$), 108.4 (CF$_2$H), 115.2 (Ar—C-6), 116.4 (Ar$_F$—C$_{ipso}$), 120.8 (Ar—C$_{meso}$), 121.9 (Ar—C$_{meso}$), 122.0 (Ar$_1$C-2), 122.0 (Ar$_2$—C-2), 126.3 (Ar$_1$C-4), 126.3 (Ar$_2$—C-4), 127.8 (Ar$_1$C-5), 127.8 (Ar$_2$—C-5), 137.4 (Ar$_F$—C$_{para}$), 141.4 (d, $^1J_{C—F}$=246.2 Hz, Ar$_F$—C$_{meta}$), 142.8 (Ar$_2$—C$_{ipso}$), 143.0 (Ar$_1$—C$_{ipso}$), 146.9 (d, $^1J_{C—F}$=241.0 Hz, Ar$_F$—C$_{ortho}$), 156.0 (Ar$_1$C-3), 156.0 (Ar$_2$—C-3) ppm.

$^{19}$F-NMR (376 MHz, acetone-$d_6$): δ=−121.25—−121.42 (m, 2F, CF$_2$), −125.24—−125.36 (m, 2F, CF$_2$), −130.48—−130.62 (m, 2F, CF$_2$), −138.95 (d, $^2J_{H—F}$=50.8 Hz, 2F, CF$_2$H), −140.83—−141.01 (m, 2F, Ar—F$_{ortho}$), −158.30—−158.48 (m, 2F, Ar—F$_{meta}$) ppm.

HRMS (ESI-TOF): m/z calc. for $C_{49}H_{29}F_{12}N_4O_4$ [M+H]$^+$: 965.1992; found: 965.2041

UV-VIS (acetone), λ$_{max}$ [log ε(L·mol$^{-1}$·cm$^{-1}$)]: 414 (5.37), 511 (4.41), 545 (4.04), 587 (4.08), 643 (3.84) nm.

4.7. Preparation of 5,10,15-tris(3-hydroxy-phenyl)-20-[2,3,5,6-tetra-fluoro-4-(1H,1H,7H-dodecafluoro-heptyloxy)-phenyl]-porphyrin In a typical experiment, 5,10,15-tris(3-acetoxyphenyl)-20-(pentafluorophenyl)-porphyrin (57.3 mg, 65.2 µmol) was dissolved in a dry DMSO/THF (4:1) mixture under argon atmosphere, KOH (98.7 mg, 1.76 mmol) and 1H,1H,7H-dodecafluoroheptanol (0.44 ml, 2.35 mmol) were added and the reaction mixture stirred under room temperature for 30 minutes. After aqueous workup, extraction with ethyl acetate and drying with Na$_2$SO$_4$, the crude product was purified by column chromatography (hexane/acetone=3:2) and recrystallized (MeOH/H$_2$O) to obtain a purple solid (46 mg, 43.2 µmol, 66%).

5,10,15-Tris(3-hydroxy-phenyl)-20-[2,3,5,6-tetra-fluoro-4-(1H,1H,7H-dodecafluoroheptyloxy)-phenyl]-porphyrin

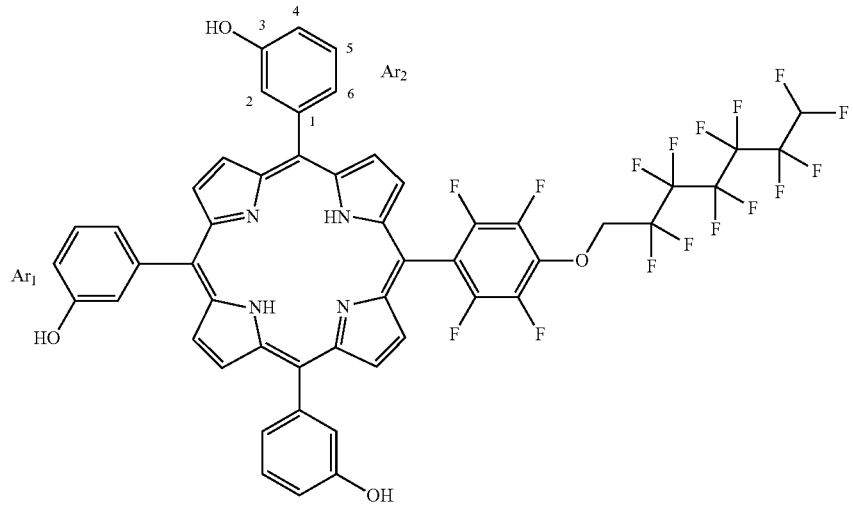

$^1$H-NMR (500 MHz, acetone-d$_6$): δ=−2.77 (s, 2H, NH), 5.36 (t, J=13.5 Hz, 2H, OCH$_2$), 6.93 (tt, J=50.9, 5.3 Hz, 3H, CF$_2$H), 7.30-7.35 (m, 3H, Ar—H-6), 7.62 (m$_c$, 1H, Ar$_1$—H-5), 7.63 (m$_c$, 2H, Ar$_2$—H-5), 7.70-7.76 (m, 6H, Ar—H-2+Ar—H-4), 8.88 (s, 3H, Ar—OH), 8.93-9.13 (m, 8H, β-H$_{Pyrrol}$) ppm.

$^{13}$C-NMR (126 MHz, acetone-d$_6$): δ=70.4 (t, $^2J_{C-F}$=27.5 Hz, OCH$_2$), 100.9 (Ar$_F$—C$_{meso}$), 115.2 (Ar—C-6), 116.5 (t, $^2J_{C-F}$=20 Hz, Ar$_F$C$_{ipso}$), 120.8 (Ar—C$_{meso}$), 121.9 (Ar—C$_{meso}$), 122.0 (Ar$_1$C-2), 122.0 (Ar$_2$—C-2), 126.3 (Ar$_1$—C-4), 126.4 (Ar$_2$—C-4), 127.8 (Ar$_1$C-5), 127.8 (Ar$_2$—C-5), 131.1 (br s, β-C$_{Pyrrole}$), 137.4 (Ar$_F$—C$_{para}$), 141.3 (d, $^1J_{C-F}$=246.2 Hz, Ar$_F$—C$_{meta}$), 142.8 (Ar$_2$—C$_{ipso}$), 143.0 (Ar$_1$—C$_{ipso}$), 146.9 (d, $^1J_{C-F}$=241.0 Hz, Ar$_F$—C$_{ortho}$), 155.9 (Ar$_1$C-3), 156.0 (Ar$_2$—C-3) ppm.

$^{19}$F-NMR (376 MHz, acetone-d$_6$): δ=−120.86--−121.09 (m, 2F, CF$_2$), −122.49--−122.82 (m, 2F, CF$_2$), −123.33--−123.51 (m, 2F, CF$_2$), −123.65--−123.92 (m, 2F, CF$_2$), 129.90--−130.15 (m, 2F, CF$_2$), −138.92 (d, $^2J_{H-F}$=50.6 Hz, 2F, CF$_2$H), −140.77--−141.01 (m, 2F, Ar—F$_{ortho}$), −158.35 (d, J=23.4 Hz, 2F, Ar—F$_{meta}$) ppm.

HRMS (ESI-TOF): m/z calc. for C$_{51}$H$_{29}$F$_{16}$N$_4$O$_4$ [M+H]$^+$: 1065.1933; found: 1065.1949

UV-VIS (acetone), λ$_{max}$ [log ε(L·mol$^{-1}$·cm$^{-1}$)]: 414.5 (5.30), 511 (4.36), 544 (4.04), 587 (4.02), 643 (3.85) nm.

Example 5

Preparation of meso-5-[2,3,5,6-tetrafluoro-4-(2,3-dihydroxy-propyloxy)]-substituted BODIPY 5.1 Preparation of 5-[2,3,5,6-tetrafluoro-4-(2,3-dihydroxy-propyloxy)]-4,4-difluoro-4-bora-3a,4a-diaza-s-indacene In a typical experiment, 5-[2,3,5,6-tetrafluoro-4-(2,2-dimethyl-1,3-dioxolan-4-yl-methoxy)]-dipyrromethane (2.0 g, 4.7 mmol) was dissolved in DCM (70 ml), DDQ (1.06 g, 4.7 mmol) was added and the reaction mixture stirred for 5 min. at room temperature. Then, DIPEA (6.07 ml, 35 mmol) was added and after 3 minutes BF$_3$—OEt$_2$ (6.79 ml, 55 mmol) was added to the reaction mixture and stirred further for 20 min. at room temperature. DCM was evaporated, ethyl acetate added and the organic phase washed three times with water. Drying over sodium sulfate and purification via column chromatography (DCM/ethyl acetate=1:11) yielded the BODIPY as an orange-green solid (640 mg, 1.4 mmol, 31%).

5-[2,3,5,6-tetrafluoro-4-(2,3-dihydroxy-propyloxy)]-4,4-difluoro-4-bora-3a,4a-diaza-s-indacene

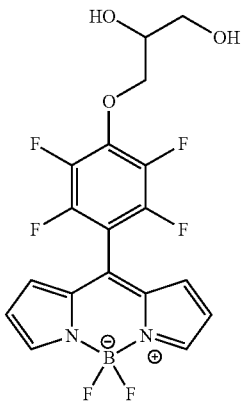 [SMILES: OCC(O)COc1c(F)c(F)c(C2=C3C=CC=[N+]3[B-](F)(F)n3cccc32)c(F)c1F]

$^1$H-NMR (700 MHz, acetone-d$_6$): δ=3.11 (br s, 2H, OH), 3.71 (dd, J=5.5, 2.7 Hz, 2H, OCH$_2$), 4.05-4.09 (m, 1H, OCH$_2$CH), 4.43 (ddt, J=10.3, 6.2, 1.1 Hz, 1H, Ar$_F$—OCH$_2$), 4.54 (ddt, J=10.3, 4.2, 1.0 Hz, 1H, Ar$_F$—OCH$_2$), 6.71 (d, J=4.3 Hz, 2H, 3,7-H$_{Pyrrole}$), 7.23 (d, J=4.2 Hz, 2H, 2,8-H$_{Pyrrole}$), 8.12 (s, 2H, 1,9-H$_{Pyrrole}$) ppm.

$^{13}$C-NMR (126 MHz, acetone-d$_6$): δ=62.6 (OCH$_2$), 70.9 (OCH$_2$CH), 76.5 (Ar$_F$—OCH$_2$), 105.4 (t, J=18.6 Hz, Ar$_F$—C$_{meso}$), 113.3 (Ar$_F$—C$_{ipso}$), 119.8 (3,7-C$_{Pyrrole}$), 130.8 (4,6-C$_{Pyrrole}$), 131.3 (2,8-C$_{Pyrrole}$), 135.1 (5-C$_{meso}$), 139.9 (Ar$_F$—C$_{para}$), 141.3 (Ar$_F$—C$_{meta}$), 144.7 (Ar$_F$—C$_{ortho}$), 146.6 (1,9-C$_{Pyrrol}$) ppm.

$^{19}$F-NMR (376 MHz, acetone-d$_6$): δ=−142.29--−142.46 (m, 2F, Ar—F$_{ortho}$), −144.52 (dd, J=56.7, 28.0 Hz, BF$_2$) −158.35 (m, 2F, Ar—F$_{meta}$) ppm.

HRMS (ESI-TOF): m/z calc. for C$_{18}$H$_{14}$BF$_6$N$_2$O$_3$ [M+H]$^+$: 431.0996; found: 431.0989

UV-VIS (acetone), λ$_{max}$ [log ε(L·mol$^{-1}$·cm$^{-1}$)]: 517 (4.46) nm.

Example 6

Preparation of 5,10,15-Tris(2,3,5,6-tetrafluoro-4-(2-Propin-1-oxy)phenyl)-corrole 6.1 Preparation of 5,10,15-Tris(2,3,5,6-tetrafluoro-4-(2-propin-1-oxy)phenyl)-corrole In a typical experiment, tris(pentafluorophenyl)-corrole (30 mg, 37.66 μmol) was dissolved in 5 mL THF under argon atmosphere, propargyl alcohol (0.3 mL, 0.52 mmol) and KOH (170 mg, 0.89 mmol) were added and the reaction mixture stirred for 24 hours at room temperature. After aqueous workup, extraction with DCM and drying over Na$_2$SO$_4$, the crude product was purified by column chromatography (DCM/n-hexane=1:1) to obtain a black-purple solid (26 mg, 76%).

5,10,15-Tris(2,3,5,6-tetrafluoro-4-(2-Propin-1-oxy)phenyl)-corrole

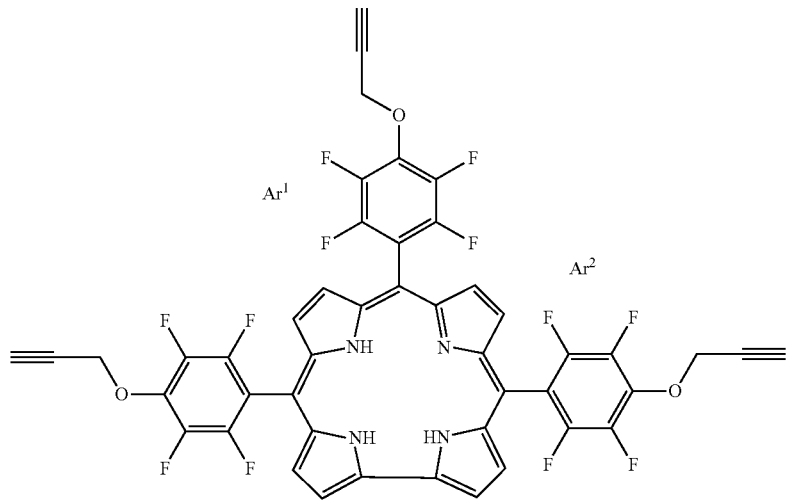 [SMILES: C#CCOc1c(F)c(F)c(-c2c3nc(c(-c4c(F)c(F)c(OCC#C)c(F)c4F)c4ccc([nH]4)c4ccc([nH]4)c(-c4c(F)c(F)c(OCC#C)c(F)c4F)c4ccc2[nH]4)C=C3)c(F)c1F]

$^1$H-NMR (500 MHz, CDCl$_3$): δ=2.78 (t, J=2.4 Hz, 3H), 5.17 (d, J=2.3 Hz, 6H), 8.58 (br s, 2H, β-H$_{Pyrrol}$), 8.61 (d, J=4.6 Hz, 2H, β-H$_{Pyrrol}$), 8.80 (d, J=4.6 Hz, 2H, β-H$_{Pyrrol}$), 9.07 (d, J=4.2 Hz, 2H, β- H$_{Pyrrol}$) ppm.

$^{13}$C-NMR (126 MHz, CDCl$_3$): δ=62.0 (t, C—1), 77.2 (d, C-3), 77.6 (s, Ar$^1$—C-2), 77.7 (s, Ar$_2$—C-2), 95.0 (s, C$_{meso}$), 113.3 (t, $^2$J$_{C-F}$=18.4 Hz, Ar$^2$$_F$—C$_{ipso}$), 115.5 (t, $^2$J$_{C-F}$=19.6 Hz, Ar$^1$$_F$—C$_{ipso}$), 116.9 (s, β-C), 126.2 (s, β-C), 127.6 (s, β-C), 130.4 (s, β-C, 134.7 (s, β-C), 136.5 (m$_c$, Ar$_F$—C$_{para}$), 141.6 (dd, $^{1,2}$J$_{C-F}$=250.0, 15.5 Hz, Ar$^1$$_F$—C$_{meta}$), 141.8 (dd, $^{1,2}$J$_{C-F}$=249.4, 15.9 Hz, Ar$^2$$_F$—C$_{meta}$), 146.2 (d, $^1$J$_{C-F}$=248.1 Hz, Ar$^2$$_F$—C$_{ortho}$), 146.7 (d, $^1$J$_{C-F}$=247.7 Hz, Ar$^1$$_F$—C$_{ortho}$) ppm.

$^{19}$F-NMR (376 MHz, CDCl$_3$): δ=−138.76 (dd, J=22.9, 7.2 Hz, 2F, Ar$^1$—F$_{ortho}$), −139.29 (d, J=16.8 Hz, 4F, Ar$^2$—F$_{ortho}$), −155.44 (d, J=16.5 Hz, 4F, Ar$^2$—F$_{meta}$), −155.86 (dd, J=23.2, 7.6 Hz, 2F, Ar$^1$—F$_{meta}$) ppm.

HRMS (ESI-TOF): m/z calc. for C$_{46}$H$_{21}$F$_{12}$N$_4$O$_3$ [M+H]$^+$: 905.1417; found: 905.1434

UV-VIS (DCM), λ$_{max}$ [log ε(L·mol$^{-1}$·cm$^{-1}$)]: 410.5 (5.17), 564 (4.47), 605 (4.18) nm.

Example 7

Cell Tests of Selected Compounds in the HT 29 and Other Cell Lines

The photosensitizing activity was determined in the following cell lines:
HT29 (human colon adenocarcinoma cell line)
L929 (mouse fibroblast cell line)
A431 (human epidermoid carcinoma cell line)
A253 (submaxillary salivary gland, epidermoid cell line)
CAL-27 (human tongue squamous cell carcinoma cell line).

The cell lines were grown in DMEM (PAA Laboratories GmbH) supplemented with 10% heat-inactivated fetal calf serum (FCS, PAA Laboratories GmbH), 1% penicillin (10000 IU) and streptomycin (10000 µg/ml, PAA Laboratories GmbH). Cells were kept as a monolayer culture in a humidified incubator (5% CO$_2$ in air at 37° C.).

A photosensitizer stock solution (2 mM) was performed in DMSO and was kept in the dark at 4° C. Further dilution was performed in DMEM medium without phenol red supplemented with 10% FCS to reach a final photosensitizer concentration of 2 or 10 µM, respectively. 2·10$^4$ cells/ml were seeded in micro plates (2·10$^5$ cells/well). Cells were incubated with fresh medium (DMEM without phenol red) containing 10% FCS with 2 or 10 µM of the photosensitizer for 24 h before light exposure. Before photosensitization, cells were washed, cell culture medium was exchanged with DMEM without phenol red and 10% FCS, then irradiated at room temperature with a 652 nm diode laser (Ceralas PDT 652, biolitec AG) at a fixed fluence rate of 100 mW/cm$^2$ (50 J/cm$^2$). Following irradiation, cells were incubated in a humidified incubator (5% CO$_2$ in air at 37° C.) for 24 h until cell viability assay.

The cell viability was assessed by the XTT assay. 500 mg XTT (sodium 3'-[phenylaminocarbonyl)-3,4-tetrazolium]-bis(4-methoxy-6-nitro)benzene sulfonic acid, Applichem GmbH) is dissolved in 500 ml PBS-Buffer (without Ca$^{2+}$ and Mg$^2$) and sterile filtered. Solution was stored in the dark at −20° C. until use. A sterile solution containing PMS (N-methyl dibenzopyrazine methyl sulfate, Applichem GmbH) was needed as an activation reagent for the XTT. 0.383 mg PMS was dissolved in 1 ml PBS-Buffer The solution should be stored frozen and should not be exposed to light. The XTT reagent solution was thawed in a 37° C. water bath and the activation solution (PMS) was added immediately prior to use. To prepare a reaction solution sufficient for one micro plate (96 wells), 0.1 ml activation solution (PMS) was given to 5 ml XTT reagent. The medium in the micro plate was exchanged with RPMI without phenol red and 10% FCS (100 µl) prior adding 50 µl XTT reaction solution per well. The micro plate was incubated for 2-3 hours at 37° C. and 5% CO$_2$ until an orange dye is to be formed. The micro plate has been shaken gently to evenly distribute the dye in the wells.

The absorbance of the samples was measured with a spectrophotometer (Infinite 200, Tecan Group Ltd.) at a wavelength of 490 nm. In order to measure reference absorbance (to measure non-specific readings) a wavelength of 630-690 nm was used.

The examples 7.1 to 7.10 illustrate the photodynamic activity ("DT" means dark toxicity and "Laser" means photo toxicity) of photosensitizers having a substitution pattern as referred to in the present invention. Specifically the photosensitizers exhibit a strong photodynamic activity even in the HT29 cell line, which is known to be very resistant against cell-toxic agents and PDT as well.

The examples 7.11 to 7.17 are included to illustrate, that photosensitizers which do not have a substitution pattern as referred to in the present invention do not exhibit a promising photodynamic activity in the cell experiments. Some of these photosensitizers show PDT activity against more sensitive cell lines, e.g. in example 7.13 against CAL-27 cells but they lack activity against the HT29 cell line.

7.1 Cell Test of 5,10,15,20-tetrakis-[2,3,5,6-tetra-fluoro-4-(2,3-dihydroxypropyloxy)-phenyl]-porphyrin 7.2 Cell Test 5,10,15-tris(3-hydroxy-phenyl)-20-[2,3,5,6-tetra-fluor-4-(2,3-dihydroxy-propyloxy)-phenyl]-porphyrin

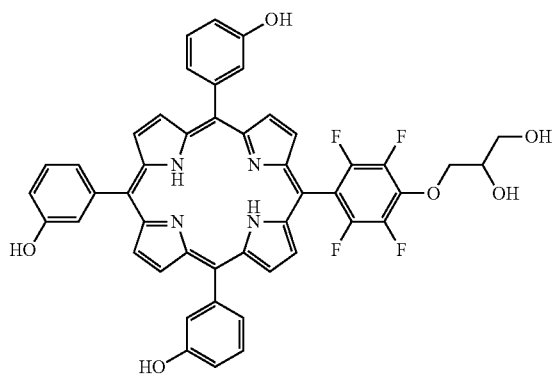

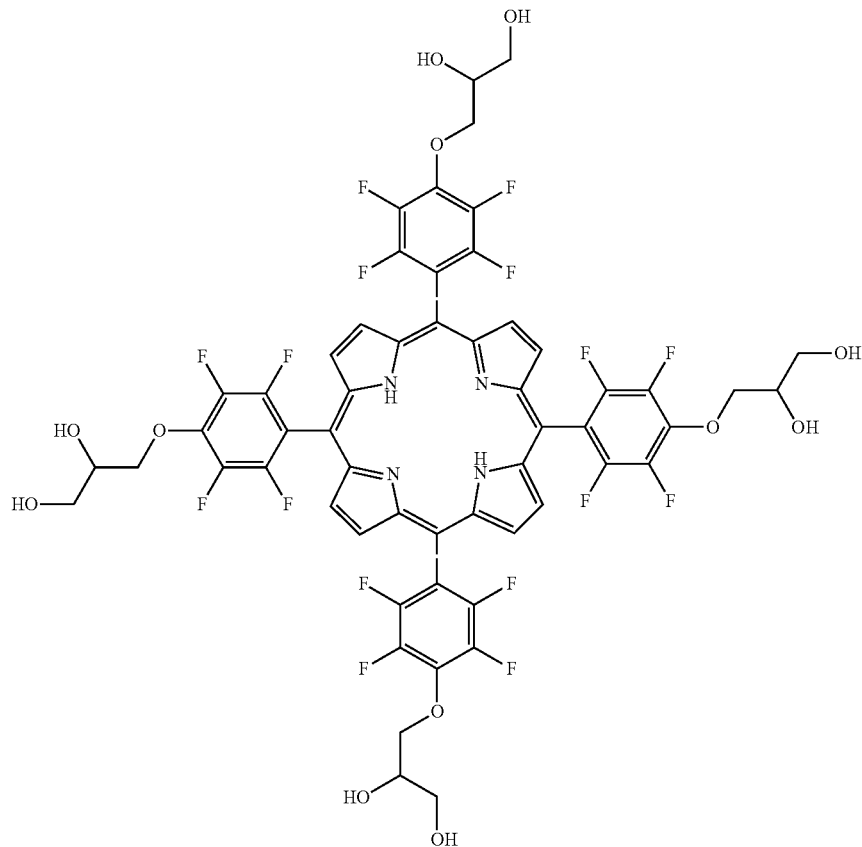 [SMILES: OCC(O)COc1c(F)c(F)c(-c2c3nc(c(-c4c(F)c(F)c(OCC(O)CO)c(F)c4F)c4ccc([nH]4)c(-c4c(F)c(F)c(OCC(O)CO)c(F)c4F)c4nc(c(-c5c(F)c(F)c(OCC(O)CO)c(F)c5F)c5ccc2[nH]5)C=C4)C=C3)c(F)c1F]

Figure 4:
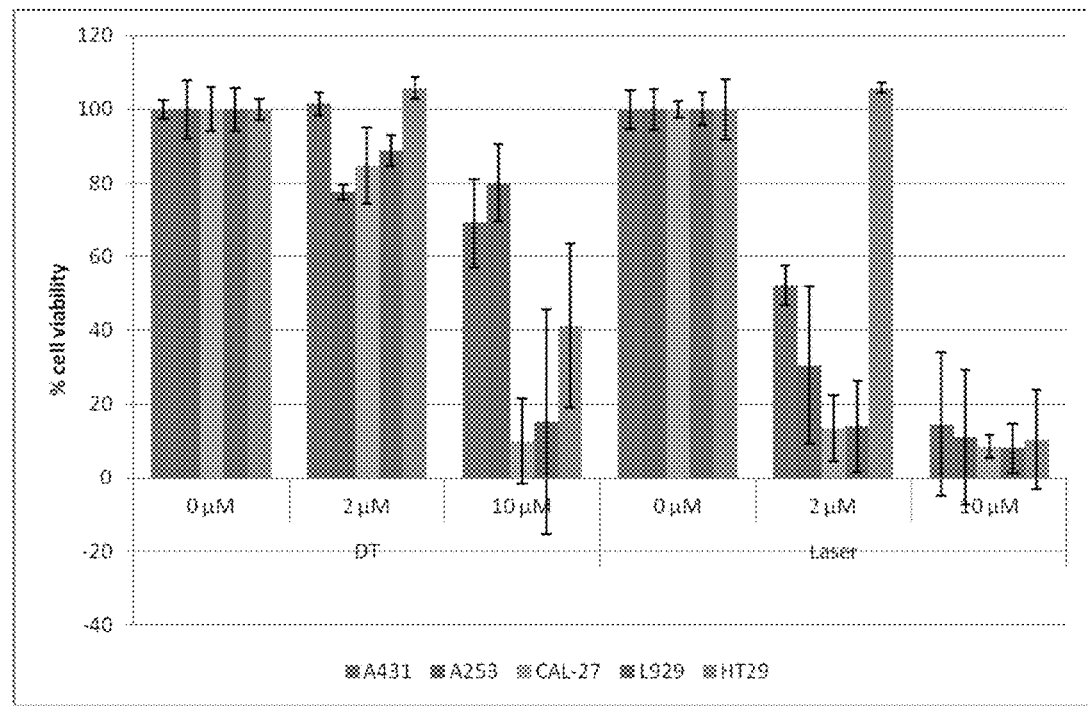
FIG. 4 shows the results of cell tests of 5,10,15,20-tetrakis-[2,3,5,6-tetrafluoro-4-(2,3-dihydroxypropyloxy)-phenyl]-porphyrin

The results of this cell test, with 24 h incubation time, irradiation with a 652 nm laser, and 50 J/cm$^2$, are shown in FIG. 4.

Figure 5:
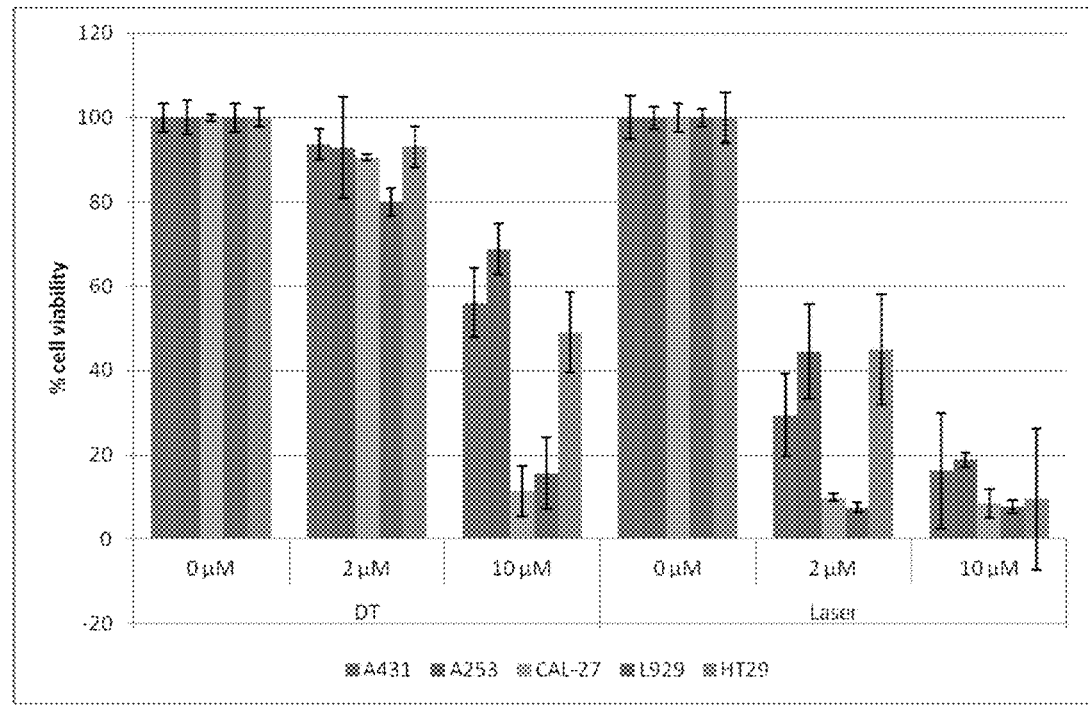
FIG. 5 shows the results of cell tests of 5,10,15-tris(3-hydroxy-phenyl)-20-[2,3,5,6-tetra-fluor-4-(2,3-dihydroxy-propyloxy)¬phenyl]-porphyrin

The results of this cell test, with 24 h incubation time, irradiation with a 652 nm laser, and 50 J/cm$^2$, are shown in FIG. 5.

7.3 Cell Test of 2,3-dihydroxy-5,10,15,20-tetrakis-[2,3,5,6-tetrafluoro-4-(2,3-dihydroxypropyloxy)-phenyl]-porphyrin

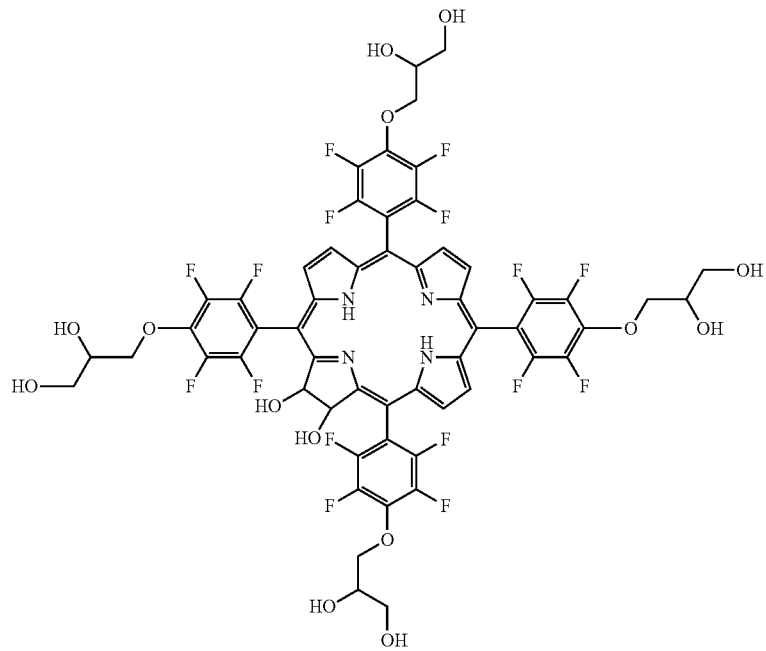 [SMILES: OCC(O)COc1c(F)c(F)c(-c2c3nc(c(-c4c(F)c(F)c(OCC(O)CO)c(F)c4F)c4ccc([nH]4)c(-c4c(F)c(F)c(OCC(O)CO)c(F)c4F)c4nc(c(-c5c(F)c(F)c(OCC(O)CO)c(F)c5F)c5ccc2[nH]5)C(O)C4O)C=C3)c(F)c1F]

Figure 6:
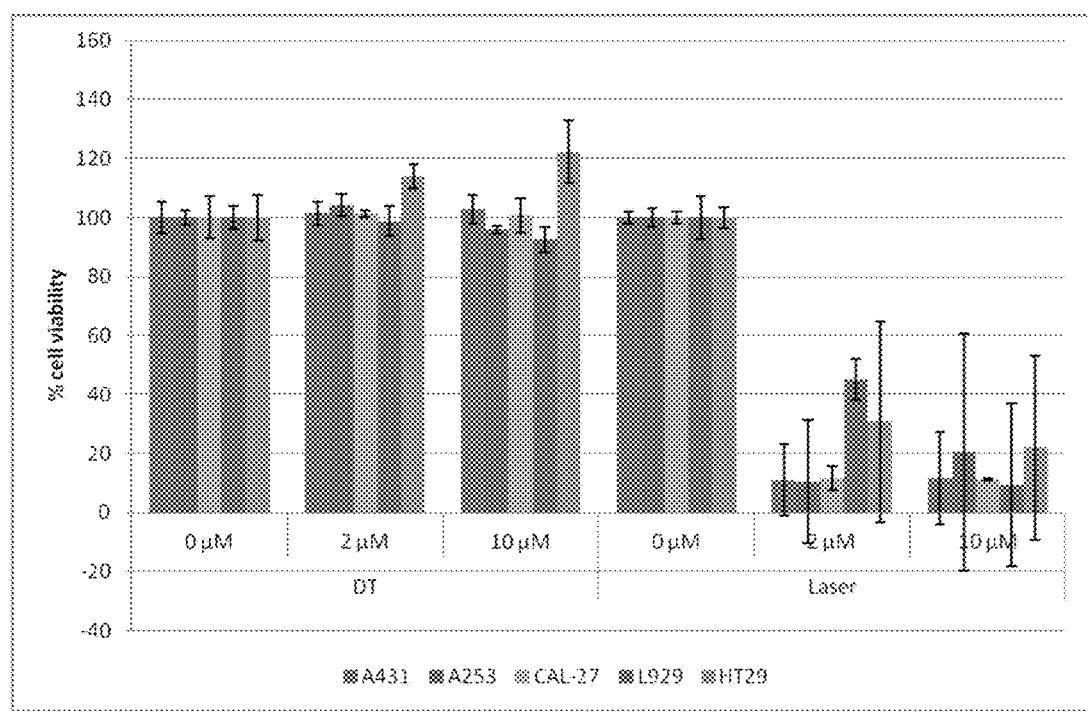
FIG. 6 shows the results of cell tests of 2,3-dihydroxy-5,10,15,20-tetrakis-[2,3,5,6-tetrafluoro-4-(2,3-dihydroxypropyloxy)-phenyl]-porphyrin

The results of this cell test, with 24 h incubation time, irradiation with a 652 nm laser, and 50 J/cm², are shown in FIG. 6.

7.4 Cell Test 5,15-bis-(3-hydroxyphenyl)-10,20-bis-[2,3,5,6-tetrafluoro-4-(2,3-dihydroxypropyloxy)-phenyl]-porphyrin

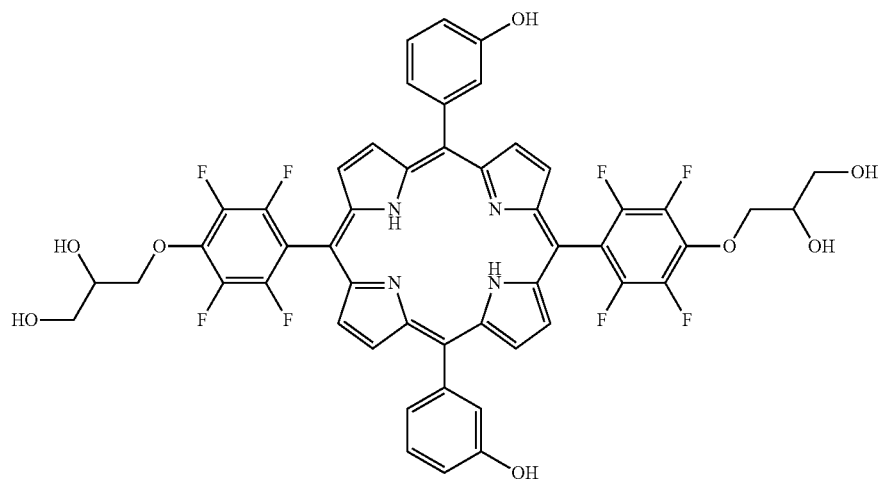 [SMILES: OCC(O)COc1c(F)c(F)c(-c2c3nc(c(-c4cccc(O)c4)c4ccc([nH]4)c(-c4c(F)c(F)c(OCC(O)CO)c(F)c4F)c4nc(c(-c5cccc(O)c5)c5ccc2[nH]5)C=C4)C=C3)c(F)c1F]

Figure 7:
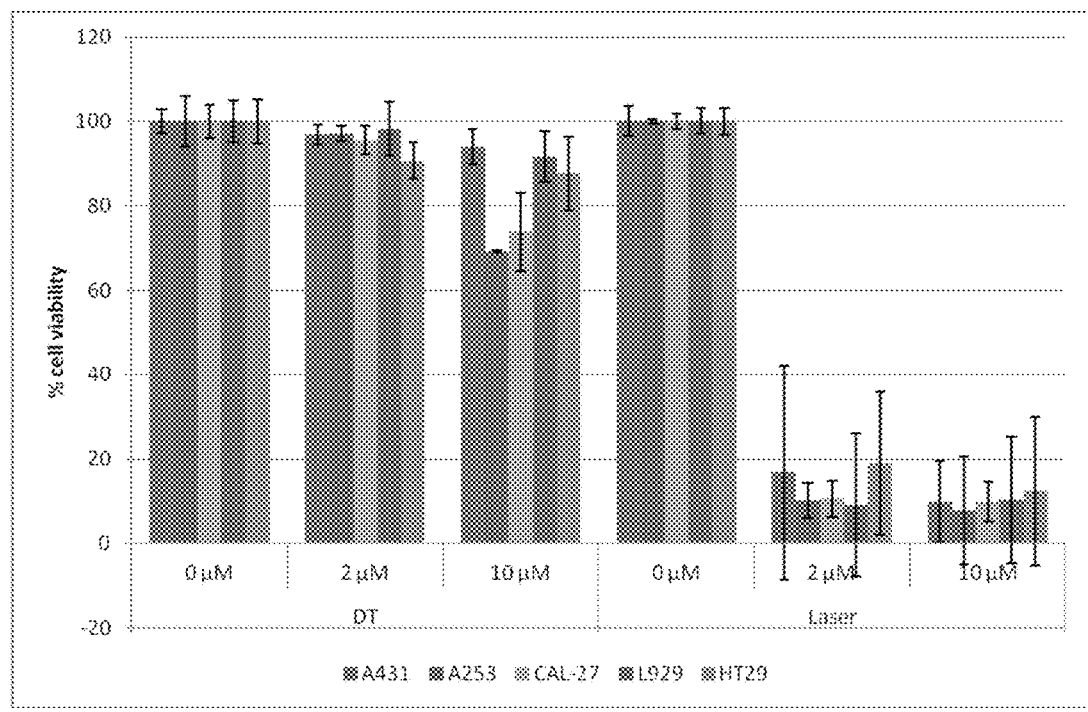
FIG. 7 shows the results of cell tests of 5,15-bis-(3-hydroxyphenyl)-10,20-bis-[2,3,5,6-tetrafluoro-4-(2,3-dihydroxypropyloxy)-phenyl]-porphyrin

The results of this cell test, with 24 h incubation time, irradiation with a 652 nm laser, and 50 J/cm², are shown in FIG. 7.

7.5 Cell Test of 2,3-dihydroxy-5,15-bis-(3-hydroxyphenyl)-10,20-bis-[2,3,5,6-tetrafluoro-4-(2,3-dihydroxypropyloxy)-phenyl]-porphyrin

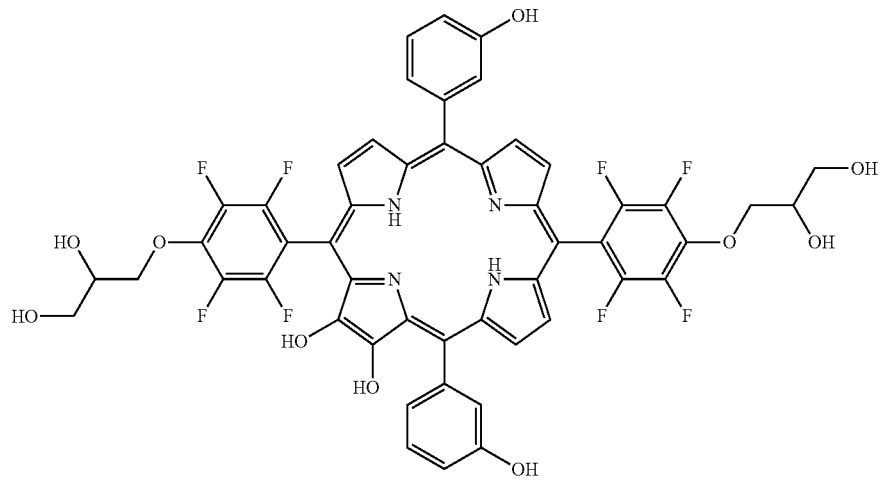 [SMILES: OCC(O)COc1c(F)c(F)c(-c2c3nc(c(-c4cccc(O)c4)c4ccc([nH]4)c(-c4c(F)c(F)c(OCC(O)CO)c(F)c4F)c4nc(c(-c5cccc(O)c5)c5ccc2[nH]5)C(O)=C4O)C=C3)c(F)c1F]

Figure 8:
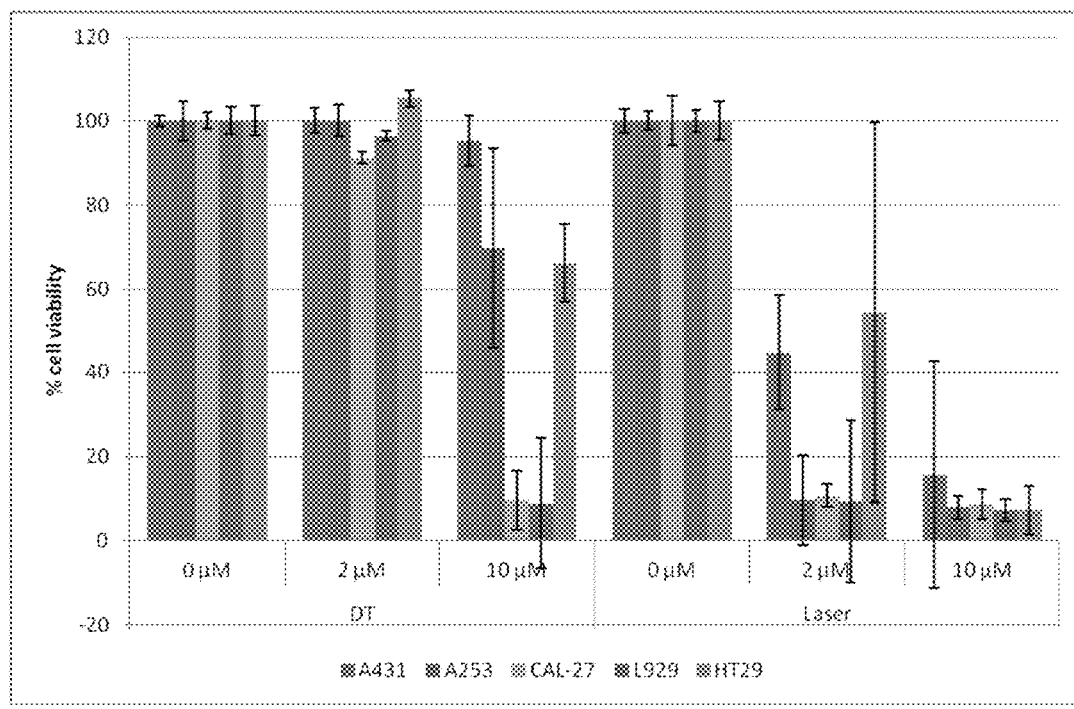
FIG. 8 shows the results of cell tests of 2,3-dihydroxy-5,15-bis-(3-hydroxyphenyl)-10,20-bis-[2,3,5,6-tetrafluoro-4-(2,3-dihydroxypropyloxy)-phenyl]-porphyrin

The results of this cell test, with 24 h incubation time, irradiation with a 652 nm laser, and 50 J/cm², are shown in FIG. 8.

7.6 Cell Test of 17,18-dihydroxy-5,10,15-tris(3-hydroxyphenyl)-20-[2,3,5,6-tetrafluoro-4-(2,3-dihydroxy-propyloxy)-phenyl]-porphyrin

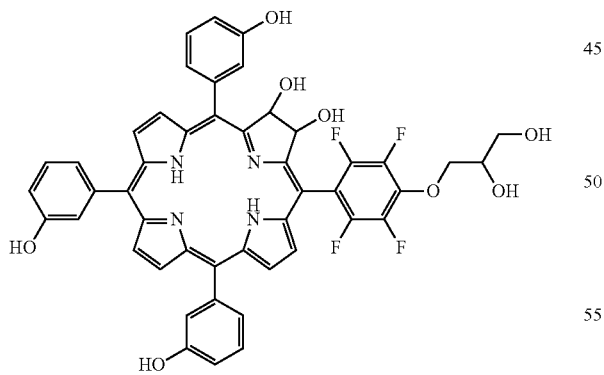

Figure 9:
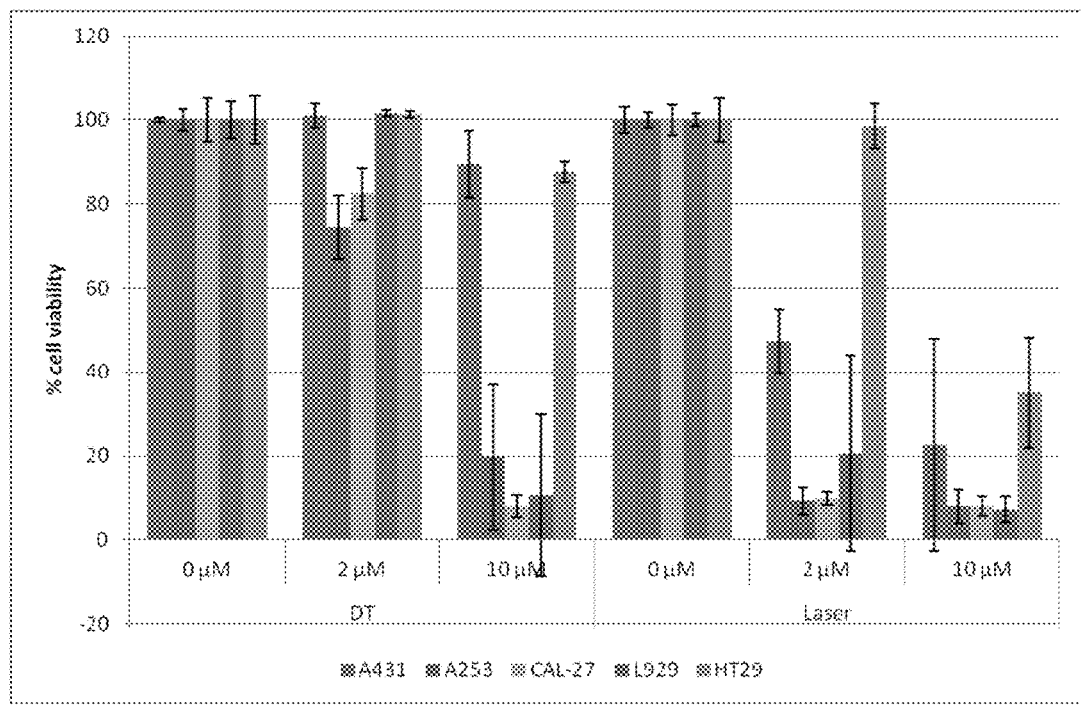
FIG. 9 shows the results of cell tests of 17,18-dihydroxy-5,10,15-tris(3-hydroxyphenyl)-20-[2,3,5,6-tetrafluoro-4-(2,3-dihydroxy-propyloxy)-phenyl]-porphyrin

The results of this cell test, with 24 h incubation time, irradiation with a 652 nm laser, and 50 J/cm², are shown in FIG. 9.

7.7 Cell Test of 5,10,15,20-tetrakis-[2,3,5,6-tetra-fluoro-4-(1,3-dihydroxyprop-2-ylamino)-phenyl]-porphyrin

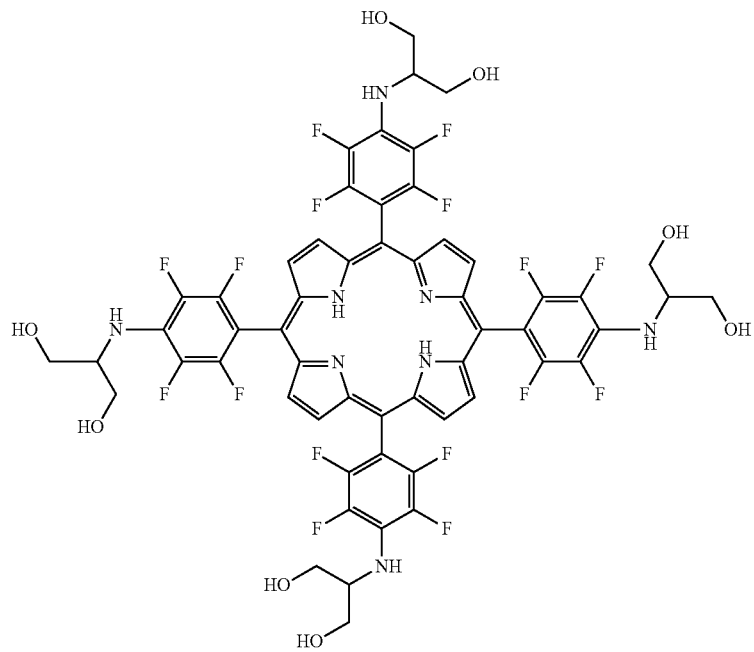 [SMILES: OCC(CO)Nc1c(F)c(F)c(-c2c3nc(c(-c4c(F)c(F)c(NC(CO)CO)c(F)c4F)c4ccc([nH]4)c(-c4c(F)c(F)c(NC(CO)CO)c(F)c4F)c4nc(c(-c5c(F)c(F)c(NC(CO)CO)c(F)c5F)c5ccc2[nH]5)C=C4)C=C3)c(F)c1F]

Figure 10:
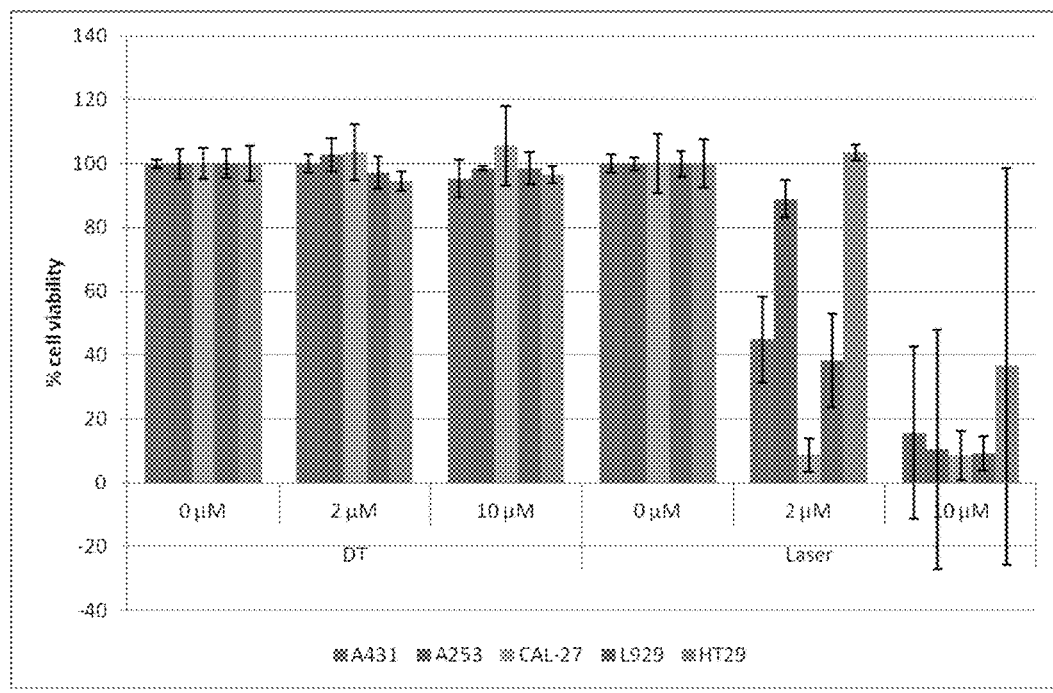
FIG. 10 shows the results of cell tests of 5,10,15,20-tetrakis-[2,3,5,6-tetrafluoro-4-(1,3-dihydroxyprop-2-ylamino)-phenyl]-porphyrin

The results of this cell test, with 24 h incubation time, irradiation with a 652 nm laser, and 50 J/cm², are shown in FIG. 10.

7.8 Cell Test of 2,3-dihydro-5,10,15,20-tetrakis-[2,3,5,6-tetrafluoro-4-(2,3-dihydroxypropyloxy)-phenyl]-chlorin

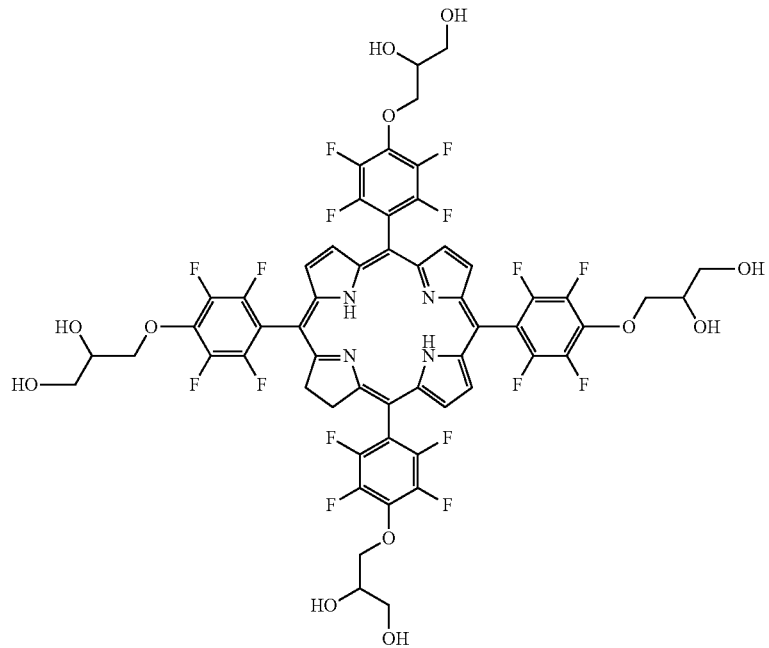 [SMILES: OCC(O)COc1c(F)c(F)c(-c2c3nc(c(-c4c(F)c(F)c(OCC(O)CO)c(F)c4F)c4ccc([nH]4)c(-c4c(F)c(F)c(OCC(O)CO)c(F)c4F)c4nc(c(-c5c(F)c(F)c(OCC(O)CO)c(F)c5F)c5ccc2[nH]5)CC4)C=C3)c(F)c1F]

Figure 11:
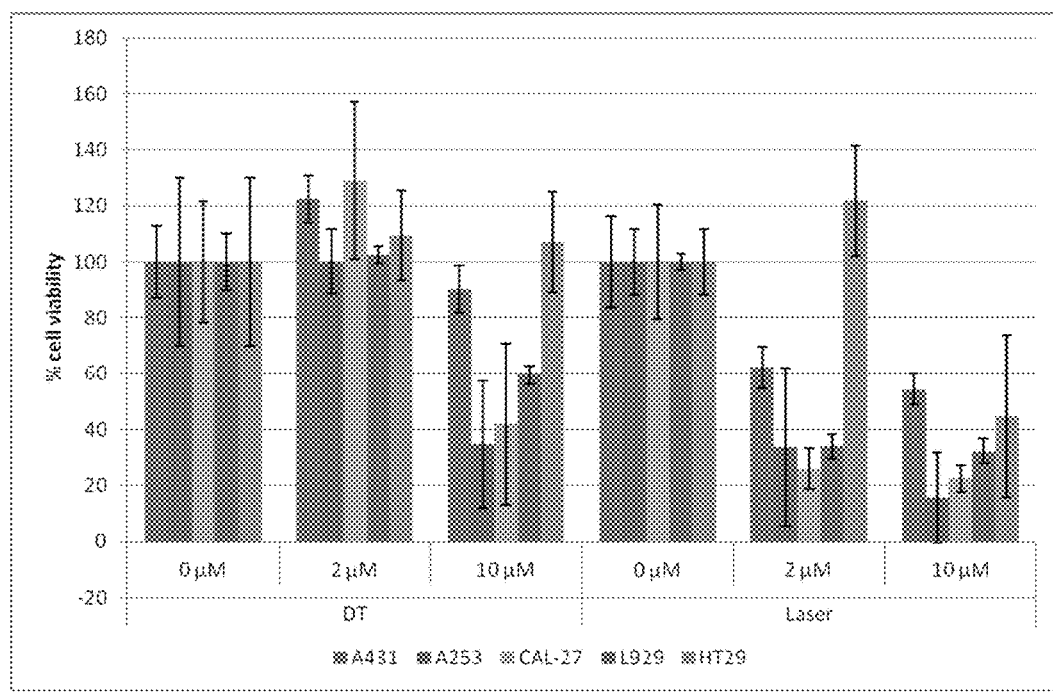
FIG. 11 shows the results of cell tests of 2,3-dihydro-5,10,15,20-tetrakis-[2,3,5,6-tetrafluoro-4-(2,3-dihydroxypropyloxy)-phenyl]-chlorin

The results of this cell test, with 24 h incubation time, irradiation with a 652 nm laser, and 50 J/cm², are shown in FIG. 11.

7.9 Cell Test of 2,3-dihydro-5,10,15-tris(3-hydroxyphenyl)-20-[2,3,5,6-tetrafluoro-4-(2,3-dihydroxypropyloxy)-phenyl]-chlorin (and isomer)

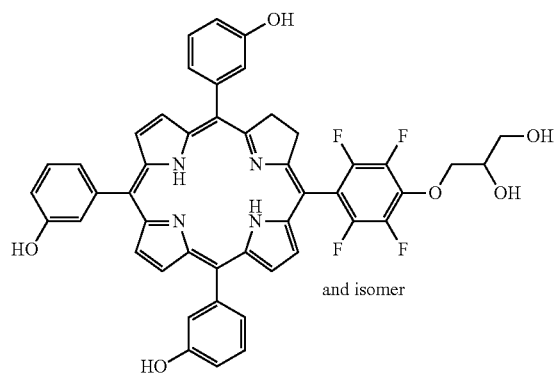 [SMILES: OCC(O)COc1c(F)c(F)c(-c2c3nc(c(-c4cccc(O)c4)c4ccc([nH]4)c(-c4cccc(O)c4)c4nc(c(-c5cccc(O)c5)c5ccc2[nH]5)C=C4)CC3)c(F)c1F]

and isomer

Figure 12:
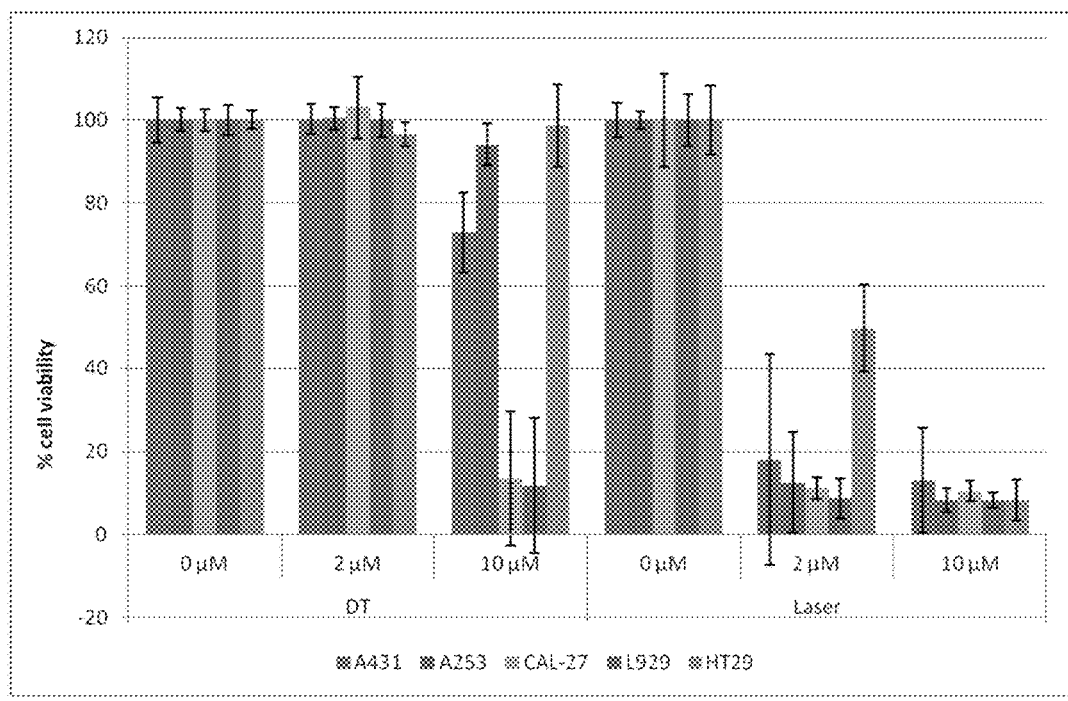
FIG. 12 shows the results of cell tests of 2,3-dihydro-5,10,15-tris(3-hydroxyphenyl)-20-[2,3,5,6-tetrafluoro-4-(2,3-dihydroxy-propyloxy)-phenyl]-chlorin (and isomer)

The results of this cell test, with 24 h incubation time, irradiation with a 652 nm laser, and 50 J/cm², are shown in FIG. 12.

Figure 13:
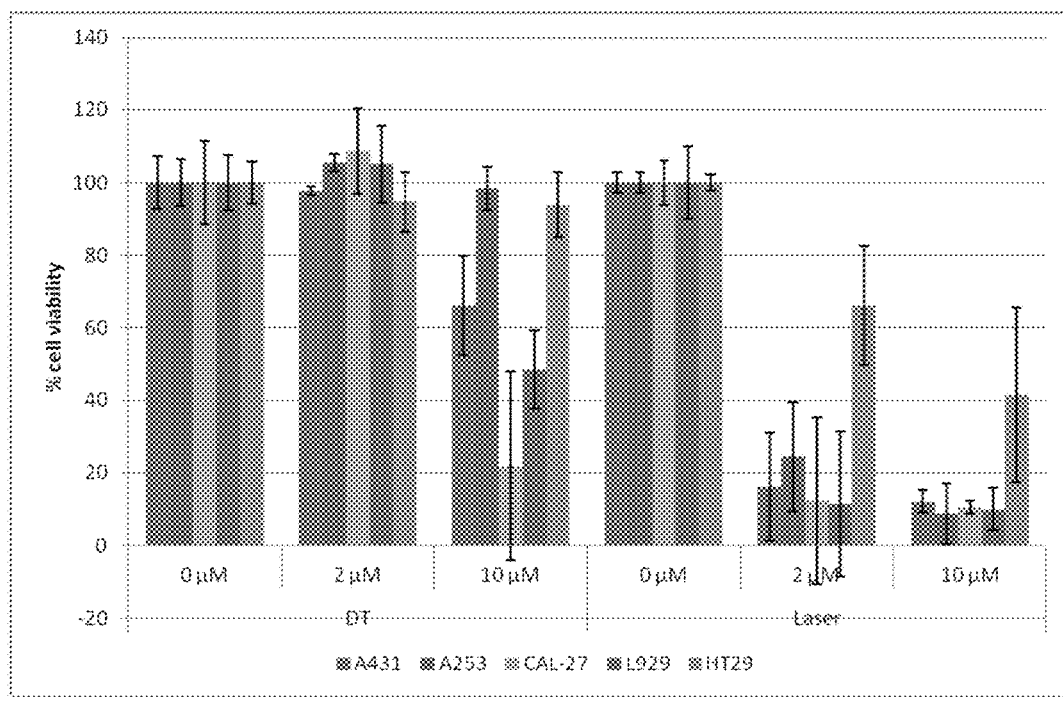
FIG. 13 shows the results of cell tests of 2,3-dihydro-5,15-bis-(3-hydroxyphenyl)-10,20-bis-[2,3,5,6-tetrafluoro-4-(2,3-dihydroxypropyloxy)-phenyl]-chlorin

7.10 Cell Test of 2,3-dihydro-5,15-bis-(3-hydroxyphenyl)-10,20-bis-[2,3,5,6-tetrafluoro-4-(2,3-dihydroxypropyloxy)-phenyl]-chlorin The results of this cell test, with 24 h incubation time, irradiation with a 652 nm laser, and 50 J/cm², are shown in FIG. 13.

7.11 Cell Test of 5,10,15,20-tetrakis-[4-(4-hydroxybutyloxy)-2,3,5,6-tetrafluorophenyl]-porphyrin

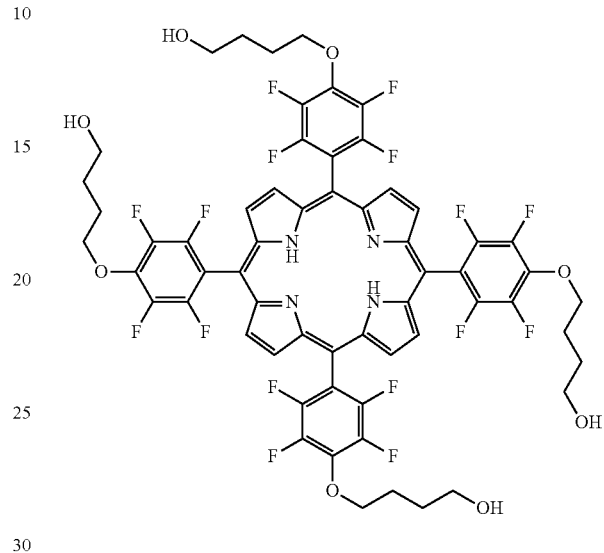

Figure 14:
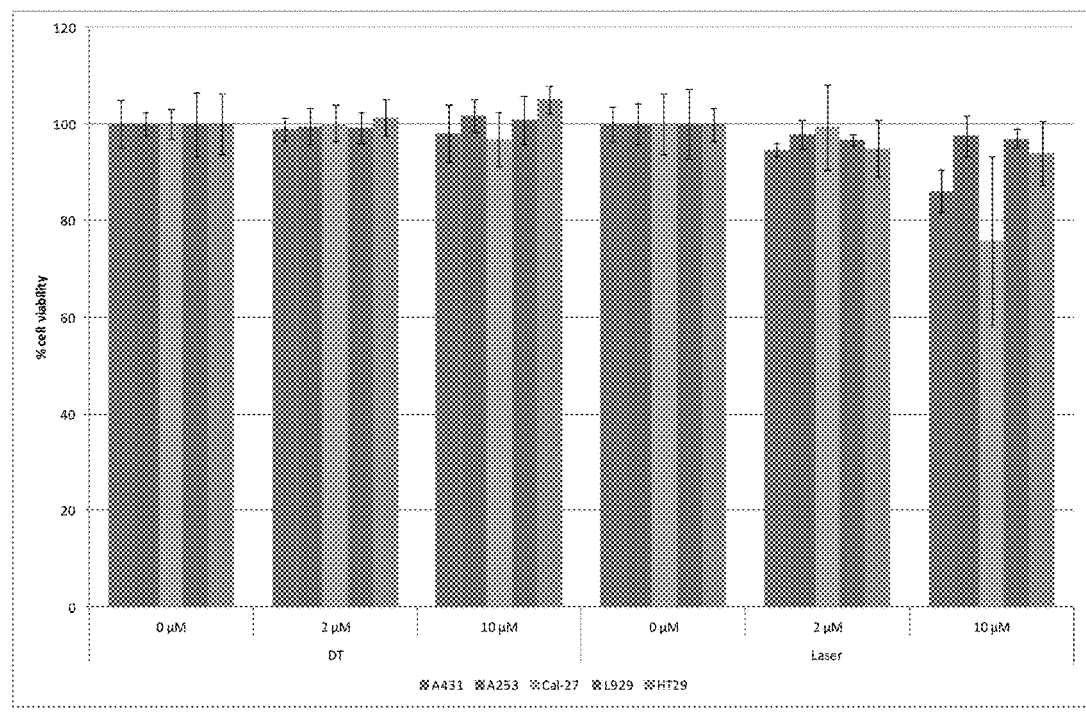
FIG. 14 shows the results of cell tests of 5,10,15,20-tetrakis-[4-(4-hydroxybutyloxy)-2,3,5,6-tetrafluorophenyl]-porphyrin

The results of this cell test, with 24 h incubation time, irradiation with a 652 nm laser, and 50 J/cm², are shown in FIG. 14.

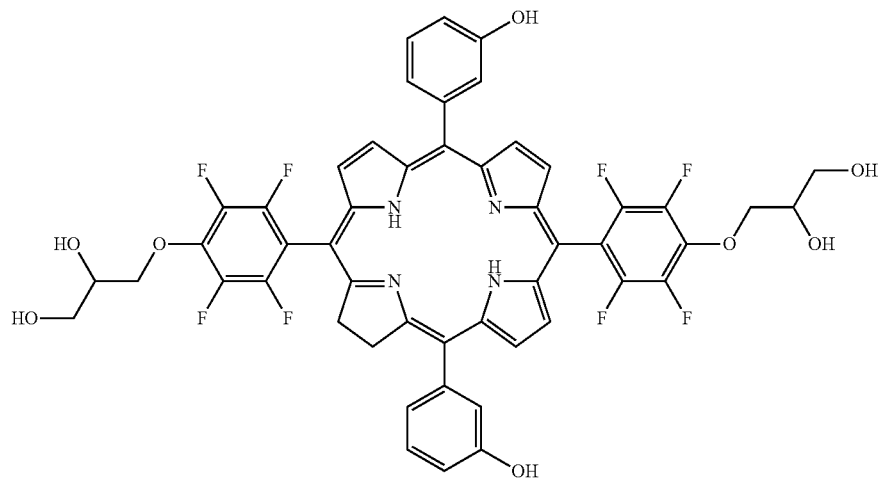 [SMILES: OCC(O)COc1c(F)c(F)c(-c2c3nc(c(-c4cccc(O)c4)c4ccc([nH]4)c(-c4c(F)c(F)c(OCC(O)CO)c(F)c4F)c4nc(c(-c5cccc(O)c5)c5ccc2[nH]5)CC4)C=C3)c(F)c1F]

7.12 Cell Test of 5,10,15-tris-(3-hydroxyphenyl)-20-penta-fluorophenyl-porphyrin

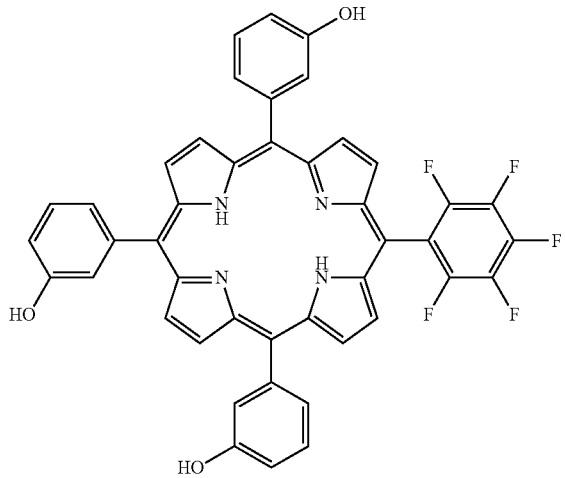 [SMILES: Oc1cccc(-c2c3nc(c(-c4cccc(O)c4)c4ccc([nH]4)c(-c4c(F)c(F)c(F)c(F)c4F)c4nc(c(-c5cccc(O)c5)c5ccc2[nH]5)C=C4)C=C3)c1]

Figure 15:
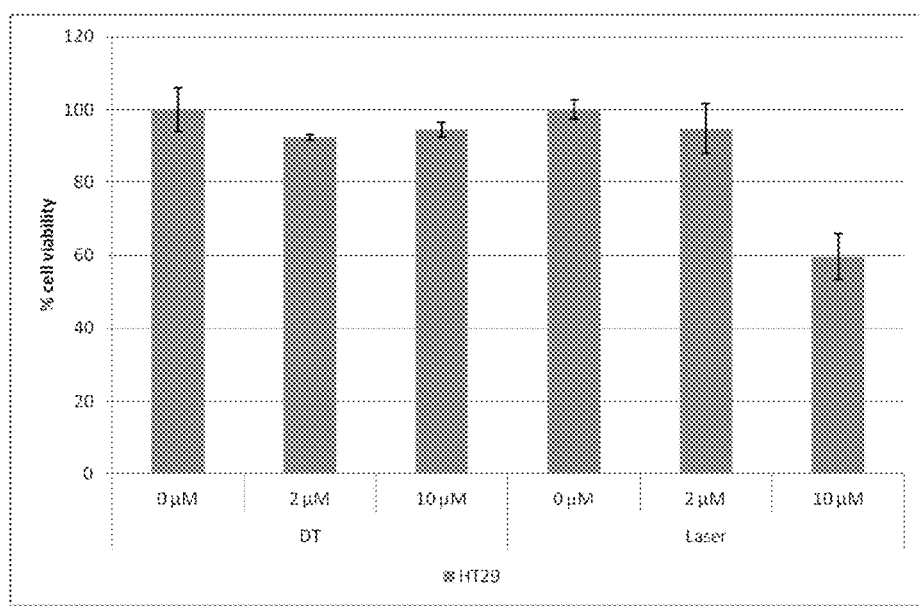
FIG. 15 shows the results of cell tests of 5,10,15-tris-(3-hydroxyphenyl)-20-penta-fluorophenyl-porphyrin

The results of this cell test, with 24 h incubation time, irradiation with a 652 nm laser, and 50 J/cm², are shown in FIG. 15.

7.13 Cell Test of 5,10,15-tris-(3-hydroxy-phenyl)-20-[4-(butyloxy)-tetra-fluor-phenyl]-porphyrin

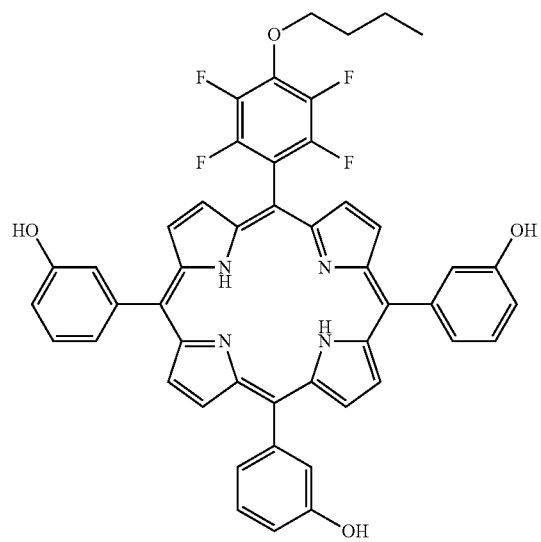 [SMILES: CCCCOc1c(F)c(F)c(-c2c3nc(c(-c4cccc(O)c4)c4ccc([nH]4)c(-c4cccc(O)c4)c4nc(c(-c5cccc(O)c5)c5ccc2[nH]5)C=C4)C=C3)c(F)c1F]

Figure 16:
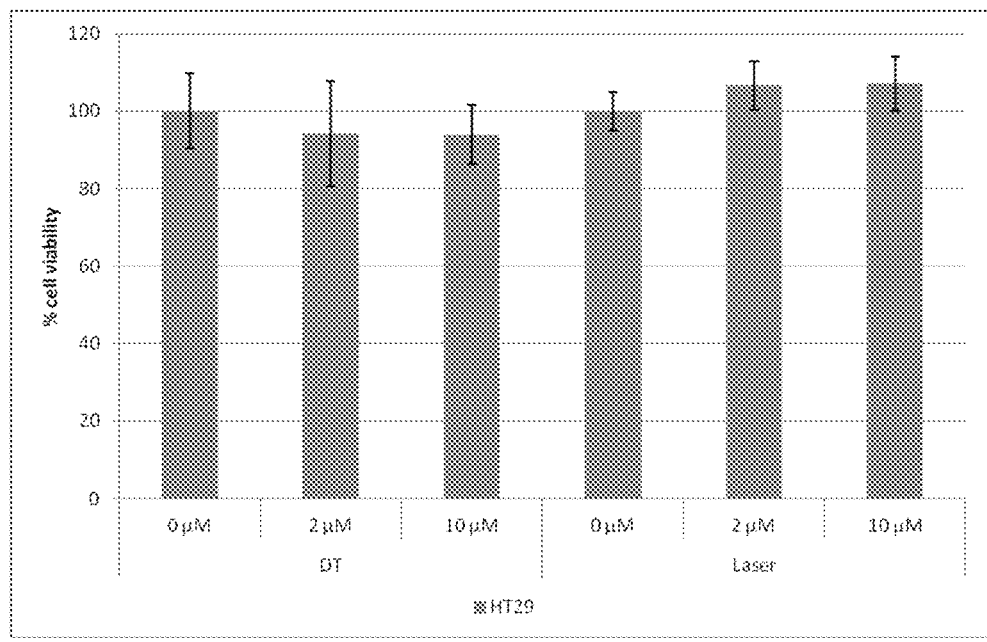
FIG. 16 shows the results of cell tests of 5,10,15-tris-(3-hydroxy¬phenyl)-20-[4-(butyloxy)-tetra¬fluor-phenyl]-porphyrin

The results of this cell test, with 24 h incubation time, irradiation with a 652 nm laser, and 50 J/cm², are shown in FIG. 16.

7.14 Cell Test of 5,10,15-tris-(3-hydroxy-phenyl)-20-[4-(2-hydroxy-ethyloxy)-tetra-fluor-phenyl]-porphyrin

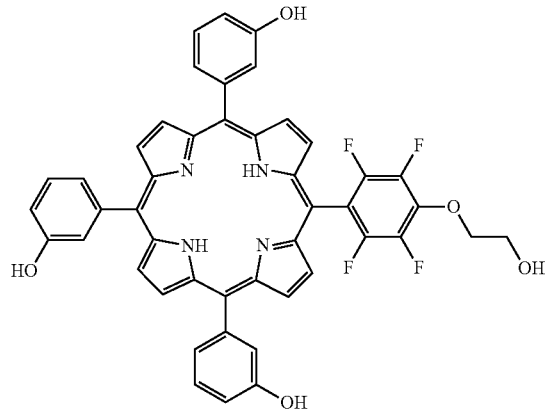 [SMILES: OCCOc1c(F)c(F)c(-c2c3nc(c(-c4cccc(O)c4)c4ccc([nH]4)c(-c4cccc(O)c4)c4nc(c(-c5cccc(O)c5)c5ccc2[nH]5)C=C4)C=C3)c(F)c1F]

Figure 17:
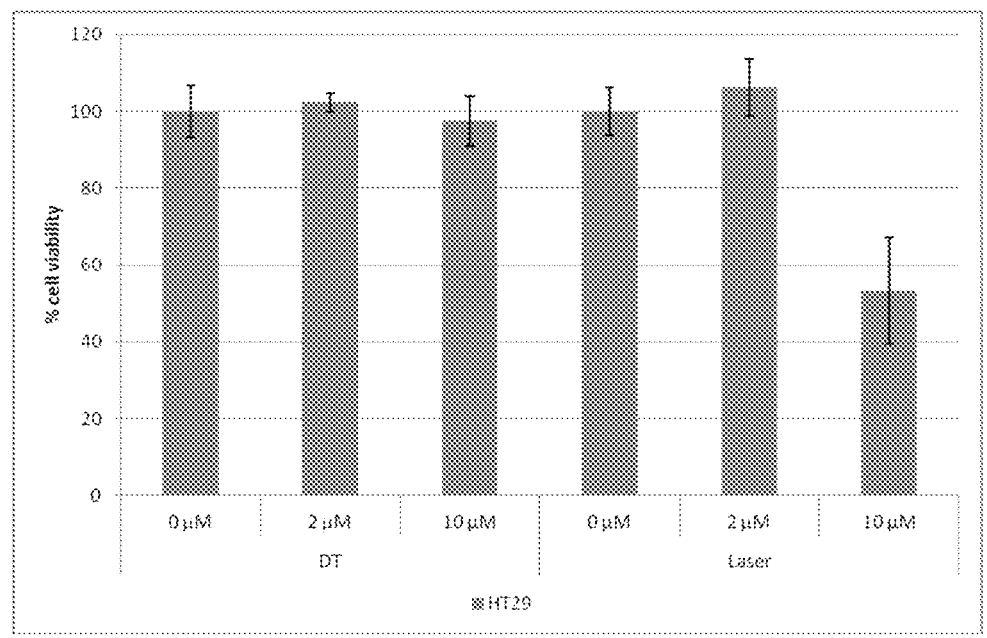
FIG. 17 shows the results of cell tests of 5,10,15-tris-(3-hydroxy¬phenyl)-20-[4-(2-hydroxy-ethyloxy)-tetra-fluor¬phenyl]-porphyrin

The results of this cell test, with 24 h incubation time, irradiation with a 652 nm laser, and 50 J/cm², are shown in FIG. 17.

7.15 Cell Test of 5,10,15-tris-(3-hydroxy-phenyl)-20-[4-(3-hydroxy-propyloxy)-tetra-fluor-¬phenyl]-porphyrin

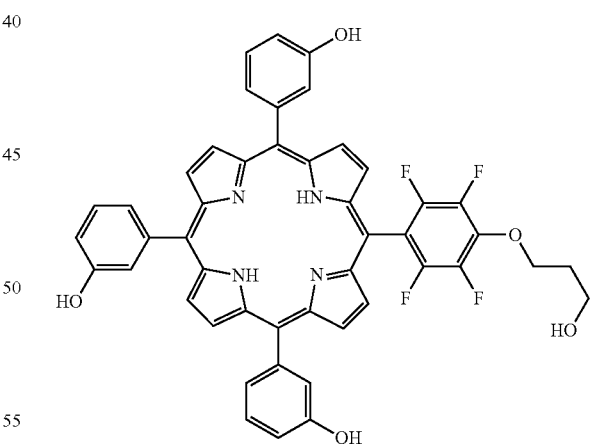

Figure 18:
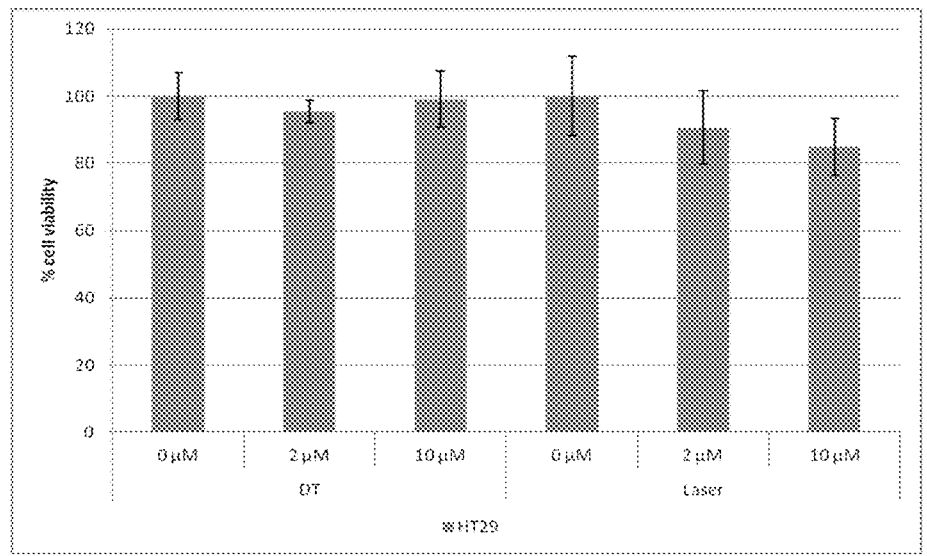
FIG. 18 shows the results of cell tests of 5,10,15-tris-(3-hydroxy¬phenyl)-20-[4-(3-hydroxy-propyloxy)-tetra-fluor¬phenyl]-porphyrin

The results of this cell test, with 24 h incubation time, irradiation with a 652 nm laser, and 50 J/cm², are shown in FIG. 18.

7.16 Cell Test of 5,10,15-tris(3-hydroxy-phenyl)-20-[2,3,5,6-tetra-fluor-4-(1H,1H,5H-octafluoro-pentyloxy)-phenyl]-porphyrin

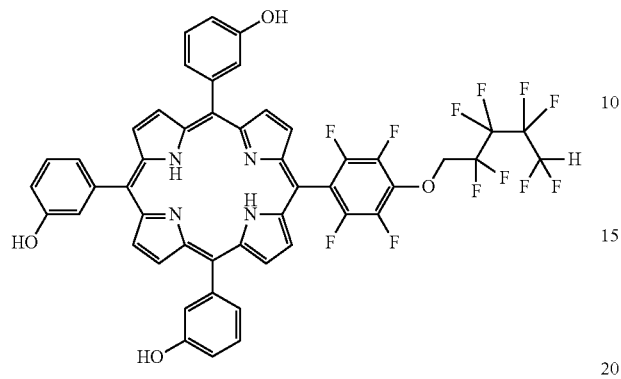

Figure 19:
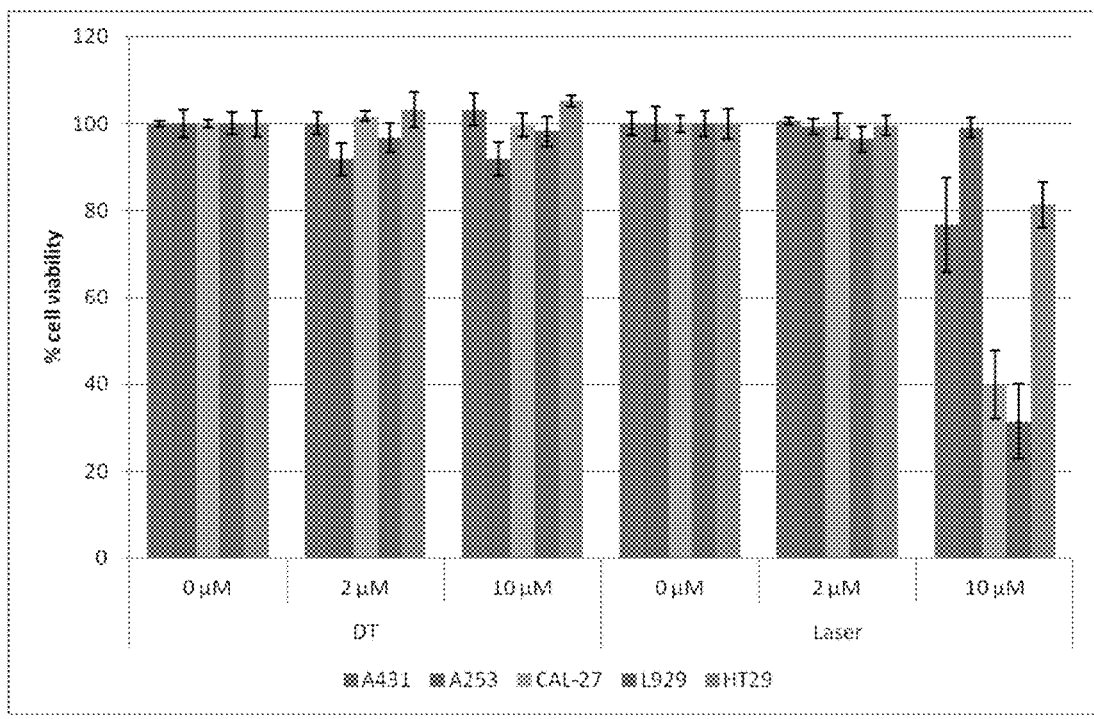
FIG. 19 shows the results of cell tests of 5,10,15-tris(3-hydroxy-phenyl)-20-[2,3,5,6-tetra-fluor¬4-(1H, 1H,5H-octafluoro-pentyloxy)-phenyl]-porphyrin

The results of this cell test, with 24 h incubation time, irradiation with a 652 nm laser, and 50 J/cm², are shown in FIG. 19.

7.17 Cell Test of 5,10,15-tris(3-hydroxy-phenyl)-20-[2,3,5,6-tetra-fluor-4-(1H,1H,7H-dodecafluoro-heptyloxy)-phenyl]-porphyrin

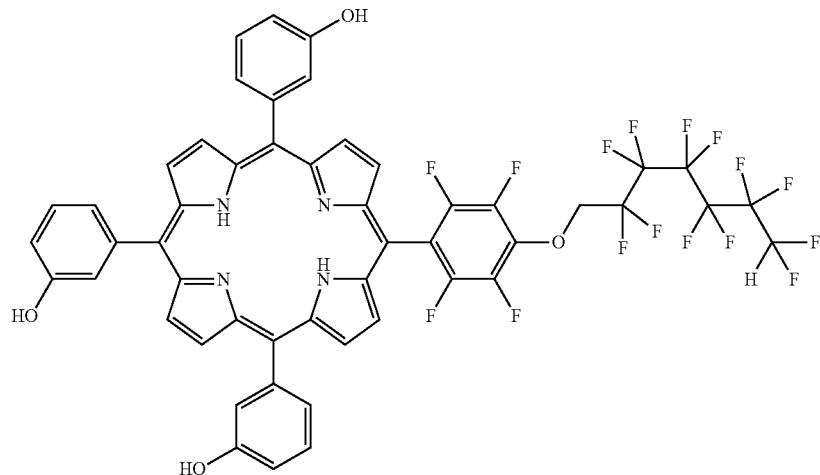 [SMILES: Oc1cccc(-c2c3nc(c(-c4cccc(O)c4)c4ccc([nH]4)c(-c4c(F)c(F)c(OCC(F)(F)C(F)(F)C(F)(F)C(F)(F)C(F)(F)C(F)F)c(F)c4F)c4nc(c(-c5cccc(O)c5)c5ccc2[nH]5)C=C4)C=C3)c1]

Figure 20:
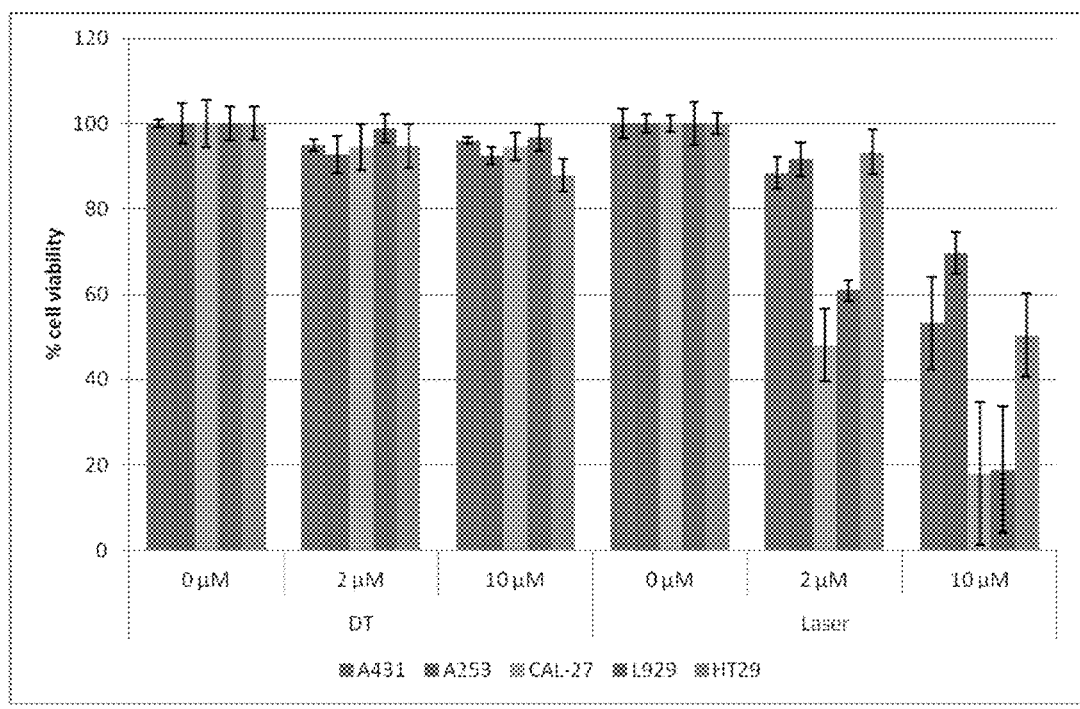
FIG. 20 shows the results of cell tests of 5,10,15-tris(3-hydroxy-phenyl)-20-[2,3,5,6-tetra-fluor¬-4-(1H,1H,7H-dodecafluoroheptyloxy)-phenyl]-porphyrin

The results of this cell test, with 24 h incubation time, irradiation with a 652 nm laser, and 50 J/cm², are shown in FIG. 20.

7.18 Cell Test of 5,10,15,20-Tetrakis-[2,3,5,6-tetra-fluor-4-((S)-2,3-dihydroxyprop-1-ylamino)-phenyl]-porphyrin

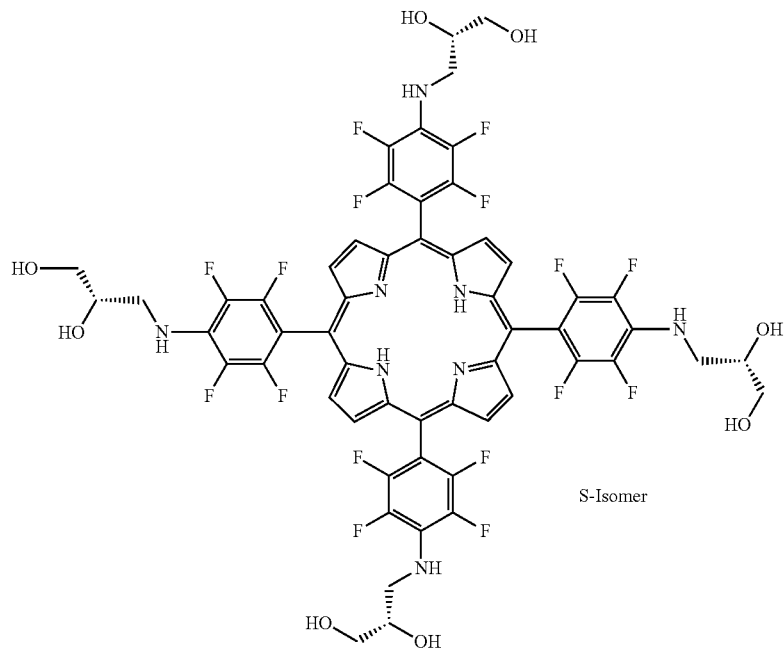 [SMILES: OC[C@@H](O)CNc1c(F)c(F)c(-c2c3nc(c(-c4c(F)c(F)c(NC[C@H](O)CO)c(F)c4F)c4ccc([nH]4)c(-c4c(F)c(F)c(NC[C@H](O)CO)c(F)c4F)c4nc(c(-c5c(F)c(F)c(NC[C@H](O)CO)c(F)c5F)c5ccc2[nH]5)C=C4)C=C3)c(F)c1F]

S-Isomer

Figure 21:
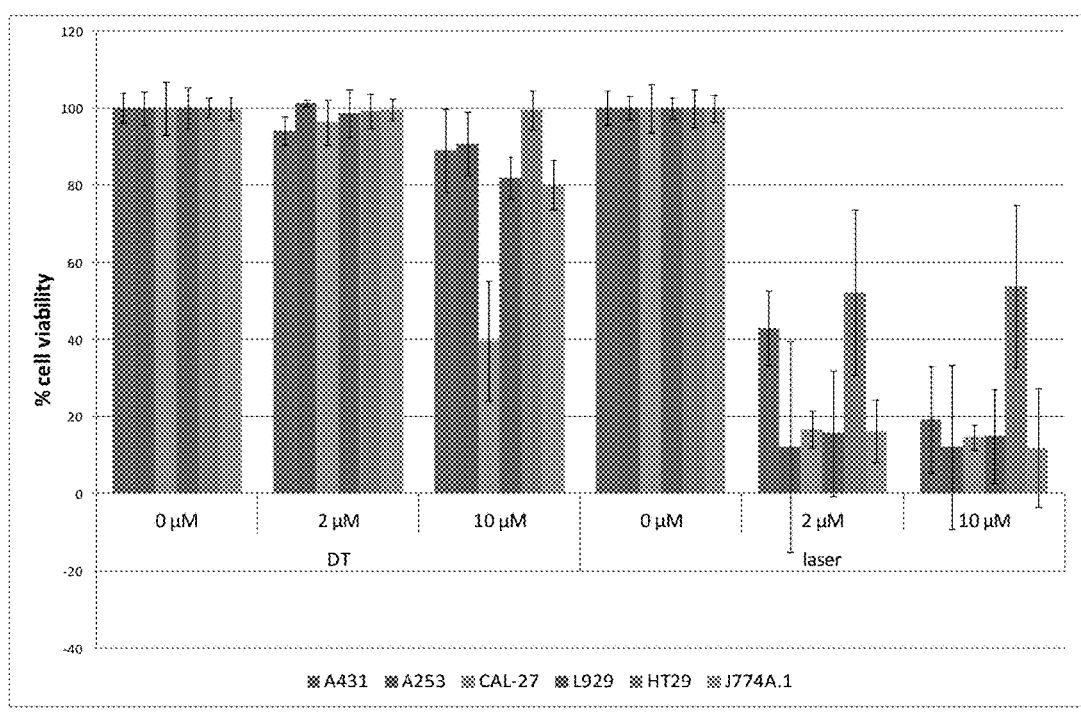
FIG. 21 shows the results of cell tests of 5,10,15,20-Tetrakis-[2,3,5,6-tetrafluor-4-((S)-2,3-dihydroxyprop-1-ylamino)-phenyl]-porphyrin

The results of this cell test, with 24 h incubation time, irradiation with a 652 nm laser, and 50 J/cm², are shown in FIG. 21.

7.19 Cell Test of 5,10,15,20-Tetrakis-[2,3,5,6-tetra-fluor-4-((R)-2,3-dihydroxyprop-1-ylamino)-phenyl]-porphyrin

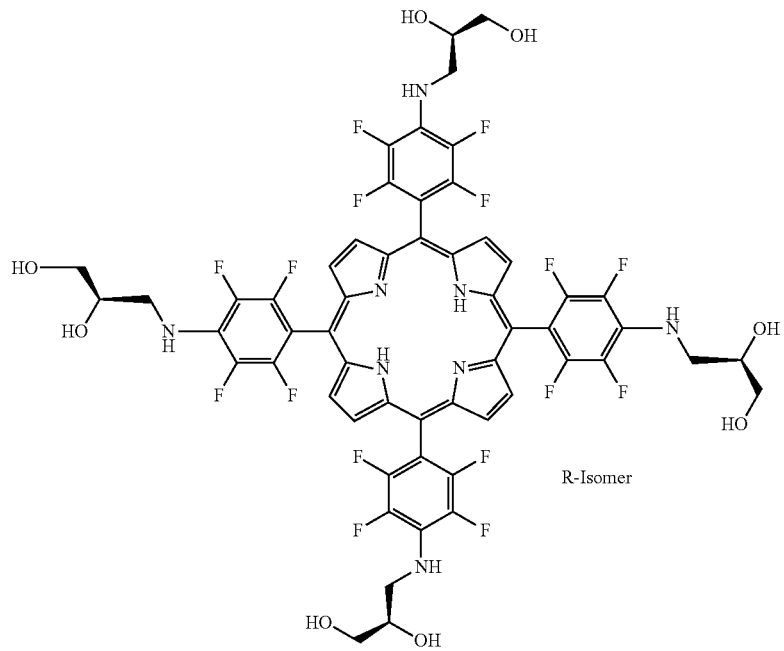 [SMILES: OC[C@H](O)CNc1c(F)c(F)c(-c2c3nc(c(-c4c(F)c(F)c(NC[C@@H](O)CO)c(F)c4F)c4ccc([nH]4)c(-c4c(F)c(F)c(NC[C@@H](O)CO)c(F)c4F)c4nc(c(-c5c(F)c(F)c(NC[C@@H](O)CO)c(F)c5F)c5ccc2[nH]5)C=C4)C=C3)c(F)c1F]

R-Isomer

Figure 22:
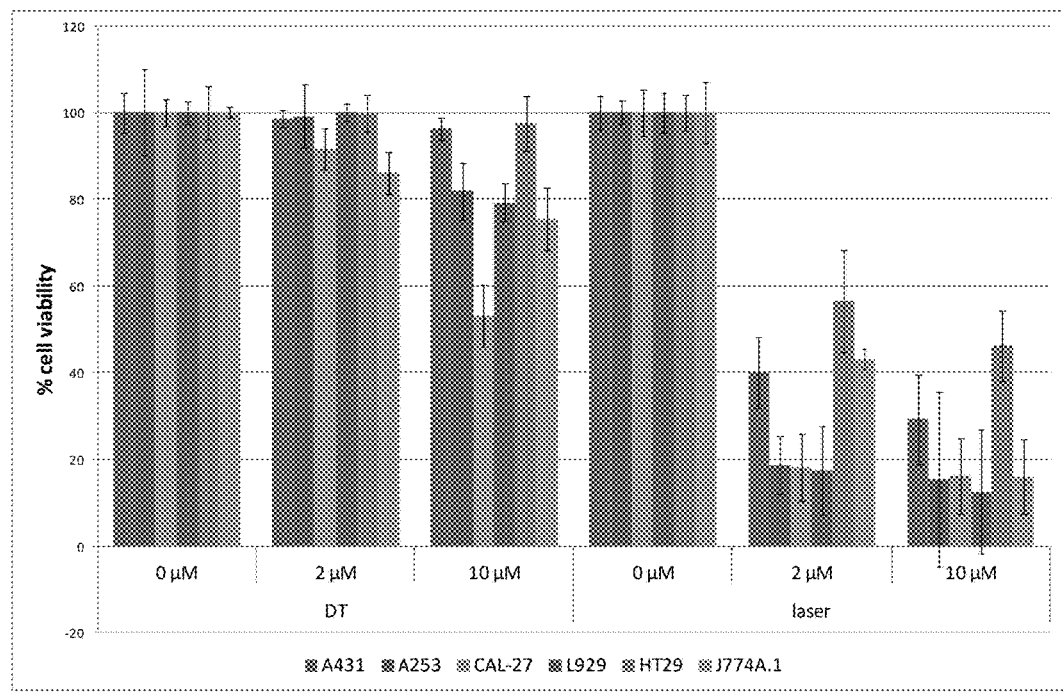
FIG. 22 shows the results of cell tests of 5,10,15,20-Tetrakis-[2,3,5,6-tetrafluor-4-((R)-2,3-dihydroxyprop-1-ylamino)-phenyl]-porphyrin

The results of this cell test, with 24 h incubation time, irradiation with a 652 nm laser, and 50 J/cm², are shown in FIG. 22.

7.20 Cell Test of 5,15-Bis(3-hydroxyphenyl)-10,20-bis-[2,3,5,6-tetrafluor-4-((S)-2,3-dihydroxyprop-1-ylamino)-phenyl]-porphyrin

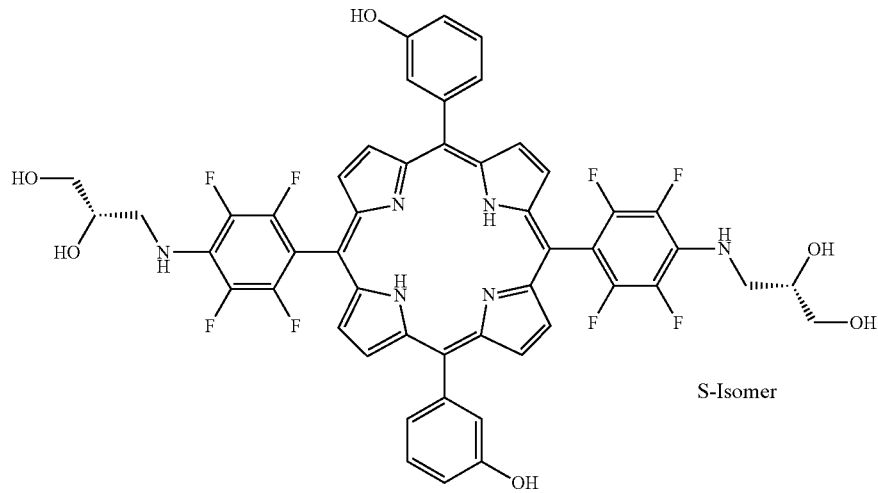 [SMILES: OC[C@@H](O)CNc1c(F)c(F)c(-c2c3nc(c(-c4cccc(O)c4)c4ccc([nH]4)c(-c4c(F)c(F)c(NC[C@H](O)CO)c(F)c4F)c4nc(c(-c5cccc(O)c5)c5ccc2[nH]5)C=C4)C=C3)c(F)c1F]

S-Isomer

Figure 23:
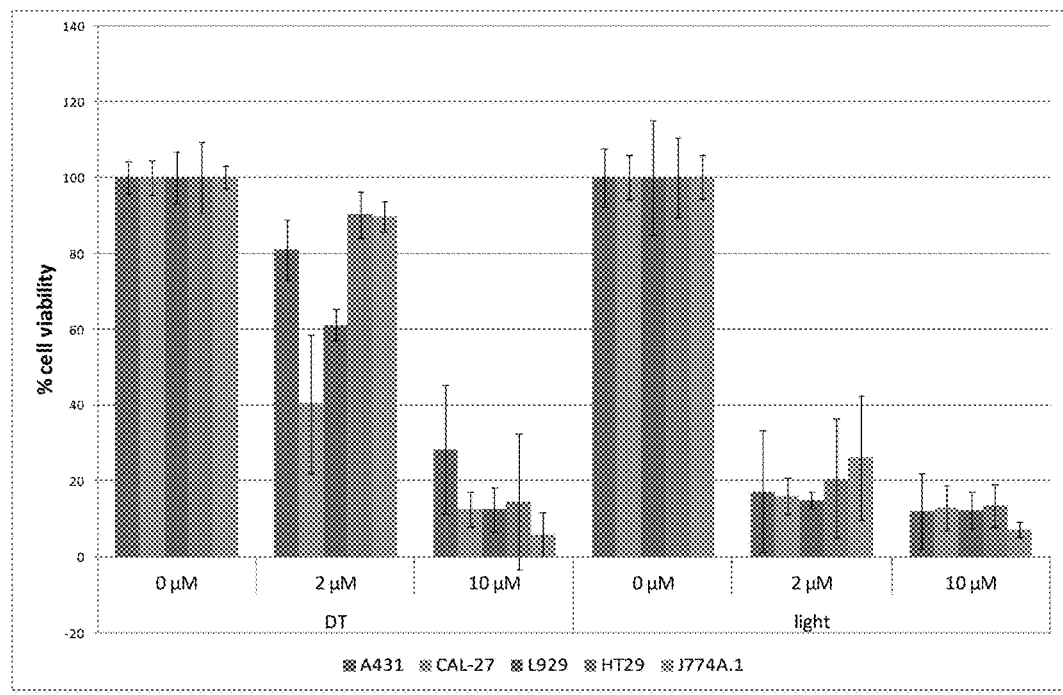
FIG. 23 shows the results of cell tests of 5,15-Bis(3-hydroxyphenyl)-10,20-bis-[2,3,5,6-tetrafluor-4-((S)-2,3-dihydroxyprop-1-ylamino)-phenyl]-porphyrin

The results of this cell test, with 24 h incubation time, irradiation with a 652 nm laser, and 50 J/cm$^2$, are shown in FIG. 23.

7.21 Cell Test of 5,15-Bis(3-hydroxyphenyl)-10,20-bis-[2,3,5,6-tetrafluor-4-((R)-2,3-dihydroxyprop-1-ylamino)-phenyl]-porphyrin

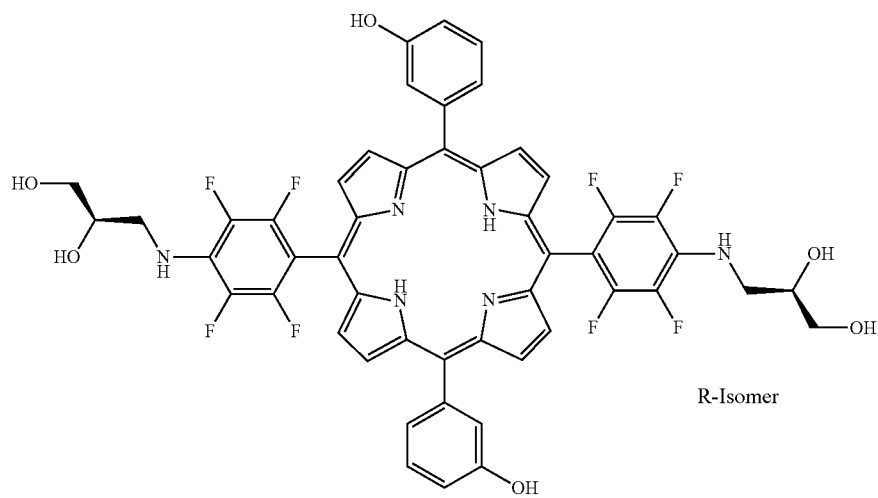 [SMILES: OC[C@H](O)CNc1c(F)c(F)c(-c2c3nc(c(-c4cccc(O)c4)c4ccc([nH]4)c(-c4c(F)c(F)c(NC[C@@H](O)CO)c(F)c4F)c4nc(c(-c5cccc(O)c5)c5ccc2[nH]5)C=C4)C=C3)c(F)c1F]

R-Isomer

Figure 24:
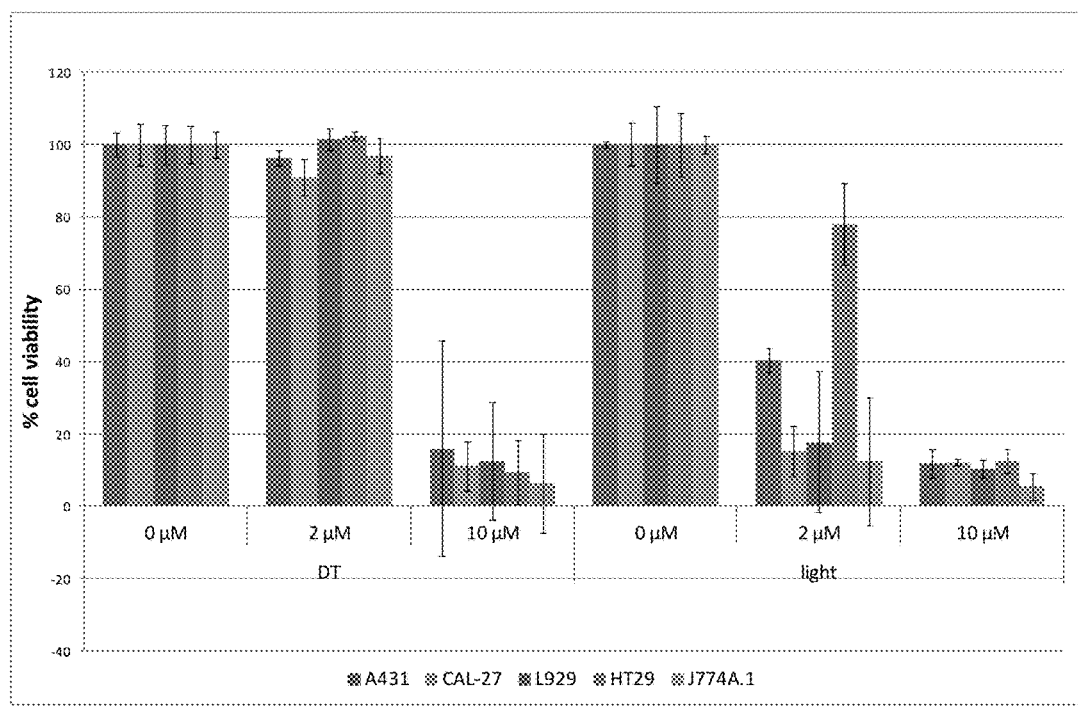
FIG. 24 shows the results of cell tests of 5,15-Bis(3-hydroxyphenyl)-10,20-bis-[2,3,5,6-tetrafluor-4-((R)-2,3-dihydroxyprop-1-ylamino)-phenyl]-porphyrin

The results of this cell test, with 24 h incubation time, irradiation with a 652 nm laser, and 50 J/cm$^2$, are shown in FIG. 24.

7.22 Cell Test of 5,15-Bis(3-hydroxyphenyl)-10,20-bis-[2,3,5,6-tetrafluor-4-(1,3-dihydroxyprop-2-ylamino)-phenyl]-porphyrin

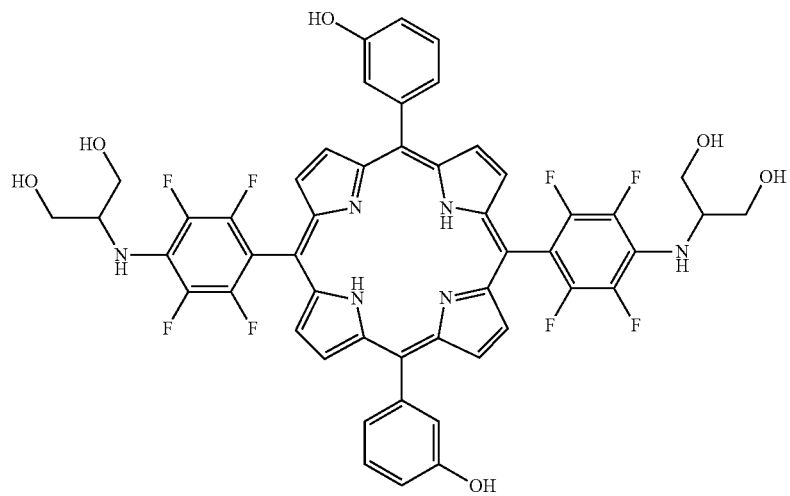 [SMILES: OCC(CO)Nc1c(F)c(F)c(-c2c3nc(c(-c4cccc(O)c4)c4ccc([nH]4)c(-c4c(F)c(F)c(NC(CO)CO)c(F)c4F)c4nc(c(-c5cccc(O)c5)c5ccc2[nH]5)C=C4)C=C3)c(F)c1F]

Figure 25:
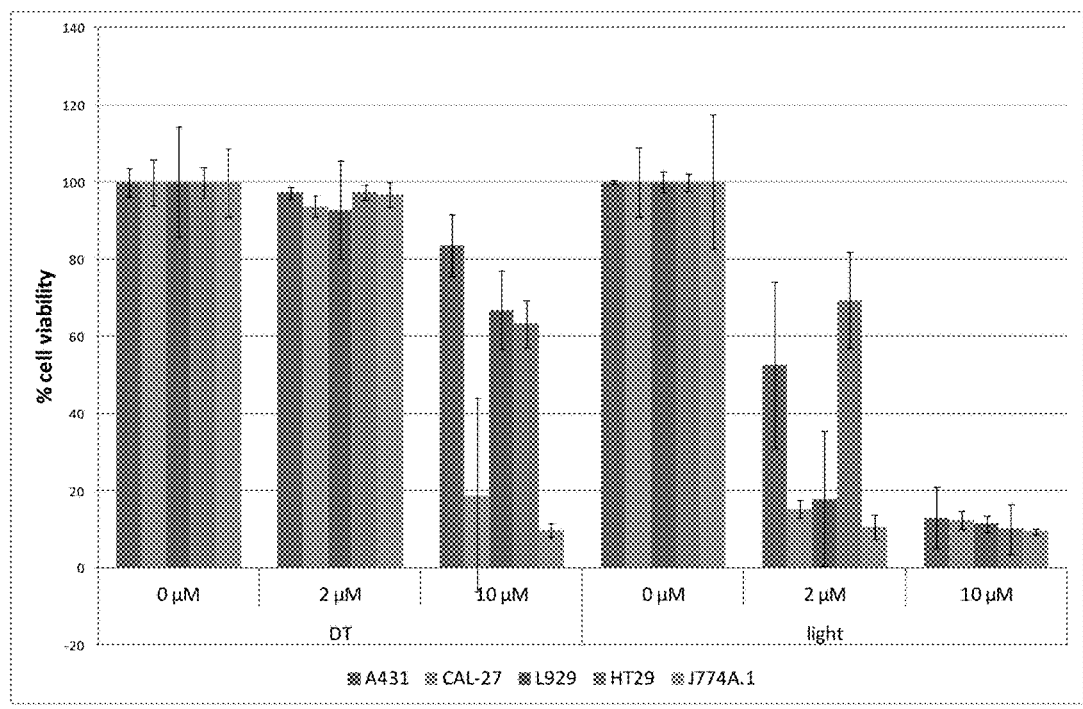
FIG. 25 shows the results of cell tests of 5,15-Bis(3-hydroxyphenyl)-10,20-bis-[2,3,5,6-tetrafluor-4-(1,3-dihydroxyprop-2-ylamino)-phenyl]-porphyrin

The results of this cell test, with 24 h incubation time, irradiation with a 652 nm laser, and 50 J/cm², are shown in FIG. 25.

7.23 Cell Test of 5,10,15-Tris-[2,3,5,6-tetrafluor-4-((R)-2,3-dihydroxyprop-1-yl-amino)-phenyl]-corrole

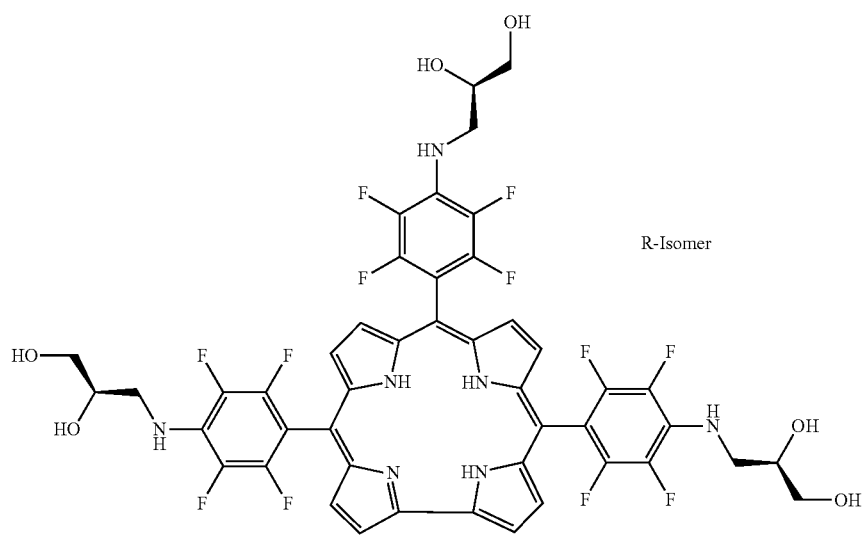 [SMILES: OC[C@H](O)CNc1c(F)c(F)c(-c2c3nc(c4ccc([nH]4)c(-c4c(F)c(F)c(NC[C@@H](O)CO)c(F)c4F)c4ccc([nH]4)c(-c4c(F)c(F)c(NC[C@@H](O)CO)c(F)c4F)c4ccc2[nH]4)C=C3)c(F)c1F]

Figure 26:
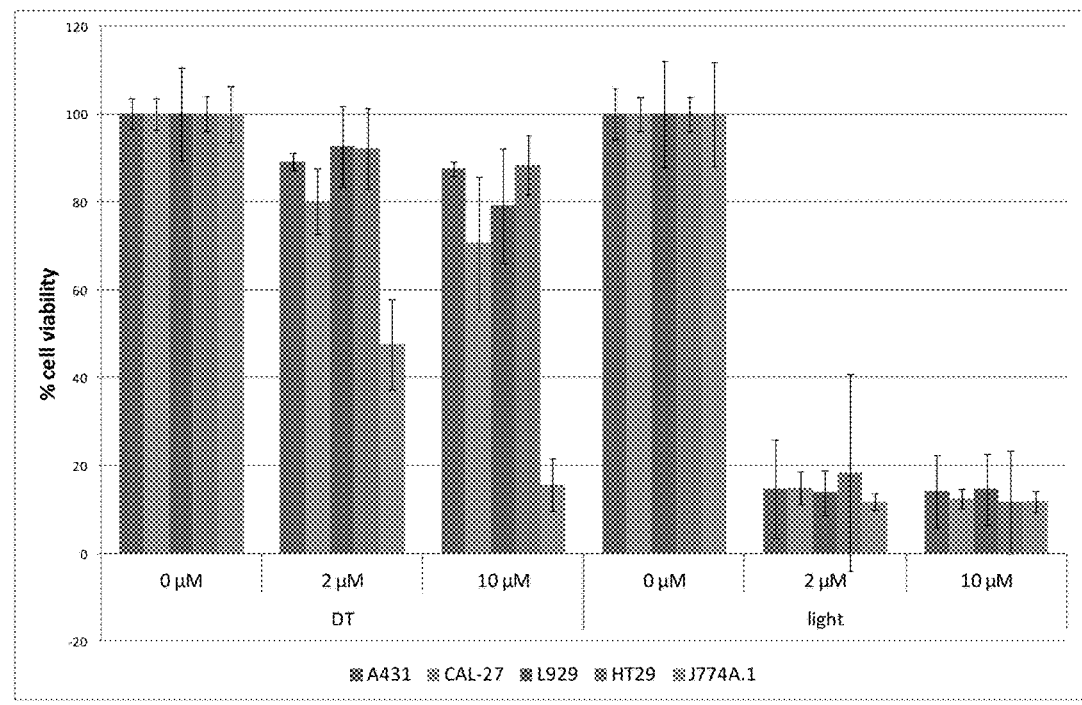
FIG. 26 shows the results of cell tests of 5,10,15-Tris-[2,3,5,6-tetrafluor-4-((R)-2,3-dihydroxyprop-1-yl¬amino)-phenyl]-corrole

The results of this cell test, with 24 h incubation time, irradiation with a 652 nm laser, and 50 J/cm², are shown in FIG. 26.

7.24 Cell Test of 5,10,15-Tris-[2,3,5,6-tetrafluor-4-((S)-2,3-dihydroxyprop-1-yl-amino)-phenyl]-corrol

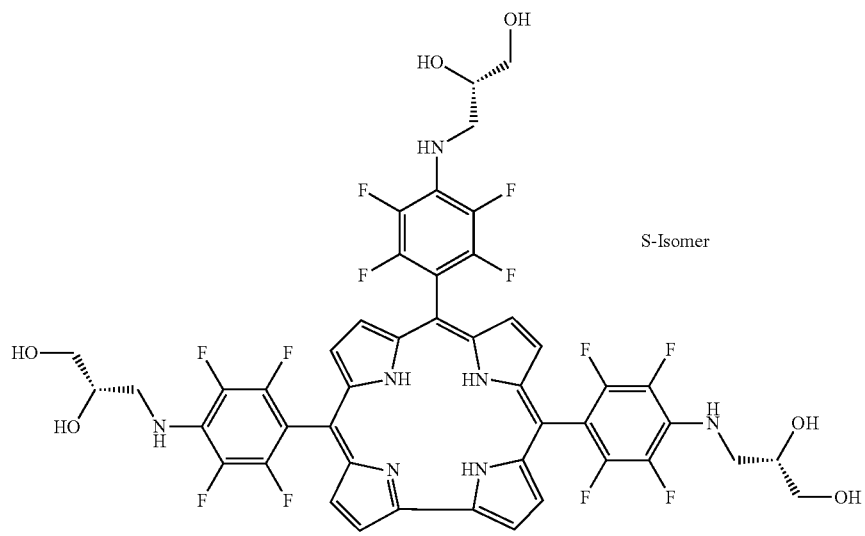 [SMILES: OC[C@@H](O)CNc1c(F)c(F)c(-c2c3nc(c4ccc([nH]4)c(-c4c(F)c(F)c(NC[C@H](O)CO)c(F)c4F)c4ccc([nH]4)c(-c4c(F)c(F)c(NC[C@H](O)CO)c(F)c4F)c4ccc2[nH]4)C=C3)c(F)c1F]

Figure 27:
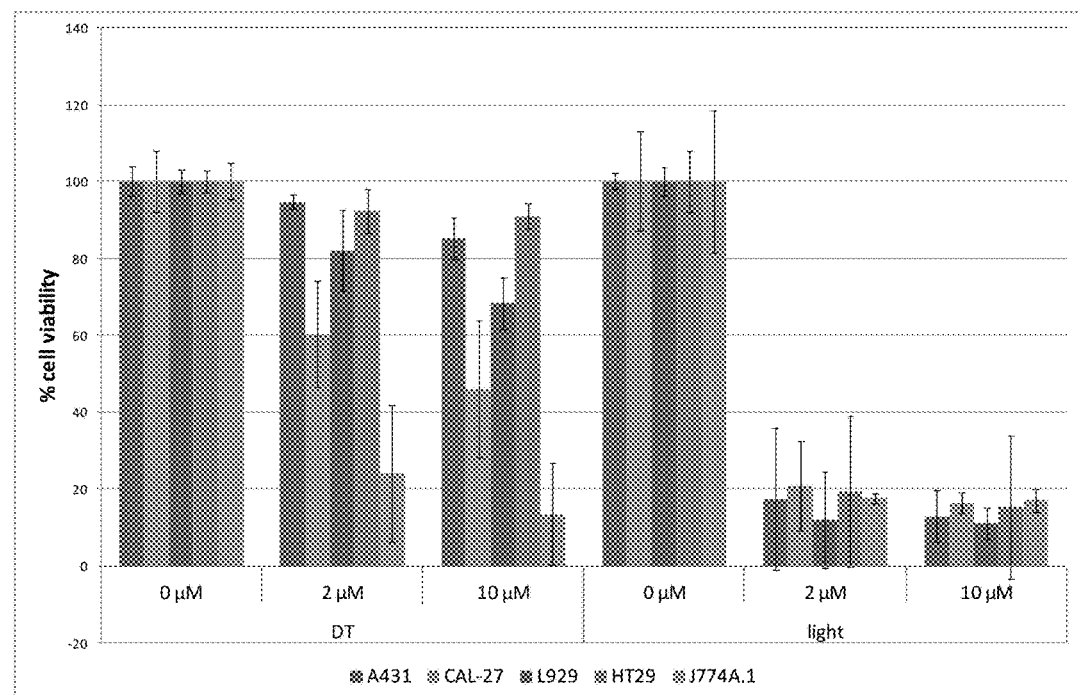
FIG. 27 shows the results of cell tests of 5,10,15-Tris-[2,3,5,6-tetrafluor-4-((S)-2,3-dihydroxyprop-1-yl¬amino)-phenyl]-corrol

The results of this cell test, with 24 h incubation time, irradiation with a 652 nm laser, and 50 J/cm², are shown in FIG. 27.

Having described preferred embodiments of the invention with reference to the accompanying examples, it is to be understood that the invention is not limited to the precise embodiments, and that various changes and modifications may be effected therein by skilled in the art without departing from the scope of the invention as defined in the appended claims.

REFERENCES

[1] B. W. Henderson, T. J. Dougherty, Photodynamic therapy, basic principles and clinical applications, New York: Marcel Dekker, 1992.
[2] A. P. Castano, T. N. Demidova, M. R. Hamblin, «Mechanisms in photodynamic therapy: part one—photosensitizers, photochemistry and cellular localization,» *Photodiagn. Photodyn. Ther.*, no 1, p. 279-293, 2004.
[3] J. G. Moser, Photodynamic tumor therapy. 2nd and 3rd generation photosensitizers, Amsterdam: Harwood Academic Publishers, 1998.
[4] F. Rancan, A. Wiehe, M. Nöbel, M. O. Senge, S. A. Omari, F. Böhm, M. John, B. Röder, «r, Influence of substitutions on asymmetric dihydroxychlorins with regard to intracellular uptake, sub cellular localization and photosensitization in Jurkat cells,» *J. Photochem. Photobiol. B: Biology*, no 78, pp. 17-28, 2005.
[5] D. Aicher, S. Gräfe, C. B. W. Stark, A. Wiehe, «, Synthesis of β-functionalized Temoporfin derivatives for an application in photodynamic therapy,» *Bioorg. Med. Chem. Lett.*, no 21, p. 5808-5811, 2011.
[6] I. Laville, T. Figueiredo, B. Loock, S. Pigaglio, P. Maillard, D. S. Grierson, D. Carrez, A. Croisy, J. Blais, «Synthesis, Cellular Internalization and Photodynamic Activity of Glucoconjugated Derivatives of Tri and Tetra (meta-hydroxyphenyl)chlorines,» *Bioorg. Med. Chem.*, no 11, pp. 1643-1652, 2003.
[7] D. Samaroo, C. E. Soll, L. J. Todaro, C. M. Drain, «Efficient microwave-assisted synthesis of amine-substituted Tetrakis(pentafluorophenyl)porphyrin,» *Org. Lett.*, no 8, p. 4985-4988, 2006.
[8] B. Koszarna, D. T. Gryko, «Efficient Synthesis of meso-Substituted Corroles in a H2O-MeOH Mixture,» *J. Org. Chem.*, vol. 71, pp. 3707-3717, 2006.
[9] J.-Y. Shin, H. Furuta, K. Yoza, S. Igarashi, A. Osuka, «meso-Aryl-Substituted Expanded Porphyrins,» *J. Am. Chem. Soc.*, vol. 123, pp. 7190-7191, 2001.
[10] S. P. Songca, «In-vitro activity and tissue distribution of new fluorinated meso-tetrahydroxyphenylporphyrin photosensitizers,» *J. Pharm. Pharmacol.*, vol. 53, p. 1469-1475, 2001.
[11] R. Bonnett, R. D. White, U.-J. Winfield, M. C. Berenbaum, «Hydroporphyrins of the meso-tetra(hydroxyphenyl)porphyrin series as tumor photosensitizers,» *Biochem. J.*, vol. 261, p. 277 280, 1989.
[12] J. S. Lindsey, I. C. Schreiman, H. C. Hsu, P. C. Kearney, A. M. Marguerettaz, *J. Org. Chem.*, vol. 52, p. 827-836, 1987.
[13] C.-H. Lee, J. S. Lindsey, «One-Flask Synthesis of Meso-Substituted Dipyrromethanes and Their Application in the Synthesis of Trans-Substituted Porphyrin Building Blocks,» *Tetrahedron*, vol. 50, p. 11427-11440, 1994.

What is claimed is:
1. A compound based on the formulas 1, 2, 3, 4 or 5:
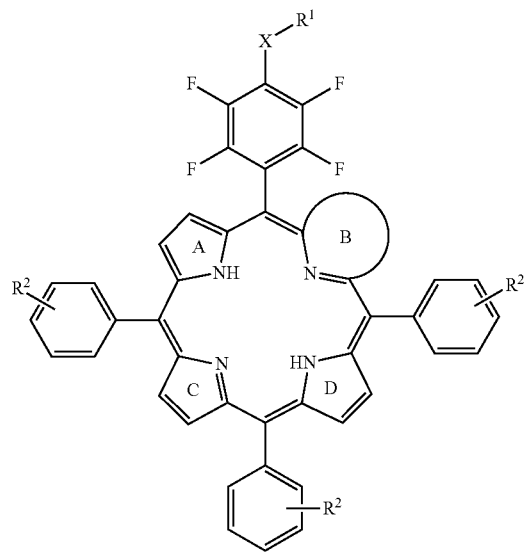
1
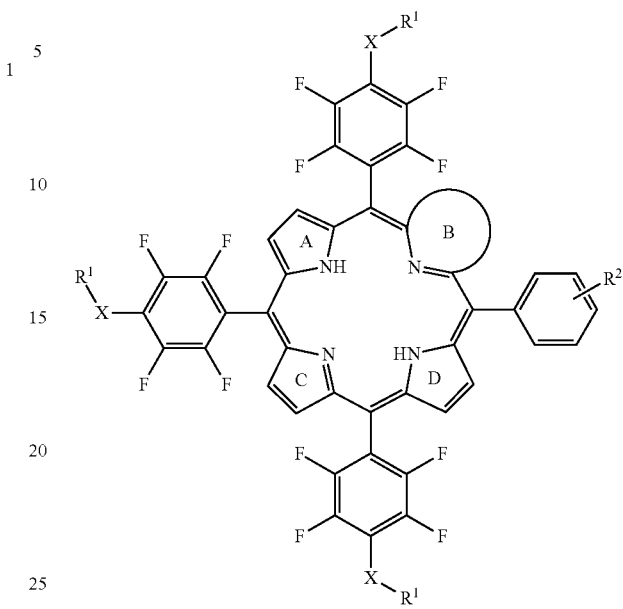
3
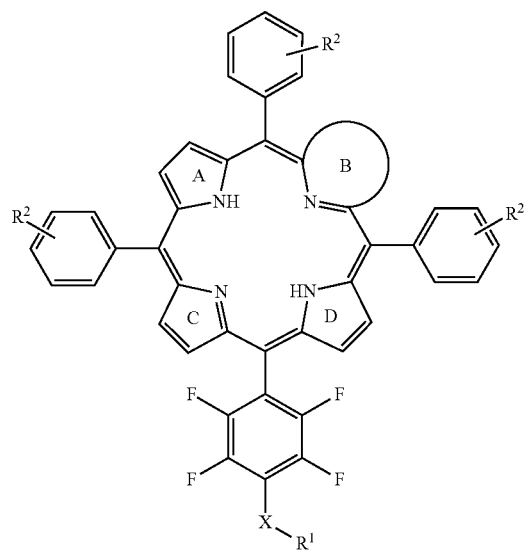
2
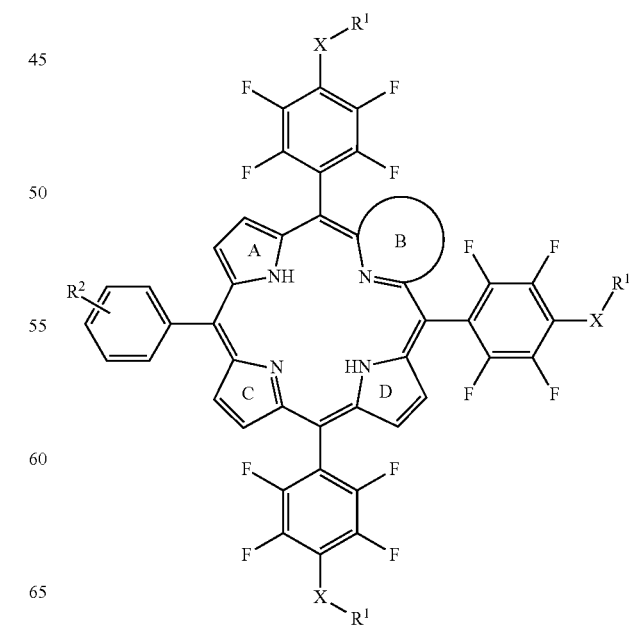
4

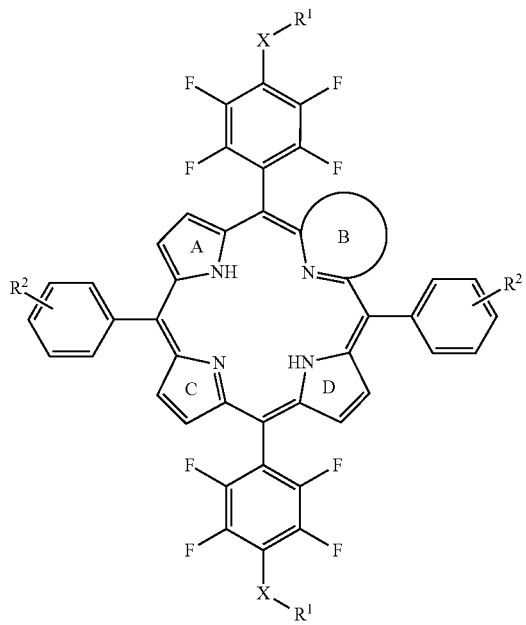

Wherein:

B is:

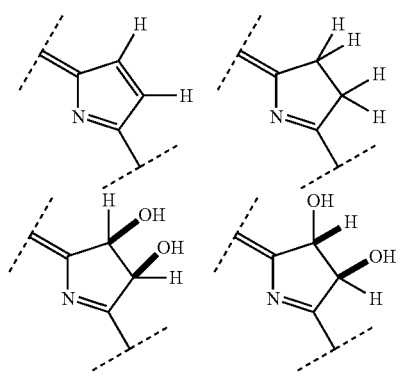

X is NH, O or S;

R¹ is a linear or branched alkyl chain with 2-4 carbon atoms and containing at least one hydroxyl moiety;

R² is a substituent either in the meta- or para-position of the phenyl ring with R²=—OH, —COOH, —NH₂, —COOY, —NHY, OY, —NH—Z—COOH, or —CO—Z—NH₂;

wherein

Y is a polyethyleneglycol-residue with (CH₂CH₂O)$_n$CH₃ with n=1-30 or a carbohydrate moiety;

Z is peptides or oligopeptides wherein n=1-30.

2. The tetrapyrrolic compound according to claim 1, based on the formulas 1, 2, 3, 4, or 5, wherein R¹ is CH(CH₂OH)₂, CH₂—CH(OH)—CH₂OH, or CH(OH)—CH(OH)—CH₃; and/or R² is a substituent either in the meta- or pare-position of the phenyl ring with R²=—OH, —COOH, or —NH₂.

3. The tetrapyrrolic compound according to claim 2, having the formula selected from the group consisting of:

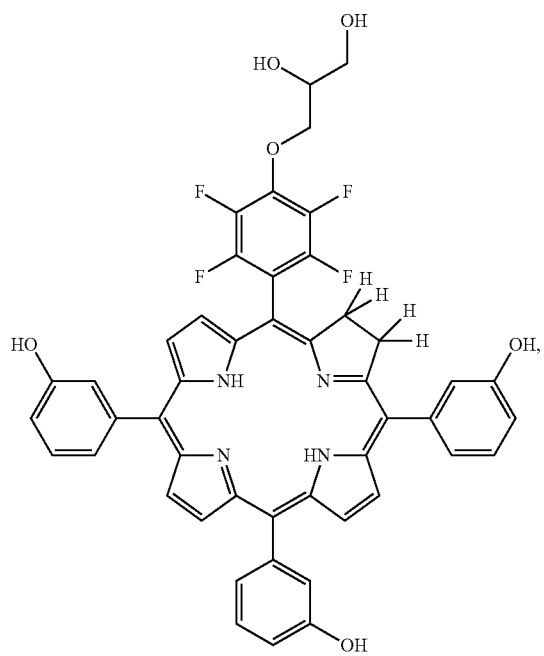

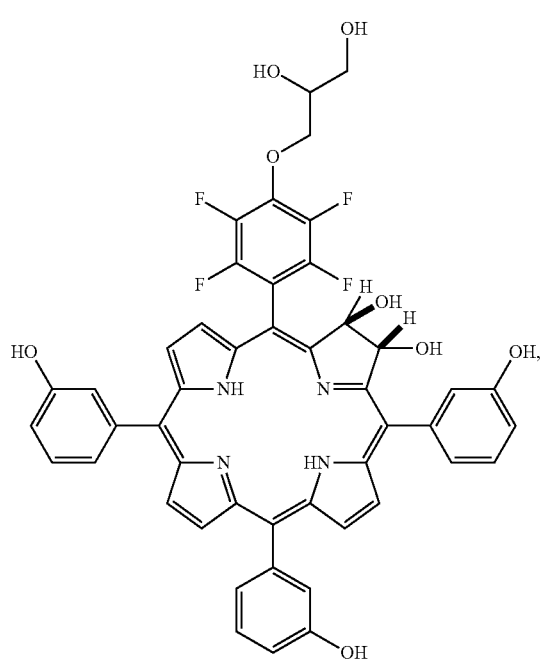

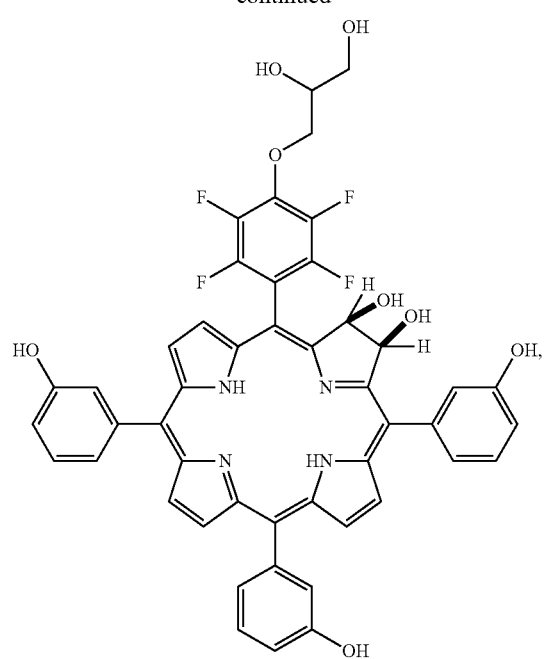
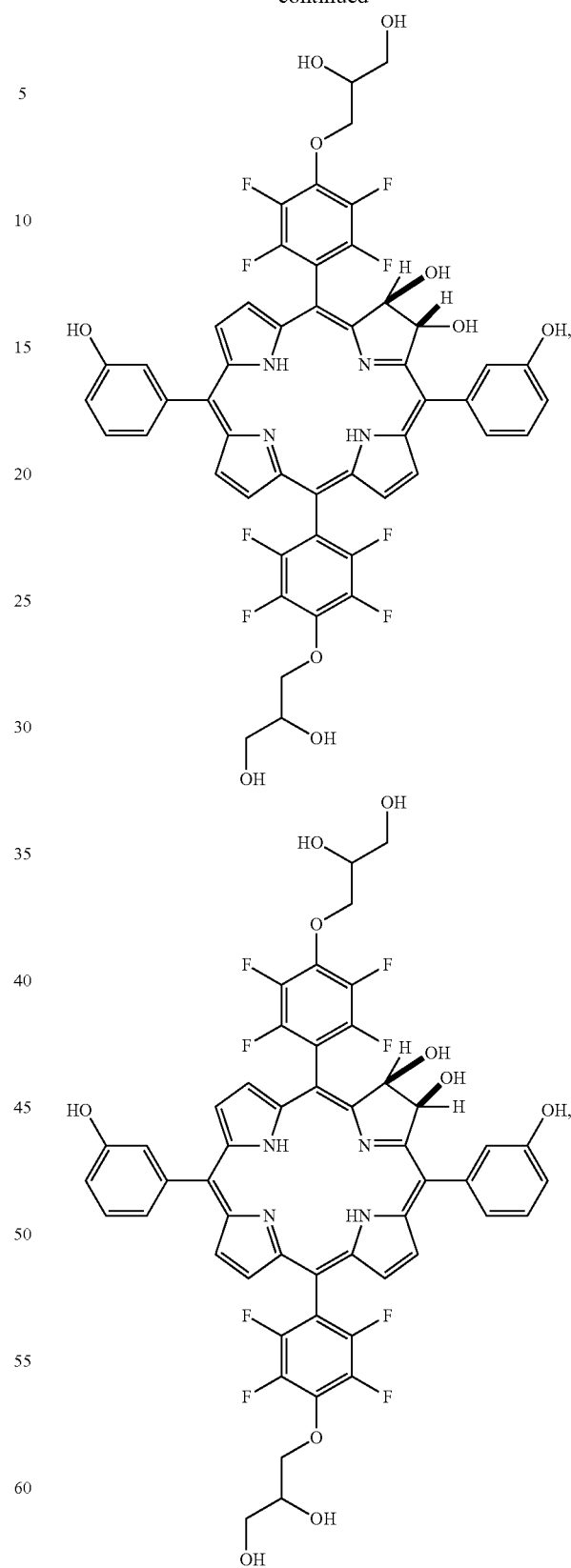
and
a pharmaceutically acceptable derivative thereof.

4. A tetrapyrrolic compound based on the formulas 1, 3, 5 or 6:
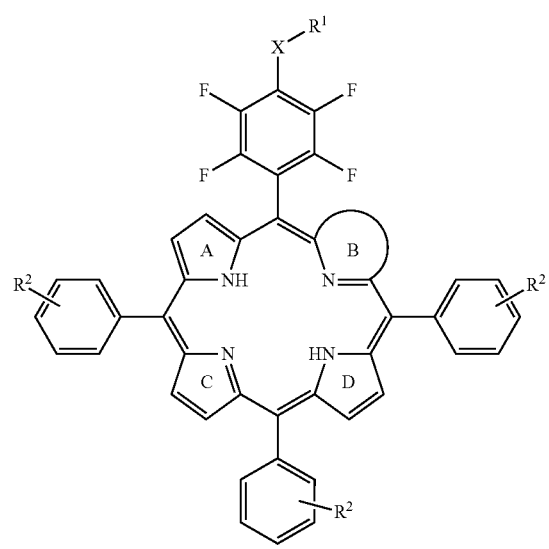
1
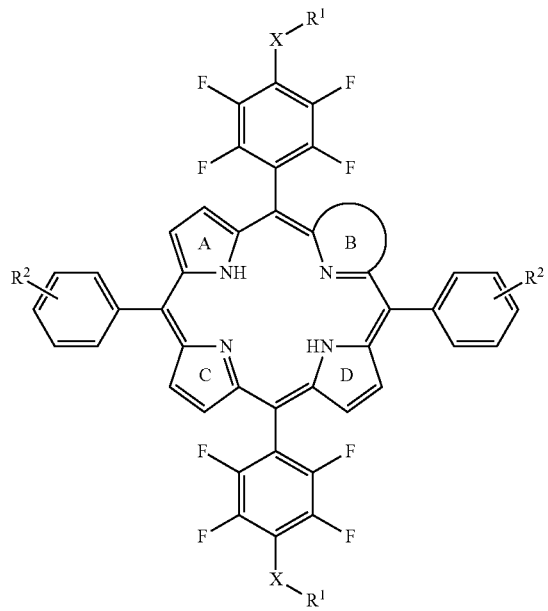
5
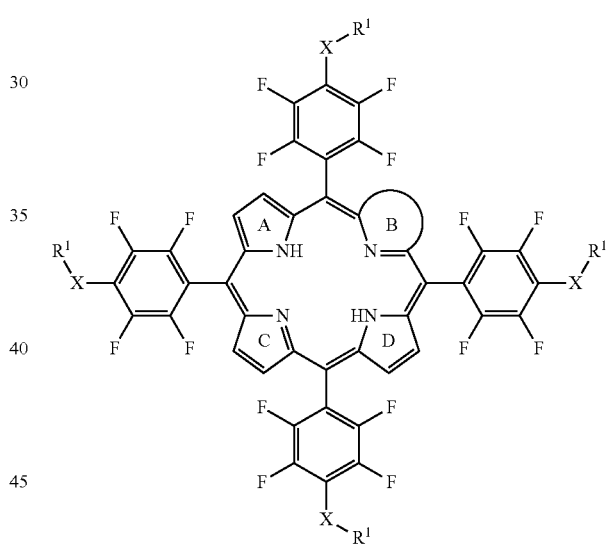
6
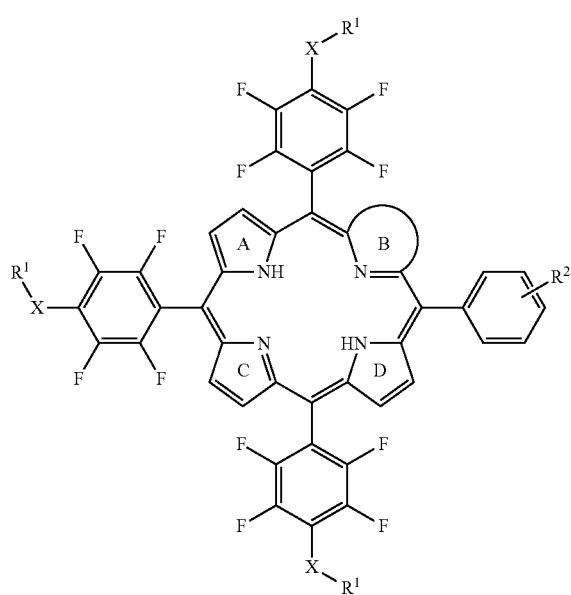
3
Wherein: B is:
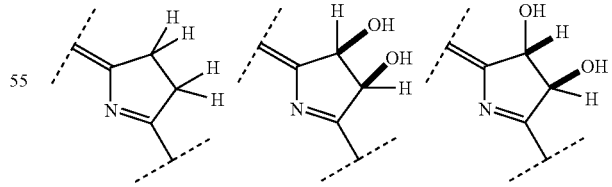
X is NH, O or S;
R$^1$ is a linear or branched alkyl chain with 24 carbon atoms and containing at least one hydroxyl moiety;
R$^2$ is a substituent either in the meta- or para-position of the phenyl ring with R$^2$=—OH, —COOH, —NH$_2$, —COOY, —NHY, OY, —NH—Z—COOH, or —CO—Z—NH$_2$;

wherein:
  Y is a polyethyleneglycol-residue with $(CH_2CH_2O)CH_3$ with n=1-30 or a carbohydrate moiety;
  Z is peptides or oligopeptides wherein n=1-30.
5. A tetrapyrrolic compound based on the formulas 1, 3, 5 or 6:
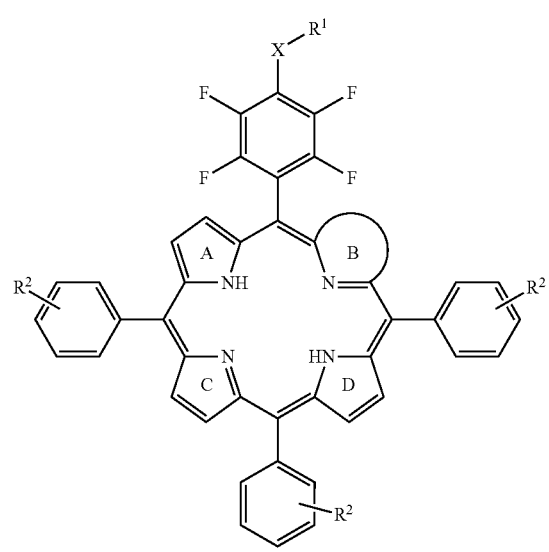
1
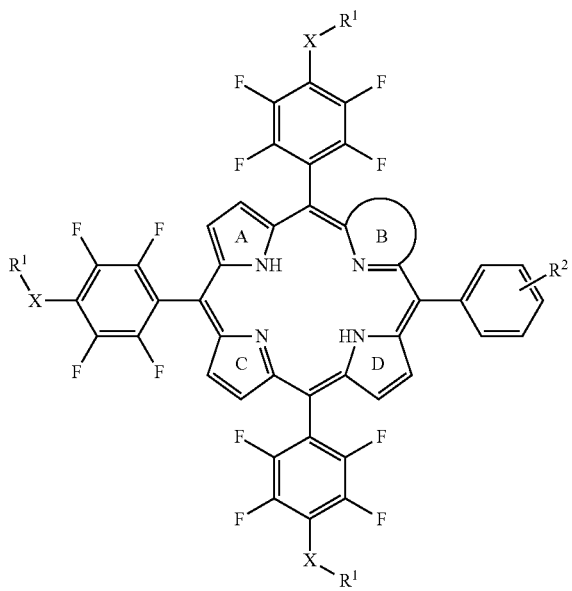
3
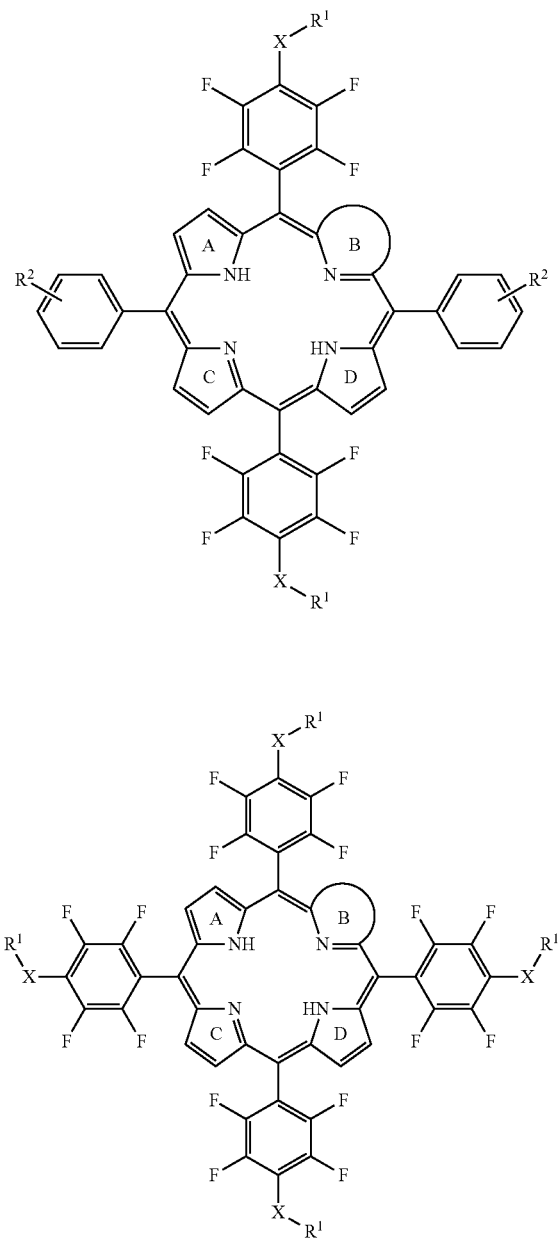
5
6
Wherein: B is:
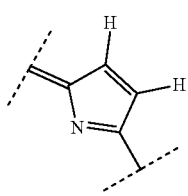
X is NH, O or S;
R$^1$ is $CH(CH_2OH)_2$, $CH_2$—$CH(OH)$—$CH_2OH$, or $CH(OH)$—$CH(OH)$—$CH_3$;

R² is a substituent either in the meta- or pare-Position of the phenyl ring with R^Z=—OH, —COOH, —NH₂, —COOY, —NHY, OY, —NH—Z—COOH, or —CO—Z—NH₂;

wherein:
Y is a polyethyleneglycol-residue with $(CH_2CH_2)_nCH_3$ with n=1-30 or a carbohydrate moiety:
Z is peptides or oligopeptides wherein n=1-30.

6. The tetrapyrrolic compound according to claim 5, having the formula selected from the group consisting of:

and a pharmaceutically acceptable derivative thereof.

7. A pharmaceutical composition comprising a compound according to claim 1 or a pharmaceutically acceptable derivative thereof as an active ingredient.

8. The pharmaceutical composition according to claim 7, wherein said pharmaceutical composition is selected from the group consisting of a liposomal formulation, a formulation employing PLGA particles, a formulation employing

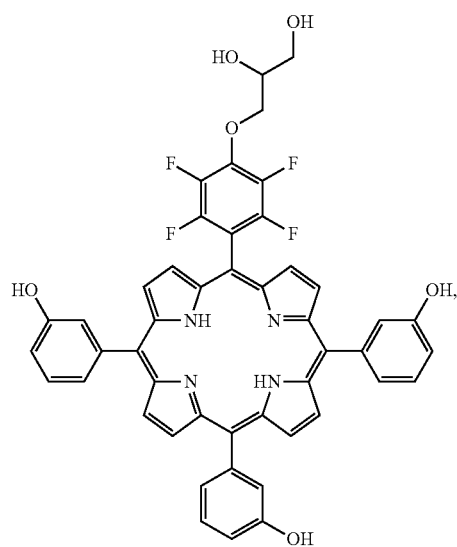

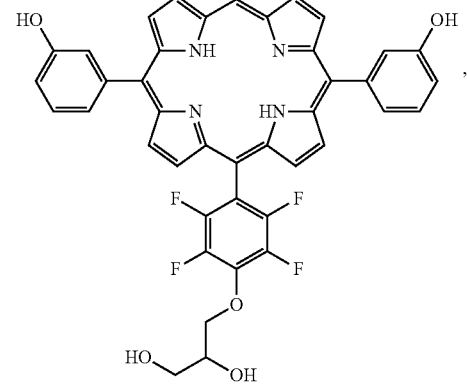

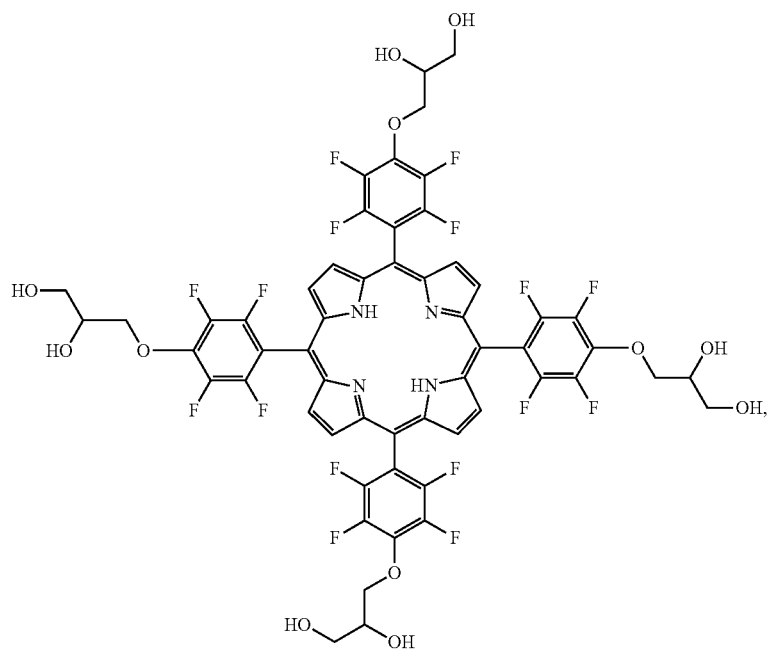

HSA particles, a formulation employing cyclodextrines, and a formulation employing polymer particles.

9. The pharmaceutical composition according to claim 7, wherein said compound is conjugated to a targeting agent; and said targeting agent is selected from the group consisting of an antibody, a fragment of an antibody and a peptide.

10. The tetrapyrrolic compound according to claim 4, having the formula selected from the group consisting of:

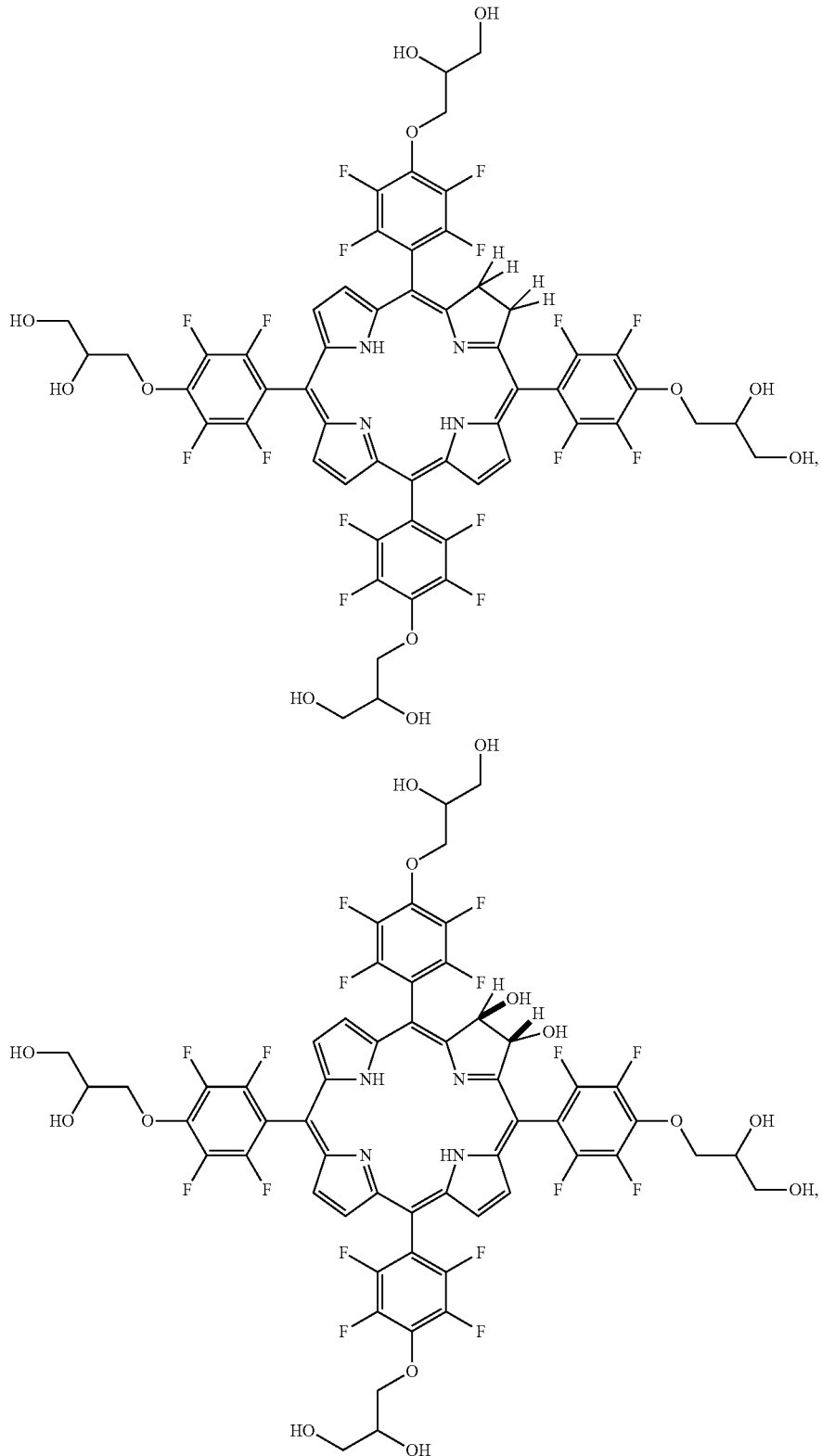 [SMILES: OCC(O)COc1c(F)c(F)c(-c2c3nc(c(-c4c(F)c(F)c(OCC(O)CO)c(F)c4F)c4ccc([nH]4)c(-c4c(F)c(F)c(OCC(O)CO)c(F)c4F)c4nc(c(-c5c(F)c(F)c(OCC(O)CO)c(F)c5F)c5ccc2[nH]5)CC4)C=C3)c(F)c1F ; OCC(O)COc1c(F)c(F)c(-c2c3nc(c(-c4c(F)c(F)c(OCC(O)CO)c(F)c4F)c4ccc([nH]4)c(-c4c(F)c(F)c(OCC(O)CO)c(F)c4F)c4nc(c(-c5c(F)c(F)c(OCC(O)CO)c(F)c5F)c5ccc2[nH]5)[C@@H](O)[C@@H]4O)C=C3)c(F)c1F]

-continued

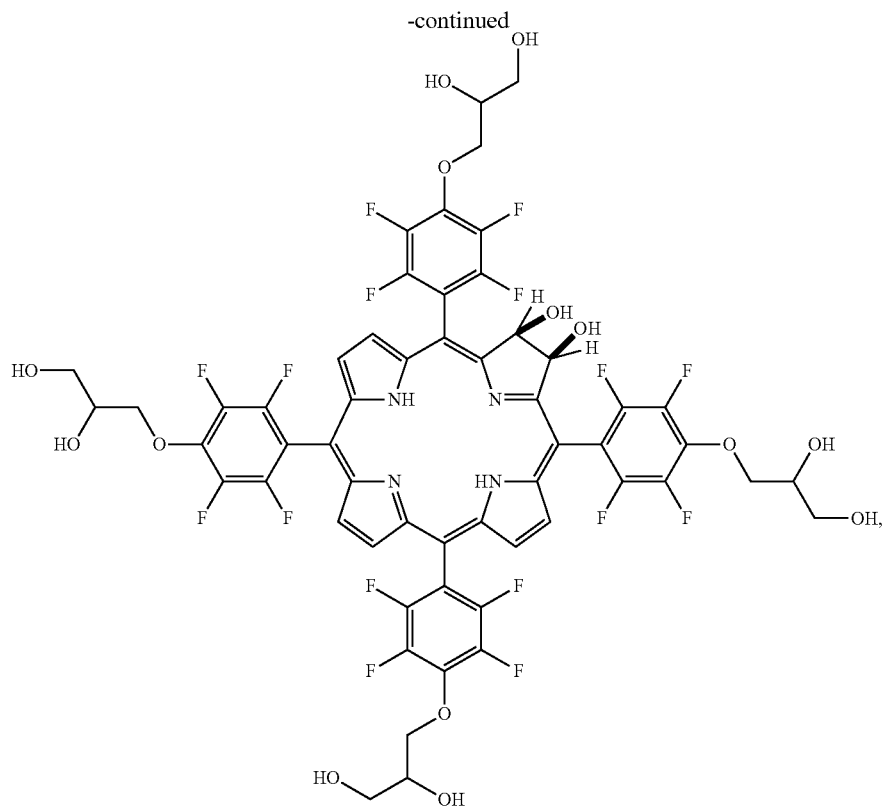

and
a pharmaceutically acceptable derivative thereof.

11. A pharmaceutical composition comprising a compound according to claim 4 or a pharmaceutically acceptable derivative thereof as an active ingredient.

12. The pharmaceutical composition according to claim 11, wherein said pharmaceutical composition is selected from the group consisting of a liposomal formulation, a formulation employing PLGA particles, a formulation employing HSA particles, a formulation employing cyclodextrines, and a formulation employing polymer particles.

13. The pharmaceutical composition according to claim 11, wherein said compound is conjugated to a targeting agent; and said targeting agent is selected from the group consisting of an antibody, a fragment of an antibody and a peptide.

14. A pharmaceutical composition comprising a compound according to claim 5 or a pharmaceutically acceptable derivative thereof as an active ingredient.

15. The pharmaceutical composition according to claim 14, wherein said pharmaceutical composition is selected from the group consisting of a liposomal formulation, a formulation employing PLGA particles, a formulation employing HSA particles, a formulation employing cyclodextrines, and a formulation employing polymer particles.

16. The pharmaceutical composition according to claim 14, wherein said compound is conjugated to a targeting agent; and said targeting agent is selected from the group consisting of an antibody, a fragment of an antibody and a peptide.

\* \* \* \* \*